US012752047B2

(12) United States Patent
Tachibana et al.

(10) Patent No.: US 12,752,047 B2
(45) Date of Patent: Oct. 6, 2026

(54) FLOW CONTROL MECHANISM FOR KIDNEY STONE TREATMENT SYSTEM

(71) Applicant: CALYXO, INC., Pleasanton, CA (US)

(72) Inventors: Brian Y. Tachibana, San Carlos, CA (US); Calvin Lam, San Leandro, CA (US); Ling Tong, Fremont, CA (US); Joe Catanese, III, Pleasanton, CA (US); Caralin Riva Adair, Santa Rosa, CA (US); Andrew John Hudson, Santa Rosa, CA (US); Eddie Gonzalez, Santa Cruz, CA (US); Andrew Johnston, Shingle Springs, CA (US)

(73) Assignee: CALYXO, INC., Pleasanton, CA (US)

( * ) Notice: Subject to any disclaimer, the term of this patent is extended or adjusted under 35 U.S.C. 154(b) by 704 days.

(21) Appl. No.: 18/216,507

(22) Filed: Jun. 29, 2023

(65) Prior Publication Data

US 2024/0001075 A1 Jan. 4, 2024

Related U.S. Application Data

(60) Provisional application No. 63/357,468, filed on Jun. 30, 2022.

(51) Int. Cl.

*A61M 25/00* (2006.01)
*A61M 1/00* (2006.01)
*A61M 25/01* (2006.01)

(52) U.S. Cl.

CPC ........ *A61M 1/774* (2021.05); *A61M 25/0026* (2013.01); *A61M 25/0136* (2013.01);

(Continued)

(58) Field of Classification Search

CPC .......... A61M 1/71; A61M 1/74; A61M 1/741; A61M 1/742; A61M 1/743; A61M 1/76;

(Continued)

(56) References Cited

U.S. PATENT DOCUMENTS 3,065,749 A 11/1962 Brass
3,438,607 A 4/1969 Williams et al.

(Continued)

FOREIGN PATENT DOCUMENTS

CN 203776869 U 8/2014
CN 203776946 U 8/2014

(Continued)

OTHER PUBLICATIONS

Non-final office action mailed Jan. 21, 2022 for U.S. Appl. No. 17/489,733; 6 pages.

(Continued)

*Primary Examiner* — Philip R Wiest

(74) *Attorney, Agent, or Firm* — Squire Patton Boggs (US) LLP

(57) ABSTRACT

Kidney stone removal system is disclosed having components including a handle mechanism. The handle mechanism employs a trigger mechanism that enables control of irrigation and vacuum/suction. Operation of a trigger of the trigger mechanism conveys status of vacuum/suction and irrigation to a user by providing increased resistance at different points of operation. When the trigger is in a home position, irrigation and vacuum/suction are turned off. When the trigger is in a fully activated position, irrigation and vacuum/suction are turned on. When the trigger is in an intermediate position, irrigation may be turned on, while vacuum/suction remains turned off. The handle mechanism can be of a single trigger design with modes including: an active irrigation mode only (i.e., active irrigation on/vacuum off) and an active irrigation mode in combination with a vacuum mode (i.e., active irrigation on/vacuum on). The handle mechanism can also be of a single trigger design with modes including passive irrigation on/active irrigation off/ vacuum off; passive irrigation on/active irrigation (Continued)

on/vacuum off; passive irrigation on/active irrigation on/vacuum on. The handle mechanism can also provide a minimum, passive amount of negative pressure even in the modes where the vacuum is off.

23 Claims, 49 Drawing Sheets

(52) U.S. Cl.
CPC ............... *A61M 2025/0031* (2013.01); *A61M 2210/1082* (2013.01)

(58) Field of Classification Search
CPC .... A61M 1/77; A61M 1/774; A61M 25/0026; A61M 25/0136; A61M 2025/0031; A61M 2210/1082
See application file for complete search history.

(56) References Cited

U.S. PATENT DOCUMENTS 3,749,090 A 7/1973 Stewart
3,830,240 A 8/1974 Antonevich et al.
4,146,300 A 3/1979 Kaiser
4,203,430 A 5/1980 Takahashi
4,215,476 A 8/1980 Armstrong
4,294,233 A 10/1981 Takahashi
4,295,464 A 10/1981 Shihata
4,393,872 A 7/1983 Reznik et al.
4,418,688 A 12/1983 Loeb
4,458,877 A 7/1984 Holmes
4,483,326 A 11/1984 Yamaka et al.
4,519,385 A 5/1985 Atkinson et al.
4,630,598 A 12/1986 Bonnet
4,648,871 A 3/1987 Jacob
4,655,197 A 4/1987 Atkinson
4,662,871 A 5/1987 Rafelson
4,680,026 A 7/1987 Weightman et al.
4,688,555 A 8/1987 Wardle
4,696,669 A 9/1987 Menhusen
4,706,656 A 11/1987 Kuboto
4,708,717 A 11/1987 Deane et al.
4,802,461 A 2/1989 Cho
4,852,551 A 8/1989 Opie et al.
4,874,360 A 10/1989 Goldberg et al.
4,941,872 A 7/1990 Felix et al.
4,950,265 A 8/1990 Taylor
4,995,872 A 2/1991 Ferrara
4,996,974 A 3/1991 Ciarlei
5,057,080 A 10/1991 Takahashi
5,095,889 A 3/1992 Weissmuller et al.
5,120,305 A 6/1992 Boehringer et al.
5,156,142 A 10/1992 Anapliotis et al.
5,186,714 A 2/1993 Boudreault et al.
5,191,881 A 3/1993 Beck
5,226,885 A 7/1993 Takahashi
5,230,704 A 7/1993 Moberg et al.
5,263,938 A 11/1993 Orr et al.
5,265,840 A 11/1993 Gillespie et al.
5,273,524 A 12/1993 Fox et al.
5,281,212 A 1/1994 Savage et al.
5,295,956 A 3/1994 Bales et al.
5,300,043 A 4/1994 Devlin et al.
5,307,803 A 5/1994 Matsuura et al.
5,312,327 A * 5/1994 Bales ...................... A61B 1/12 606/42
5,312,332 A 5/1994 Bales et al.
5,312,400 A 5/1994 Bales et al.
5,314,406 A 5/1994 Arias et al.
5,318,541 A 6/1994 Viera et al.
5,336,172 A 8/1994 Bales et al.
5,336,220 A 8/1994 Ryan et al.
5,350,356 A 9/1994 Bales et al.
5,354,291 A 10/1994 Bales et al.
5,429,596 A 7/1995 Arias et al.
5,476,450 A 12/1995 Ruggio
5,484,402 A 1/1996 Saravia et al.
5,512,035 A 4/1996 Konstorum et al.
5,512,045 A 4/1996 Gurchumelidze
5,549,547 A 8/1996 Cohen et al.
5,579,779 A 12/1996 Humphrey
5,588,634 A 12/1996 Nettekoven
5,607,420 A 3/1997 Schuman
5,609,573 A * 3/1997 Sandock ............ A61B 18/1482 604/35
5,643,304 A 7/1997 Schechter et al.
5,658,258 A 8/1997 Kneer et al.
5,776,096 A 7/1998 Fields
5,827,229 A 10/1998 Auth et al.
5,830,214 A 11/1998 Flom et al.
5,836,909 A 11/1998 Cosmescu
5,885,228 A 3/1999 Rosenman et al.
5,885,288 A 3/1999 Aust et al.
5,944,690 A 8/1999 Falwell et al.
5,961,485 A 10/1999 Martin
5,980,504 A 11/1999 Sharkey et al.
6,066,150 A 5/2000 Gonon
6,129,701 A * 10/2000 Cimino ................. A61M 1/774 604/35
6,168,577 B1 1/2001 Niederjohn et al.
6,179,807 B1 1/2001 Henniges et al.
6,193,672 B1 * 2/2001 Clement ................. A61M 1/85 600/565
6,213,970 B1 4/2001 Nelson et al.
6,328,730 B1 12/2001 Harkrider
6,358,200 B1 3/2002 Grossi
6,471,639 B2 10/2002 Rudischhauser et al.
6,551,281 B1 4/2003 Raulerson et al.
6,623,445 B1 9/2003 Nelson et al.
6,635,028 B1 10/2003 Ielpo et al.
6,645,140 B2 11/2003 Brommersma et al.
6,755,806 B1 6/2004 Von Casimir
6,776,765 B2 8/2004 Soukup et al.
6,827,701 B2 12/2004 MacMahon et al.
6,830,556 B2 12/2004 Harmon et al.
6,857,617 B2 2/2005 Forberg
6,887,221 B1 5/2005 Baillargeon et al.
6,929,236 B1 8/2005 Height et al.
6,932,788 B2 8/2005 Kamiyama et al.
6,939,369 B2 9/2005 Osborne et al.
6,960,189 B2 11/2005 Bates et al.
6,969,368 B2 11/2005 Anspach et al.
6,997,867 B2 2/2006 Soble et al.
7,004,931 B2 2/2006 Hogendijk
7,025,720 B2 4/2006 Boebel et al.
7,179,269 B2 2/2007 Welch et al.
7,249,602 B1 7/2007 Emanuel
7,297,133 B2 11/2007 Nelson et al.
7,465,288 B2 12/2008 Dudney et al.
7,500,947 B2 3/2009 Kucklick et al.
7,503,893 B2 3/2009 Kucklick
7,530,976 B2 5/2009 MacMahon et al.
7,540,868 B2 6/2009 Elliott et al.
7,571,889 B2 8/2009 Miyahara
7,802,574 B2 9/2010 Schultz
7,810,784 B2 10/2010 Abe et al.
7,846,126 B2 12/2010 Steen et al.
7,857,770 B2 12/2010 Raulerson et al.
7,883,516 B2 2/2011 Huang et al.
7,935,049 B2 5/2011 Michel et al.
7,947,039 B2 5/2011 Sartor
7,972,282 B2 7/2011 Clark et al.
8,002,732 B2 8/2011 Vicsonti
8,052,607 B2 11/2011 Byrd
8,062,214 B2 11/2011 Shener et al.
8,118,731 B2 2/2012 Kucklick et al.
8,123,676 B2 2/2012 Kucklick
8,192,500 B2 6/2012 Chung
8,226,548 B2 7/2012 Kucklick
8,241,278 B2 8/2012 Sartor
8,313,081 B2 11/2012 Adelberg
8,353,860 B2 1/2013 Boulais et al.
8,419,626 B2 4/2013 Shener-Irmakoglu et al.

(56) References Cited

U.S. PATENT DOCUMENTS

| | | | | |
|---|---|---|---|---|
| 8,454,536 | B2 | 6/2013 | Raulerson et al. | |
| 8,460,182 | B2 | 6/2013 | Ouyang et al. | |
| 8,475,453 | B2 | 7/2013 | Marczyk et al. | |
| 8,613,735 | B2 | 12/2013 | Omeda et al. | |
| 8,672,928 | B2 | 3/2014 | Liu et al. | |
| 8,702,681 | B2 | 4/2014 | Douglas et al. | |
| 8,721,595 | B2 | 5/2014 | Stiehl et al. | |
| 8,740,773 | B2 | 6/2014 | Kucklick et al. | |
| 8,808,168 | B2 | 8/2014 | Ettwein et al. | |
| 8,845,521 | B2 | 9/2014 | Maruyama | |
| D715,921 | S | 10/2014 | Wan | |
| 8,858,569 | B2 | 10/2014 | Wan | |
| 8,870,748 | B2 | 10/2014 | Kucklick | |
| 8,888,683 | B2 | 11/2014 | Mejia | |
| 8,894,601 | B2 | 11/2014 | Moehle et al. | |
| 8,945,093 | B2 | 2/2015 | Ahluwalia | |
| 9,011,412 | B2 | 4/2015 | Albritton et al. | |
| 9,089,631 | B2 | 7/2015 | Schaeffer et al. | |
| 9,095,646 | B2 | 8/2015 | Chow et al. | |
| 9,095,682 | B2 | 8/2015 | Romoscanu | |
| 9,119,926 | B2 | 9/2015 | Cuevas et al. | |
| 9,138,347 | B2 | 9/2015 | Wiljanen et al. | |
| 9,155,453 | B2 | 10/2015 | Kumar et al. | |
| 9,155,454 | B2 | 10/2015 | Sahney et al. | |
| 9,167,958 | B2 | 10/2015 | Banik et al. | |
| 9,179,968 | B2 | 11/2015 | Leo et al. | |
| 9,186,044 | B2 | 11/2015 | Kucklick et al. | |
| 9,186,055 | B2 | 11/2015 | Kucklick | |
| 9,192,284 | B2 | 11/2015 | Hirsch et al. | |
| 9,204,786 | B2 | 12/2015 | Kucklick | |
| 9,241,612 | B2 | 1/2016 | Hoshino | |
| 9,248,228 | B2 | 2/2016 | Bono et al. | |
| 9,339,631 | B2 | 5/2016 | Graham et al. | |
| 9,358,061 | B2 | 6/2016 | Plascencia et al. | |
| 9,360,124 | B2 | 6/2016 | Schaeffer et al. | |
| 9,387,121 | B2 | 7/2016 | Wiljanen et al. | |
| 9,427,504 | B2 | 8/2016 | Newman | |
| 9,545,334 | B2 | 1/2017 | Steen et al. | |
| 9,572,933 | B2 | 2/2017 | Grannell et al. | |
| 9,622,646 | B2 | 4/2017 | Ouyang et al. | |
| 9,668,643 | B2 | 6/2017 | Kennedy et al. | |
| 9,717,397 | B2 | 8/2017 | Kucklick | |
| 9,743,827 | B2 | 8/2017 | Yasunaga et al. | |
| 9,744,276 | B2 | 8/2017 | Ahluwalia | |
| 9,757,195 | B2 | 9/2017 | Plascencia et al. | |
| 9,775,674 | B2 | 10/2017 | Schaeffer et al. | |
| 9,810,836 | B2 | 11/2017 | Okagami et al. | |
| 9,814,490 | B2 * | 11/2017 | Neoh | A61B 17/3468 |
| 9,820,762 | B2 | 11/2017 | Cadeddu et al. | |
| 9,827,009 | B2 | 11/2017 | Kucklick et al. | |
| 9,833,130 | B2 | 12/2017 | Schaeffer et al. | |
| 9,839,739 | B2 | 12/2017 | Qian | |
| 9,861,788 | B2 | 1/2018 | Yu et al. | |
| 9,878,145 | B2 | 1/2018 | Holm et al. | |
| 9,883,960 | B2 | 2/2018 | Cummins et al. | |
| 9,884,143 | B2 | 2/2018 | Kobida et al. | |
| 9,918,859 | B2 | 3/2018 | Cummins et al. | |
| 9,936,963 | B2 | 4/2018 | Batchelor et al. | |
| 9,968,249 | B2 * | 5/2018 | Huang | A61B 1/0676 |
| 9,974,554 | B2 | 5/2018 | Antonelli et al. | |
| 9,980,631 | B2 | 5/2018 | Schaeffer et al. | |
| 9,982,791 | B2 | 5/2018 | Schaeffer et al. | |
| 10,004,385 | B2 | 6/2018 | Bresco Torras et al. | |
| 10,010,657 | B2 | 7/2018 | Torrance et al. | |
| 10,010,700 | B2 | 7/2018 | Romoscanu | |
| 10,028,763 | B2 | 7/2018 | Kumar et al. | |
| 10,076,432 | B2 | 9/2018 | Cummins et al. | |
| 10,080,578 | B2 * | 9/2018 | Mark | A61B 17/32002 |
| 10,085,624 | B2 | 10/2018 | Isoda et al. | |
| 10,092,173 | B2 | 10/2018 | Dejima | |
| 10,098,768 | B2 | 10/2018 | Cummins et al. | |
| 10,105,247 | B2 | 10/2018 | Cummins et al. | |
| 10,154,919 | B2 | 12/2018 | Cummins et al. | |
| 10,165,933 | B2 | 1/2019 | Dejima | |
| 10,166,013 | B2 | 1/2019 | Nguyen et al. | |
| 10,213,533 | B2 | 2/2019 | Walter | |
| 10,220,123 | B2 | 3/2019 | Monty et al. | |
| 10,231,793 | B2 | 3/2019 | Romo | |
| 10,244,927 | B2 | 4/2019 | Kennedy, II et al. | |
| 10,245,359 | B2 | 4/2019 | Bono et al. | |
| 10,251,539 | B2 | 4/2019 | Sahney et al. | |
| 10,251,671 | B2 | 4/2019 | Dejima | |
| 10,265,056 | B2 | 4/2019 | Stanton et al. | |
| 10,271,716 | B2 | 4/2019 | Ferreira et al. | |
| 10,286,141 | B2 | 5/2019 | Monty et al. | |
| 10,293,105 | B2 | 5/2019 | Panotopoulos | |
| 10,383,656 | B2 | 8/2019 | Raulerson et al. | |
| 10,434,259 | B2 | 10/2019 | Dejima et al. | |
| 10,441,134 | B2 | 10/2019 | Ouyang et al. | |
| 10,441,153 | B2 | 10/2019 | Huang et al. | |
| 10,441,460 | B2 | 10/2019 | Ross et al. | |
| 10,456,519 | B2 | 10/2019 | Ngo-Chu et al. | |
| 10,478,596 | B2 | 11/2019 | Graham et al. | |
| 10,492,662 | B2 | 12/2019 | Govrin et al. | |
| 10,500,323 | B2 | 12/2019 | Huering et al. | |
| 10,507,303 | B2 | 12/2019 | Terwey | |
| 10,531,883 | B1 | 1/2020 | Deville et al. | |
| 10,556,091 | B2 * | 2/2020 | Truhler | A61B 18/1492 |
| 10,561,440 | B2 | 2/2020 | Look et al. | |
| 10,583,272 | B2 | 3/2020 | Yu et al. | |
| 10,595,715 | B2 | 3/2020 | Dejima | |
| 10,596,306 | B2 | 3/2020 | Ahluwalia | |
| 10,610,622 | B2 | 4/2020 | Jeong | |
| 10,624,708 | B2 | 4/2020 | Hunter | |
| 10,625,062 | B2 | 4/2020 | Matlock et al. | |
| 10,694,927 | B2 | 6/2020 | Kucklick | |
| 10,722,253 | B2 | 7/2020 | Deville et al. | |
| 10,722,620 | B2 | 7/2020 | Chuang et al. | |
| 10,758,385 | B2 | 9/2020 | Cummins et al. | |
| 10,765,449 | B2 | 9/2020 | Dejima | |
| 10,842,519 | B2 | 11/2020 | Suh et al. | |
| 10,850,013 | B2 | 12/2020 | Hsu et al. | |
| 10,888,349 | B2 | 1/2021 | Pereira et al. | |
| 10,905,446 | B2 | 2/2021 | Chae | |
| 10,912,873 | B2 | 2/2021 | Nitzan et al. | |
| 10,918,365 | B2 | 2/2021 | Kirkemo | |
| 10,925,666 | B2 | 2/2021 | Plascencia et al. | |
| 10,932,798 | B2 | 3/2021 | Shelton et al. | |
| 10,952,758 | B1 | 3/2021 | Evans | |
| 10,959,868 | B2 | 3/2021 | Cummins et al. | |
| 10,966,737 | B2 | 4/2021 | Nguyen | |
| 10,967,107 | B2 | 4/2021 | Forsberg et al. | |
| 10,980,554 | B2 | 4/2021 | Sperry et al. | |
| 11,013,522 | B2 | 5/2021 | Ciulla | |
| 11,026,715 | B2 | 6/2021 | Mayberry | |
| 11,035,481 | B2 | 6/2021 | Schaeffer et al. | |
| 11,051,678 | B2 | 7/2021 | Nieman | |
| 11,064,869 | B2 * | 7/2021 | McWeeney | A61B 1/018 |
| 11,064,871 | B2 | 7/2021 | Gerbo et al. | |
| 11,076,755 | B2 | 8/2021 | Huang et al. | |
| 11,089,944 | B2 | 8/2021 | Rentschler et al. | |
| 11,090,072 | B2 | 8/2021 | Morey et al. | |
| 11,096,555 | B2 | 8/2021 | Harrah et al. | |
| 11,096,568 | B2 | 8/2021 | Harrah et al. | |
| 11,109,874 | B2 | 9/2021 | Gavala et al. | |
| 11,116,530 | B2 | 9/2021 | Yurek | |
| 11,123,483 | B2 | 9/2021 | Panotopoulos | |
| 11,141,177 | B2 | 10/2021 | Ganz et al. | |
| 11,141,185 | B2 | 10/2021 | Efremkin | |
| 11,167,077 | B2 | 11/2021 | Long et al. | |
| 11,179,520 | B2 | 11/2021 | Farah et al. | |
| 11,185,380 | B2 | 11/2021 | Burbank et al. | |
| 11,241,243 | B2 | 2/2022 | Pereira et al. | |
| 11,241,290 | B2 | 2/2022 | Waterbury et al. | |
| 11,260,928 | B2 | 3/2022 | Taylor | |
| 11,278,300 | B2 | 3/2022 | Bahmanyar et al. | |
| 11,284,912 | B2 | 3/2022 | St. George | |
| 11,284,940 | B2 | 3/2022 | Shelton | |
| 11,324,526 | B2 | 5/2022 | Yurek | |
| 11,330,966 | B2 | 5/2022 | Harrah et al. | |
| 11,357,523 | B2 | 6/2022 | Bionda et al. | |
| 11,382,643 | B2 | 7/2022 | Horowitz et al. | |
| 11,382,650 | B2 | 7/2022 | Noonan et al. | |
| 11,382,652 | B2 | 7/2022 | Wasdyke et al. | |

(56) References Cited

U.S. PATENT DOCUMENTS 11,382,693 B2 7/2022 Harrah et al.
11,399,892 B2 8/2022 Yu et al.
11,419,679 B2 8/2022 Khachaturov et al.
11,433,172 B2 9/2022 Gao et al.
11,452,436 B2 9/2022 Chu et al.
11,452,534 B2 9/2022 Pereira et al.
11,471,175 B2 10/2022 Nguyen et al.
11,471,176 B2 10/2022 Greenhalgh et al.
11,490,912 B2 11/2022 Bonneau et al.
11,490,913 B2 11/2022 Nguyen et al.
11,503,993 B2 11/2022 Chu et al.
11,510,691 B2 11/2022 Nguyen et al.
11,534,190 B2 12/2022 Chu
11,534,249 B2 12/2022 Romo et al.
11,547,479 B2 1/2023 Shelton et al.
11,559,360 B2 1/2023 Romo
11,571,229 B2 2/2023 Shah
11,576,692 B2 2/2023 Gatineau et al.
11,576,853 B2 2/2023 Petkoska et al.
11,577,056 B2 2/2023 Rentschler et al.
11,589,881 B2 2/2023 Horowitz et al.
11,596,423 B2 3/2023 Nguyen et al.
11,602,262 B2 3/2023 Chu
11,602,363 B2 3/2023 Nguyen
11,607,484 B2 3/2023 Hanna et al.
11,653,827 B2 5/2023 Chu et al.
11,672,598 B2 6/2023 Morey et al.
11,672,601 B2 6/2023 Chu et al.
12,329,396 B2 * 6/2025 Tong .................... A61M 3/022
12,329,399 B2 * 6/2025 Tong .................. A61M 3/0233
2003/0199986 A1 10/2003 Mcweeney et al.
2003/0216760 A1 11/2003 Welch et al.
2004/0019358 A1 1/2004 Kear
2004/0143197 A1 7/2004 Soukup et al.
2004/0153095 A1 8/2004 Seddon
2004/0153111 A1 8/2004 Hosoada
2004/0193103 A1 9/2004 Kumar
2004/0236312 A1 11/2004 Nistal et al.
2004/0267213 A1 12/2004 Knapp
2005/0085692 A1 4/2005 Kiehn et al.
2005/0085769 A1 4/2005 MacMahon et al.
2005/0143678 A1 6/2005 Schwarz et al.
2005/0149201 A1 7/2005 Mcweeney et al.
2006/0041186 A1 2/2006 Vancaillie
2006/0069343 A1 3/2006 Rontal
2006/0135948 A1 6/2006 Vrma
2006/0149127 A1 7/2006 Seddiqui et al.
2006/0206004 A1 9/2006 Dehmel et al.
2006/0264995 A1 11/2006 Fanton et al.
2007/0185383 A1 8/2007 Mulhern et al.
2007/0298069 A1 12/2007 Bucay-couto et al.
2008/0004578 A1 1/2008 Nixon et al.
2008/0058588 A1 3/2008 Emanuel
2008/0146991 A1 6/2008 Hernandez et al.
2008/0167526 A1 7/2008 Crank et al.
2008/0167527 A1 7/2008 Slenker et al.
2008/0249483 A1 10/2008 Slenker et al.
2009/0163846 A1 6/2009 Aklog et al.
2009/0187146 A1 * 7/2009 Landman ................ A61M 1/76
606/205
2009/0270894 A1 10/2009 Rubin et al.
2010/0010431 A1 1/2010 Tulley
2010/0056867 A1 3/2010 Labombard et al.
2010/0137846 A1 6/2010 Desai et al.
2010/0305475 A1 12/2010 Hinchliffe et al.
2011/0004197 A1 1/2011 Sansoucy
2011/0060315 A1 3/2011 Windheuser et al.
2011/0202039 A1 8/2011 Schaaf
2011/0224489 A1 9/2011 Deal et al.
2011/0245841 A1 10/2011 Shohat et al.
2012/0041358 A1 2/2012 Mann et al.
2012/0220832 A1 8/2012 Nakade et al.
2013/0024003 A1 1/2013 Mcweeney et al.
2013/0123721 A1 5/2013 Stiehl et al.
2013/0131445 A1 5/2013 Zerfas et al.
2013/0138036 A1 5/2013 Solomon et al.
2013/0165944 A1 6/2013 Gal et al.
2013/0231605 A1 9/2013 Walter
2013/0253387 A1 9/2013 Bonutti et al.
2014/0107565 A1 4/2014 Wiljanen et al.
2014/0171922 A1 6/2014 Douglas et al.
2014/0180010 A1 6/2014 Kumar et al.
2014/0207056 A1 7/2014 Bono et al.
2014/0276207 A1 9/2014 Ouyang et al.
2014/0276377 A1 9/2014 Chang et al.
2014/0288460 A1 9/2014 Ouyang et al.
2014/0296868 A1 10/2014 Garrison et al.
2014/0296894 A1 10/2014 Kojima et al.
2015/0038785 A1 2/2015 Govrin et al.
2015/0141907 A1 5/2015 Clement et al.
2015/0150441 A1 6/2015 Ouyang et al.
2015/0164595 A1 6/2015 Bogusky et al.
2015/0305759 A1 10/2015 St. George et al.
2015/0328394 A1 11/2015 Chow et al.
2016/0001050 A1 1/2016 Yee et al.
2016/0022289 A1 1/2016 Wan
2016/0030070 A1 2/2016 Eisner
2016/0120557 A1 * 5/2016 Goddard ............. A61M 3/0283
606/127
2016/0166320 A1 * 6/2016 Ciulla .................... A61B 18/26
606/14
2016/0270804 A1 9/2016 Honda et al.
2016/0374710 A1 12/2016 Sinelnikov et al.
2016/0374755 A1 12/2016 Mirigian et al.
2017/0027604 A1 2/2017 Wallace
2017/0065752 A1 3/2017 Eisner
2017/0215897 A1 8/2017 Fan
2017/0215899 A1 8/2017 Harrah et al.
2017/0215964 A1 8/2017 Harrah et al.
2017/0215965 A1 8/2017 Harrah et al.
2017/0252051 A1 9/2017 Wan et al.
2017/0252103 A1 9/2017 Griefeneder et al.
2017/0258550 A1 9/2017 Vazales
2017/0266046 A1 9/2017 Steen et al.
2017/0303940 A1 10/2017 Sperry et al.
2017/0303941 A1 10/2017 Eisner
2017/0319776 A1 11/2017 Eisner
2017/0333614 A1 11/2017 Gao et al.
2017/0340862 A1 11/2017 Calabrese et al.
2017/0354431 A1 12/2017 Rubin et al.
2018/0055568 A1 3/2018 Shelton et al.
2018/0206866 A1 7/2018 Wan
2018/0360480 A1 12/2018 Ciulla
2019/0038817 A1 2/2019 Forsberg et al.
2019/0059988 A1 2/2019 Davison et al.
2019/0099209 A1 4/2019 Witt et al.
2019/0192222 A1 6/2019 Mirigian et al.
2019/0274699 A1 9/2019 Morey et al.
2019/0290811 A1 9/2019 Bono et al.
2019/0314044 A1 10/2019 Long et al.
2019/0328412 A1 10/2019 Mazhar et al.
2019/0343586 A1 11/2019 Bonneau et al.
2019/0357762 A1 11/2019 Clayman et al.
2020/0009302 A1 1/2020 Pyle
2020/0046393 A1 2/2020 Kendale et al.
2020/0069319 A1 3/2020 Harrah et al.
2020/0147294 A1 5/2020 Edwards
2020/0178767 A1 6/2020 Miller
2020/0178773 A1 6/2020 Miller
2020/0188014 A1 6/2020 Woloszko et al.
2020/0196843 A1 6/2020 Tah et al.
2020/0229907 A1 7/2020 Duehlmeier
2020/0289722 A1 * 9/2020 Culbert ............... A61M 25/007
2020/0297362 A1 9/2020 Deville et al.
2020/0397507 A1 12/2020 Liu
2020/0397975 A1 12/2020 Kirk et al.
2021/0015507 A1 1/2021 Roberts et al.
2021/0015509 A1 1/2021 Wan
2021/0022756 A1 1/2021 Ciulla
2021/0022757 A1 1/2021 Wan
2021/0022759 A1 1/2021 Wan
2021/0076904 A1 3/2021 Calabrese et al.
2021/0084766 A1 3/2021 Govrin
2021/0085158 A1 3/2021 Ikuma et al.

(56) References Cited

U.S. PATENT DOCUMENTS

| | | | |
|---|---|---|---|
| 2021/0093338 A1 | 4/2021 | Baker et al. | |
| 2021/0093340 A1 | 4/2021 | Baker et al. | |
| 2021/0093341 A1 | 4/2021 | Baker et al. | |
| 2021/0113268 A1 | 4/2021 | Waisman et al. | |
| 2021/0121188 A1 | 4/2021 | Yurek | |
| 2021/0177444 A1 | 6/2021 | Shelton et al. | |
| 2021/0178032 A1 | 6/2021 | Hsu et al. | |
| 2021/0228274 A1 | 7/2021 | Pyro et al. | |
| 2021/0236204 A1 | 8/2021 | Tower et al. | |
| 2021/0275248 A1 | 9/2021 | Pyro et al. | |
| 2021/0307589 A1 | 10/2021 | Rentschler et al. | |
| 2021/0315595 A1 | 10/2021 | Crawford et al. | |
| 2021/0315608 A1 | 10/2021 | Mozloom, Jr. | |
| 2021/0321861 A1 | 10/2021 | McWeeney et al. | |
| 2021/0322040 A1 | 10/2021 | Gavala et al. | |
| 2021/0330309 A1 | 10/2021 | Ma et al. | |
| 2021/0338064 A1 | 11/2021 | Fitterer et al. | |
| 2021/0338257 A1 | 11/2021 | Morey et al. | |
| 2021/0361356 A1 | 11/2021 | Shelton et al. | |
| 2021/0369095 A1 | 12/2021 | Stem et al. | |
| 2021/0378740 A1 | 12/2021 | Chu et al. | |
| 2021/0386273 A1 | 12/2021 | Purohit et al. | |
| 2022/0000508 A1 | 1/2022 | Schmitt et al. | |
| 2022/0022912 A1 | 1/2022 | Efremkin et al. | |
| 2022/0023528 A1 | 1/2022 | Long et al. | |
| 2022/0023563 A1 | 1/2022 | Ganz et al. | |
| 2022/0031392 A1 | 2/2022 | Maher et al. | |
| 2022/0047283 A1 | 2/2022 | Baker et al. | |
| 2022/0047287 A1 | 2/2022 | Stender et al. | |
| 2022/0047332 A1 | 2/2022 | Schmitt et al. | |
| 2022/0053995 A1 | 2/2022 | Knollman et al. | |
| 2022/0053998 A1 | 2/2022 | Ghani et al. | |
| 2022/0054162 A1 | 2/2022 | Efremkin | |
| 2022/0061827 A1 | 3/2022 | Schmitt et al. | |
| 2022/0061866 A1 | 3/2022 | Crawford et al. | |
| 2022/0072213 A1 | 3/2022 | Thoreson | |
| 2022/0087697 A1 | 3/2022 | Yurek | |
| 2022/0087698 A1* | 3/2022 | Yurek | A61B 17/22 |
| 2022/0096108 A1 | 3/2022 | Baker et al. | |
| 2022/0104839 A1 | 4/2022 | Horowitz et al. | |
| 2022/0104840 A1 | 4/2022 | Horowitz et al. | |
| 2022/0133340 A1 | 5/2022 | Schaeffer et al. | |
| 2022/0135171 A1 | 5/2022 | Taylor | |
| 2022/0142463 A1 | 5/2022 | Altshuler et al. | |
| 2022/0142659 A1 | 5/2022 | Melsheimer et al. | |
| 2022/0168003 A1 | 6/2022 | Crowley | |
| 2022/0183706 A1 | 6/2022 | Pereira et al. | |
| 2022/0202285 A1 | 6/2022 | Bukesov et al. | |
| 2022/0218367 A1 | 7/2022 | Ghani et al. | |
| 2022/0218416 A1 | 7/2022 | Vogel | |
| 2022/0226016 A1 | 7/2022 | Ganz et al. | |
| 2022/0233199 A1 | 7/2022 | Du et al. | |
| 2022/0240761 A1 | 8/2022 | Harrah et al. | |
| 2022/0240762 A1 | 8/2022 | Rentschler et al. | |
| 2022/0265350 A1 | 8/2022 | Clayman et al. | |
| 2022/0273860 A1 | 9/2022 | Wiener et al. | |
| 2022/0280021 A1 | 9/2022 | Chu | |
| 2022/0287774 A1 | 9/2022 | Ikuma et al. | |
| 2022/0287775 A1 | 9/2022 | Harrah et al. | |
| 2022/0296300 A1 | 9/2022 | Takata | |
| 2022/0304548 A1 | 9/2022 | Chu | |
| 2022/0313290 A1 | 10/2022 | Obermiller et al. | |
| 2022/0323153 A1 | 10/2022 | Yu et al. | |
| 2022/0338891 A1 | 10/2022 | Johnson et al. | |
| 2022/0354520 A1 | 11/2022 | Mannion et al. | |
| 2022/0362449 A1 | 11/2022 | Gao et al. | |
| 2022/0362511 A1 | 11/2022 | Gavalis et al. | |
| 2022/0369906 A1 | 11/2022 | Wilson et al. | |
| 2022/0369919 A1 | 11/2022 | Chu et al. | |
| 2022/0370085 A1 | 11/2022 | Reagan, Jr. et al. | |
| 2022/0370127 A1 | 11/2022 | Khachaturov et al. | |
| 2022/0386852 A1 | 12/2022 | Chu et al. | |
| 2022/0387534 A1 | 12/2022 | Petkoska | |
| 2022/0401119 A1 | 12/2022 | Pereira et al. | |
| 2023/0028334 A1 | 1/2023 | Aljure | |
| 2023/0030708 A1 | 2/2023 | Noonan et al. | |
| 2023/0031136 A1 | 2/2023 | Ikuma | |
| 2023/0055911 A1 | 2/2023 | Chu et al. | |
| 2023/0063701 A1 | 3/2023 | Horowitz et al. | |
| 2023/0066304 A1 | 3/2023 | Nguyen et al. | |
| 2023/0075988 A1 | 3/2023 | Scheib et al. | |
| 2023/0081712 A1 | 3/2023 | Shelton et al. | |
| 2023/0083127 A1 | 3/2023 | Hayashi et al. | |
| 2023/0103647 A1 | 4/2023 | Nguyen et al. | |
| 2023/0113437 A1* | 4/2023 | Horie | A61B 1/00094 600/159 |
| 2023/0113650 A1 | 4/2023 | Sasaguchi | |
| 2023/0115997 A1 | 4/2023 | Sato et al. | |
| 2023/0125143 A1 | 4/2023 | Schmitt | |
| 2023/0130679 A1 | 4/2023 | Avolos | |
| 2023/0130759 A1 | 4/2023 | Shelton | |
| 2023/0131637 A1 | 4/2023 | Shelton et al. | |
| 2023/0145569 A1 | 5/2023 | McWeeney et al. | |
| 2023/0146163 A1* | 5/2023 | Yurek | A61B 17/22 606/127 |
| 2023/0146598 A1 | 5/2023 | Yurek | |
| 2023/0148845 A1 | 5/2023 | McWeeney et al. | |
| 2023/0165599 A1 | 6/2023 | Nguyen et al. | |
| 2023/0181011 A1 | 6/2023 | Chu | |
| 2023/0181203 A1 | 6/2023 | Nguyen et al. | |
| 2023/0181204 A1 | 6/2023 | Shah | |
| 2023/0190078 A1 | 6/2023 | Clayman et al. | |
| 2023/0190316 A1 | 6/2023 | Nguyen | |
| 2023/0190317 A1 | 6/2023 | Horowitz et al. | |
| 2023/0190373 A1 | 6/2023 | Hutchens et al. | |
| 2023/0210586 A1 | 7/2023 | Mantri et al. | |
| 2023/0263369 A1 | 8/2023 | Chu et al. | |
| 2023/0263571 A1 | 8/2023 | Chu et al. | |
| 2023/0301718 A1 | 9/2023 | Harrah et al. | |
| 2023/0346202 A1 | 11/2023 | Harrah et al. | |
| 2024/0057855 A1 | 2/2024 | Reed et al. | |
| 2024/0099563 A1 | 3/2024 | Wales et al. | |
| 2024/0130743 A1 | 4/2024 | Hajjar | |
| 2024/0138666 A1 | 5/2024 | Chu et al. | |
| 2024/0138913 A1 | 5/2024 | Carlson et al. | |
| 2024/0148394 A1 | 5/2024 | Baker et al. | |
| 2024/0358911 A1* | 10/2024 | Eisner | A61M 1/77 |
| 2025/0099167 A1* | 3/2025 | Pham | A61B 18/1492 |

FOREIGN PATENT DOCUMENTS

| | | |
|---|---|---|
| CN | 203988361 U | 12/2014 |
| KR | 10-2167406 B1 | 10/2020 |
| WO | WO 2010/068467 A1 | 6/2010 |
| WO | WO 2014/160201 A1 | 10/2014 |
| WO | WO 2017/135980 A1 | 8/2017 |
| WO | WO 2018/215954 A1 | 11/2018 |
| WO | WO 2019/178387 A1 | 9/2019 |
| WO | WO 2020/146454 A1 | 7/2020 |
| WO | WO 2020/150713 A2 | 7/2020 |
| WO | WO 2020/247103 A1 | 12/2020 |

OTHER PUBLICATIONS

Non-Final Office Action dated Apr. 28, 2023 for U.S. Appl. No. 18/090,802; 29 pages.

Communication dated Oct. 26, 2021 forwarding the extended European Search Report for European Patent Application No. 19746731.9; 12 pages.

Chew, et al., "Natural History, Complications and Re-Intervention Rates of Asymptomatic Residual Stone Fragments after Ureteroscopy: a Report from the EDGE Research Consortium", The Journal of Urology; Apr. 2016 (published online Nov. 2015); vol. 195, pp. 982-986.

Deng, et al., "Suctioning flexible ureteroscopy with automatic control of renal pelvic pressure: a porcine model", International Journal of Clinical and Experimental Medicine, Mar. 30, 2016.

Deng, et al., "A Novel Flexible Ureteroscopy with Intelligent Control of Renal Pelvic Pressure: An Initial Experience of 93 Cases", Journal of Endourology; Oct. 2016 (published online Aug. 2016); vol. 30(10), pp. 1067-1072.

(56) References Cited

OTHER PUBLICATIONS

Emmott, et al., "Complications, Re-Intervention Rates, and Natural History of Residual Stone Fragments After Percutaneous Nephrolithotomy", Journal of Endourology; Jan. 2018; vol. 32(1), pp. 28-32.
Huang, et al., "Endourology and Stones | The Application of Suctioning Flexible Ureteroscopy With Intelligent Pressure Control in Treating Upper Urinary Tract Calculi on Patients With a Solitary Kidney", Urology Jan. 2018; vol. 111, pp. 44-47.
Kim, et al., "The Clinical Efficacy of Dual-Lumen Catheter Technique in Retrograde Intrarenal Surgery for the Management of Nephrolithiasis: A Propensity Score Analysis", Journal of Endourology; Dec. 2018; vol. 32(12).
Leveillee, et al., "Impressive Performance: New Disposable Digital Ureteroscope Allows for Extreme Lower Pole Access and Use of 365 μm Holmium Laser Fiber", Journal of Endourology Case Reports; Jun. 1, 2016; vol. 2(1), pp. 114-116.
Li, et al., "A Novel Semirigid Ureterorenoscope with Vacuum Suctioning System for Management of Single Proximal Ureteral and Renal Pelvic Stones: An Initial Experience", Journal of Endourology; Dec. 2018; vol. 32(12), pp. 1154-1159.
Peng, et al., "Suctioning flexible ureteroscopic lithotripsy in the oblique supine lithotomy position and supine lithotomy position: a comparative retrospective study", Minerva Urologica e Nefrologica, Dec. 2018; vol. 70(6), pp. 612-616.
Portis, et al., "Endourology and Stones | Repeat Surgery After Ureteroscopic Laser Lithotripsy With Attempted Complete Extraction of Fragments: Long-term Follow-up", Urology Jun. 2015; vol. 85(6), pp. 1272-1278.
Raman, et al., "Natural History of Residual Fragments Following Percutaneous Nephrostolithotomy", Journal of Urology Mar. 2009; vol. 181(3), pp. 1163-1168.
Rebuck, et al., "Endourology and Stones | The Natural History of Renal Stone Fragments Following Ureteroscopy", Urology Mar. 2011; vol. 77(3), pp. 564-568.
Scales, et al., "The impact of unplanned postprocedure visits in the management of patients with urinary stones", Surgery May 2014; vol. 155(5), pp. 769-775.
Skolarikos, et al., "Urolithiasis/Endourology | Outcomes of Flexible Ureterorenoscopy for Solitary Renal Stones in the CROES URS Global Study", Journal of Urology Jul. 2015; vol. 194(1), pp. 137-143.
Villanueva, et al., "Silicone Catheters May Be Superior to Latex Catheters in Difficult Urethral Catheterization After Urethral Dilation", Journal of Endourology 2011, vol. 25(5), pp. 841-844.
Zeng, et al., "Modified Access Sheath for Continuous Flow Ureteroscopic Lithotripsy: A Preliminary Report of a Novel Concept and Technique", Journal of Endourology Sep. 2016; vol. 30(9), pp. 992-996.
Ali, et al: "Retrograde Cystonephroscopy for Complex Renal Calculi Using Novel Dual-Action Aspiration, Irrigation Cystoscope: Initial Case Series", Journal of Endourology; Jul. 2022; vol. 36 (7); pp. 898-905.
Chen, et al: "The Comparison Study of Flexible Ureteroscopic Suctioning Lithotripsy With Intelligent Pressure Control Versus Minimally Invasive Percutaneous Suctioning Nephrolithotomy in Treating Renal Calculi of 2 to 3 cm in Size", Surgical Innovation 2019; vol. 26(5); pp. 528-535.
Jiang, et al: "Ex Vivo Renal Stone Dusting: Impact of Laser Modality, Ureteral Access Sheath, and Suction on Total Stone Clearance", Journal of Endourology; Apr. 2022; vol. 36(4); pp. 499-507.
Karani, et al: "Evaluation of a Novel Female Gender Flexible Ureteroscope: Comparison of Flow and Deflection to a Standard Flexible Ureteroscope", Journal of Endourology; Jun. 2021; vol. 35(6); pp. 840-846.
Keller, et al: "Next-Generation Fiberoptic and Digital Ureteroscopes", Urol Clin North Am.; May 2019; vol. 46(2); pp. 147-163.
Lai, et al: "RIRS with Vacuum-Assisted Ureteral Access Sheath versus MPCNL for the Treatment of 2-4cm Renal Stone", BioMed Research International 2020; vol. 2020, Article ID 8052013, 8 pages.
Schneider, et al: "In Vitro Evaluation of Stone Fragment Evacuation by Suction", Journal of Endourology; Feb. 2021; vol. 35(2); pp. 187-191.
Williams, et al: "The Fluid Mechanics of Ureteroscope Irrigation", Journal of Endourology; Jan. 2019; vol. 33(1); pp. 28-34.
Williams, et al: "A lumped-parameter model for kidney pressure during stone removal," IMA Journal of Applied Mathematics; Oct. 2020; vol. 85(5); pp. 703-723.
Williams, et al: "Cavity Flow Characteristics and Applications to Kidney Stone Removal," Journal of Fluid Mechanics 2020; vol. 902; A16.
Williams, et al: "Effects of Geometry on Resistance in Elliptical Pipe Flows," Journal of Fluid Mechanics 2020; vol. 891; A4-1.
Williams, et al: "Shape optimisation for faster washout in recirculating flows," Journal of Fluid Mechanics 2021; vol. 914; A37.
Zanetti, et al: "Vacuum-assisted mini-percutaneous nephrolithotomy: a new perspective in fragments clearance and intrarenal pressure control", World Journal of Urology 2021; vol. 39; pp. 1717-1723.
Non-final office action mailed Aug. 9, 2023 for U.S. Appl. No. 16/966,856; 40 pages.
Non-final office action mailed Aug. 9, 2023 for U.S. Appl. No. 17/489,723; 25 pages.
Non-final office action mailed Aug. 9, 2023 for U.S. Appl. No. 18/091,308; 27 pages.
Invitation To Pay Additional Fees And, Where Applicable, Protest Fee mailed May 24, 2023 for International Patent Application No. PCT/US2023/014276; 14 pages.
International Search Report and Written Opinion mailed Jul. 31, 2023 for International Patent Application No. PCT/US2023/014276; 60 pages.
Final Office Action dated Aug. 25, 2023 for U.S. Appl. No. 18/090,802; 29 pages.

* cited by examiner

FLOW CONTROL MECHANISM FOR KIDNEY STONE TREATMENT SYSTEM

CROSS-REFERENCE

This application claims priority to and the benefit of provisional application Ser. No. 63/357,468, filed Jun. 30, 2022, which is incorporated herein by reference.

FIELD

The present inventions generally relate to systems, devices, and methods for removal of objects in vivo; and more particularly to mechanisms for irrigation and removal of objects, such as kidney stones.

BACKGROUND

Kidney stones are a common medical problem that negatively impacts millions of individuals worldwide. Kidney stones include one or more solid masses of material that are usually made of crystals and form in parts of the urinary tract including in the ureter, the kidney, and/or the bladder of the individual. Kidney stones range in size from small (less than about 1 cm) to very large (more than 4 cm) and may cause significant pain to the individual and damage to the kidney. The overwhelming majority of stones that are treated by surgeons are less than 1 cm.

The recommended treatment for removal of kidney stones varies according to numerous factors including the size of the kidney stones, the number of kidney stones, and the location of the kidney stones. The most common treatments for kidney stones are shock wave lithotripsy (ultrasound waves used to fracture the stones), ureteroscopy (fracture and removal of the stones using an endoscope that is introduced through the bladder), and percutaneous nephrolithotomy (fracture and removal of the stones using an endoscope that is introduced through a sheath placed through the patient's back into the kidney).

The largest kidney stones are usually removed through percutaneous nephrolithotomy or nephrolithotripsy. In these procedures, a small incision is made through the patient's back adjacent the kidney and a sheath is passed into the kidney to accommodate a larger endoscope used to fracture and remove stones. The stone may be removed directly through the tube or may be broken up into small fragments while still in the patient's body and then removed via a vacuum or other known methods.

There are numerous drawbacks associated with nephrolithotomy, nephrolithotripsy, and other invasive surgeries requiring an incision in the skin. Namely, such surgical techniques may require significantly more anesthesia administered to the patient, the surgeries are more complicated and pose a higher risk of infection and complications for the patient, and the surgeries require a substantial incision in the patient, which may leave a scar. Additionally, given the invasiveness of the procedure, percutaneous procedures are usually not preferred for smaller kidney stones (e.g., less than 1 cm) depending on the size and location of the stones.

Traditionally, smaller kidney stones have been treated using less invasive techniques including through ureteroscopy. In ureteroscopy, the surgeon typically inserts a ureteroscope into the urethra, through the bladder, and the ureter to provide the surgeon with a direct visualization of the kidney stones which may reside in the ureter or kidney. The surgeon then removes the kidney stone directly using a basketing device if the kidney stone is small enough to pass through the urinary tract without difficulty, or the surgeon fractures the kidney stone into smaller pieces using a laser or other breaking device. A laser lithotripsy device is inserted through the ureteroscope and is used to fragmentize the larger kidney stones into smaller pieces. After breaking the kidney stone into smaller pieces, the surgeon removes the laser or breaking device and inserts a basket or an extraction catheter to capture the kidney stone fragments under the direct visualization of the ureteroscope. Upon retrieving some of the kidney stone fragments, the surgeon removes the basket from the patient and empties the kidney stone fragments therefrom. This process is repeated until clinically significant kidney stones and kidney stone fragments are broken up and removed from the body.

It should be apparent that this process is extremely time consuming, costly, and inefficient because the surgeon is required to insert and remove the scope and basket into and out of the patient many times to completely remove the kidney stones and kidney stone fragments. Using a basket removal device to capture kidney stones or kidney stone fragments suffers from other drawbacks in that the basket is difficult to position adjacent the kidney stone fragments and maneuver in a manner that effectively retrieves the fragments. The training required for such a procedure is not insignificant and the basket removal technique can be difficult for even the most skilled surgeons. Additionally, the surgeon is susceptible to hand fatigue due to the extended amount of time required to operate the kidney stone retrieval baskets. Further, the patient is required to be under local anesthesia and/or remain immobile over an extended amount of time. Still further, the basket retrieval devices cause irritation to the urinary tract due to the repeated insertion and removal.

Thus, there is an unmet need for new devices and methods that permit minimally invasive removal of kidney stones.

SUMMARY

In accordance with one aspect of the invention, a removably insertable medical device is provided. The medical device is capable of application of an irrigation fluid and vacuum and comprises an elongated tubular body comprising an irrigation lumen for application of an irrigation fluid, and a vacuum lumen for application of vacuum suction. A handle mechanism is connected to the elongated tubular body. The handle mechanism is configured to be operated by a user for application of the irrigation fluid and vacuum. The handle mechanism comprises the following modes of action:

- (a) passive irrigation off/active irrigation off/active vacuum off,
- (b) passive irrigation on/active irrigation on/active vacuum on,
- (c) passive irrigation on/active irrigation on/active vacuum off
- (d) passive irrigation off/active irrigation off/active vacuum on,
- (e) passive irrigation on/active irrigation off/active vacuum off,
- (f) passive irrigation on/active irrigation off/active vacuum on,
- (g) passive irrigation off/active irrigation on/active vacuum off, and
- (h) passive irrigation off/active irrigation on/active vacuum on.

The level of active irrigation and active vacuum can be adjustable. The level of passive irrigation can be adjustable. In some embodiments, the levels of active irrigation and active vacuum can each be independently adjustable, and optionally the level of passive irrigation can be independently adjustable.

In one embodiment, the modes of action comprise:

(a) passive irrigation off/active irrigation off/passive vacuum off/active vacuum off,
(b) passive irrigation on/active irrigation off/passive vacuum off/active vacuum off,
(c) passive irrigation on/active irrigation off/passive vacuum on/active vacuum off,
(d) passive irrigation on/active irrigation on/passive vacuum off/active vacuum off,
(e) passive irrigation on/active irrigation on/passive vacuum on/active vacuum off,
(f) passive irrigation on/active irrigation on/passive vacuum on/active vacuum on,
(g) passive irrigation off/active irrigation off/passive vacuum on/active vacuum on,
(h) passive irrigation on/active irrigation on/passive vacuum off/active vacuum on,
(i) passive irrigation on/active irrigation off/passive vacuum off/active vacuum on,
(j) passive irrigation off/active irrigation off/passive vacuum on/active vacuum off, and
(k) passive irrigation off/active irrigation off/passive vacuum off/active vacuum on.

In an embodiment, the level of passive vacuum can be adjustable. In one embodiment the level of active irrigation, passive irrigation, active vacuum, and/or passive vacuum can each be independently adjustable.

In an embodiment, the insertable medical device can be a kidney stone removal mechanism with the vacuum lumen configured to remove a kidney stone or a fragmented kidney stone.

In an embodiment, the level of active and passive irrigation is adjustable by manipulating the irrigation lumen or a secondary lumen in communication with the irrigation lumen. A device for manipulating can comprise:

(a) a pressing element configured to removably apply a force against an outer side of the irrigation or secondary lumen to cause the progressive narrowing of an inner channel of the lumen at a part where the pressing element is forced against the lumen;
(b) a piston-type valve operable within a valve cylinder, the valve having apertures configured to communicate with the irrigation or secondary lumen;
(c) a plunger shaft configured to bias back-and-forth in a cylindrical housing, the cylindrical housing having apertures configured to communicate with the irrigation or secondary lumen;
(d) a component configured to pinch the irrigation or secondary lumen to cause narrowing of an inner channel of the lumen at a part where the component pinches the lumen;
(e) a pair of plates such that one plate is rotatable with respect to the other plate, each of the plates having apertures configured to communicate with the irrigation or secondary lumen when at least one of the apertures of the one plate is aligned with respect to an aperture of the other plate; or
(f) a stop component configured to progressively close and open an opening of the irrigation or secondary lumen.

In one embodiment, the level of active and passive vacuum is adjustable by manipulating the vacuum lumen or a secondary lumen in communication the vacuum lumen. A device for manipulating can comprise:

(a) a pressing element configured to removably apply a force against an outer side of the vacuum or secondary lumen to cause the progressive narrowing of an inner channel of the lumen at a part where the pressing element is forced against the lumen;
(b) a piston-type valve operable within a valve cylinder, the valve having apertures configured to communicate with the vacuum or secondary lumen;
(c) a plunger shaft configured to bias back-and-forth in a cylindrical housing, the cylindrical housing having apertures configured to communicate with the vacuum or secondary lumen;
(d) a component configured to pinch the vacuum or secondary lumen to cause narrowing of an inner channel of the lumen at a part where the component pinches the lumen;
(e) a pair of plates such that one plate is rotatable with respect to the other plate, each of the plates having apertures configured to communicate with the vacuum or secondary lumen when at least one of the apertures of the one plate is aligned with respect to an aperture of the other plate; or
(f) a stop component configured to progressively close and open an opening of the vacuum or secondary lumen.

In one embodiment, the insertable medical device is a kidney stone removal mechanism, and wherein the handle comprises a trigger operable by a user, the actuation of which causes selective constriction and un-constriction of a lumen configured for active application of the irrigation fluid. The actuation of the trigger can also cause selective constriction and un-constriction of a lumen configured for active application of the vacuum such that the constriction and un-constriction of the lumen configured for the active application of the vacuum occurs simultaneously with the constriction and un-constriction of the lumen configured for the active application of the irrigation fluid.

The insertable medical device can be a kidney stone removal mechanism, and wherein the handle comprises a trigger operable by a user, the actuation of which causes concurrent and progressive adjustment of the level applied irrigation fluid and vacuum. The handle mechanism can comprise a component that indicates to a user the degree at which the trigger is actuated. The handle mechanism can have resilient device that interacts with the trigger to cause the trigger to return to a home position in response to user release of the trigger.

In an embodiment, the elongated tubular body can be a catheter connected to the handle mechanism, wherein the handle mechanism additionally comprises a steering mechanism for steering a distal tip of the catheter to facilitate insertion and navigation of the catheter through a bodily passageway and removal of a debris by vacuum.

In an embodiment, a flow indicator can be in communication with at least one of a lumen configured for the active and/or passive application of the irrigation fluid; or a lumen configured for the active and/or passive application of vacuum. In an embodiment, the insertable medical device is a kidney stone removal mechanism and wherein the kidney stone removal mechanism comprises a stone catcher in communication with the vacuum lumen.

In accordance with one aspect, a removably insertable medical device is provided capable of simultaneous application of an irrigation fluid and vacuum. The device comprises an elongated tubular body comprising an irrigation lumen for application of an irrigation fluid, and a vacuum lumen for application suction; and a handle mechanism connected to the elongated tubular body, the handle mechanism comprising a single control mechanism configured to be operated by a user for regulating the rate or amount of applied irrigation fluid and vacuum, wherein the operation of the single control mechanism regulates the levels of applied irrigation fluid and suction with respect to each other.

In an embodiment, the single control mechanism simultaneously constricts and un-constricts a first lumen configured for application of irrigation fluid and a second lumen configured for application of vacuum. The single control mechanism can be a trigger than can be pressed by a user and return back in response to the user releasing the trigger. The device can be a kidney stone removal device.

In accordance with another aspect of the invention, a kidney stone removal mechanism is provided. The mechanism comprises an irrigation tube; a vacuum tube; and a trigger mechanism. The trigger mechanism includes a trigger operable by a user. The trigger can be located at a proximal end of the kidney stone removal mechanism. The trigger mechanism can be operable to selectively constrict, close, and open the irrigation tube to irrigate an area of treatment upon user operation of the trigger, and to selectively initiate vacuum within the vacuum tube to remove partial or entire kidney stones upon user operation of the trigger. A user depression of the trigger can progressively open the irrigation tube. In an embodiment, the trigger comprises a first protrusion, such that a user operation of the trigger causes the first protrusion to selectively constrict, close, and open the irrigation tube. The user depression of the trigger can cause the first protrusion to progressively open the irrigation tube. In an embodiment, the trigger can comprise a second protrusion, such that a user depression of the trigger causes the second protrusion to selectively initiate vacuum within the vacuum tube. The user depression of the trigger can cause the second protrusion to progressively initiate vacuum within the vacuum tube. The kidney stone removal mechanism can further comprise a catheter connected at its proximal end to a distal end of the kidney stone removal mechanism. The catheter has a distal tip at a distal end of the catheter. A steering mechanism can be located at the proximal end of the kidney stone removal mechanism. The steering mechanism is operable to steer the distal tip to facilitate removal of partial or entire kidney stones. The steering mechanism can comprise at least one wire, connected between the steering mechanism and the catheter, to move the distal tip to a desired location to facilitate removal of partial or entire kidney stones.

The first protrusion can comprise a roller. The second protrusion can comprise a roller. The trigger can comprise a third protrusion and the trigger mechanism can comprise a first detent that is selectively engageable with the third protrusion, to alert the user to a predetermined amount of depression of the trigger. The first detent can comprise an edge of a protrusion inside the trigger mechanism or can comprise an edge of a depression inside the trigger mechanism. The third protrusion of the trigger can comprise a roller. The kidney stone removal mechanism can further comprise a second detent to alert the user to a full amount of depression of the trigger. The second detent can comprise a protrusion inside the trigger mechanism. The second detent can comprise an opposite edge of the depression inside the trigger mechanism. The roller can engage with the opposite edge of the depression to alert the user to a full amount of depression of the trigger.

In accordance with an embodiment, the trigger mechanism can be located at the proximal end of the kidney stone removal mechanism so as to be operable by a user's thumb. The trigger mechanism can be located at the proximal end of the kidney stone removal mechanism so as to be operable by a user's finger. The steering mechanism can be located at the proximal end of the kidney stone removal mechanism so as to be operable by a user's thumb.

In accordance with an embodiment, the kidney stone removal mechanism further comprises a resilient device that interacts with the trigger mechanism to cause the trigger mechanism to return to a home position in response to user release of the trigger. The resilient device can comprise a spring.

In accordance with an embodiment, the kidney stone removal mechanism further comprises a vacuum activation tube connected to the vacuum tube. The second protrusion can initiate vacuum within the vacuum tube by pinching the vacuum activation tube shut. The second protrusion can initiate vacuum within the vacuum tube by covering a port of the vacuum activation tube.

In accordance with an aspect of the invention, a kidney stone removal mechanism is provided comprising an irrigation tube configured carry fluid and having a portion passing within a trigger mechanism and a bypass structure connected in two places with the irrigation tube and configured to allow fluid to flow from a first part of the irrigation tube to a second part of the irrigation tube without passing through the portion of the irrigation tube within the trigger mechanism. The trigger mechanism includes a trigger operable by a user. The trigger mechanism can be operable to selectively constrict, close, and open the first irrigation tube to irrigate an area of treatment upon user operation of the trigger. The bypass structure can comprise a flow restriction. A user depression of the trigger can progressively open the irrigation tube. The kidney stone removal mechanism can further comprise a vacuum tube configured to be activated by the trigger mechanism. The kidney stone removal mechanism can further comprise a catheter connected at its proximal end to a distal end of the kidney stone removal mechanism, the catheter having a distal tip at a distal end of the catheter, and a steering mechanism, located at the proximal end of the kidney stone removal mechanism, the steering mechanism operable to steer the distal tip to facilitate removal of partial or entire kidney stones.

In accordance with another aspect of the invention, a kidney stone removal mechanism is provided comprising an irrigation tube; a vacuum tube; and a flow indicator mechanism including a flow indicator connected to a stone catcher assembly. In an embodiment, the flow indicator can comprise one or more vanes that move in response to fluid or air flow. The kidney stone removal mechanism can further comprise a catheter connected at its proximal end to a distal end of the kidney stone removal mechanism, the catheter having a distal tip at a distal end of the catheter, and a steering mechanism, located at the proximal end of the kidney stone removal mechanism, the steering mechanism operable to steer the distal tip to facilitate removal of partial or entire kidney stones.

In accordance with another aspect of the invention, a method of kidney stone removal with the use of all of the embodiments of the present inventions is provided. In accordance with an aspect of the invention, methods of kidney stone removal are provided comprising operating kidney stone removal mechanisms as described above and herein.

BRIEF DESCRIPTION OF THE DRAWINGS

Aspects of the present invention now will be described in detail with reference to the accompanying drawings, which are not drawn to scale.

DESCRIPTION

Disclosed herein are systems, devices, and methods for the guided removal of objects in vivo. In particular, the systems, devices, and methods may be adapted to traverse compact areas, such as the urinary tract, and to remove debris, such as kidney stones or fragments of kidney stones, via aspiration through a vacuum tube. As used herein, the term "kidney stones" may refer to fragments of kidney stones, including fragments that have been created by therapeutic fracturing of kidney stones, such as with the device described herein or by another device.

Figure 1:
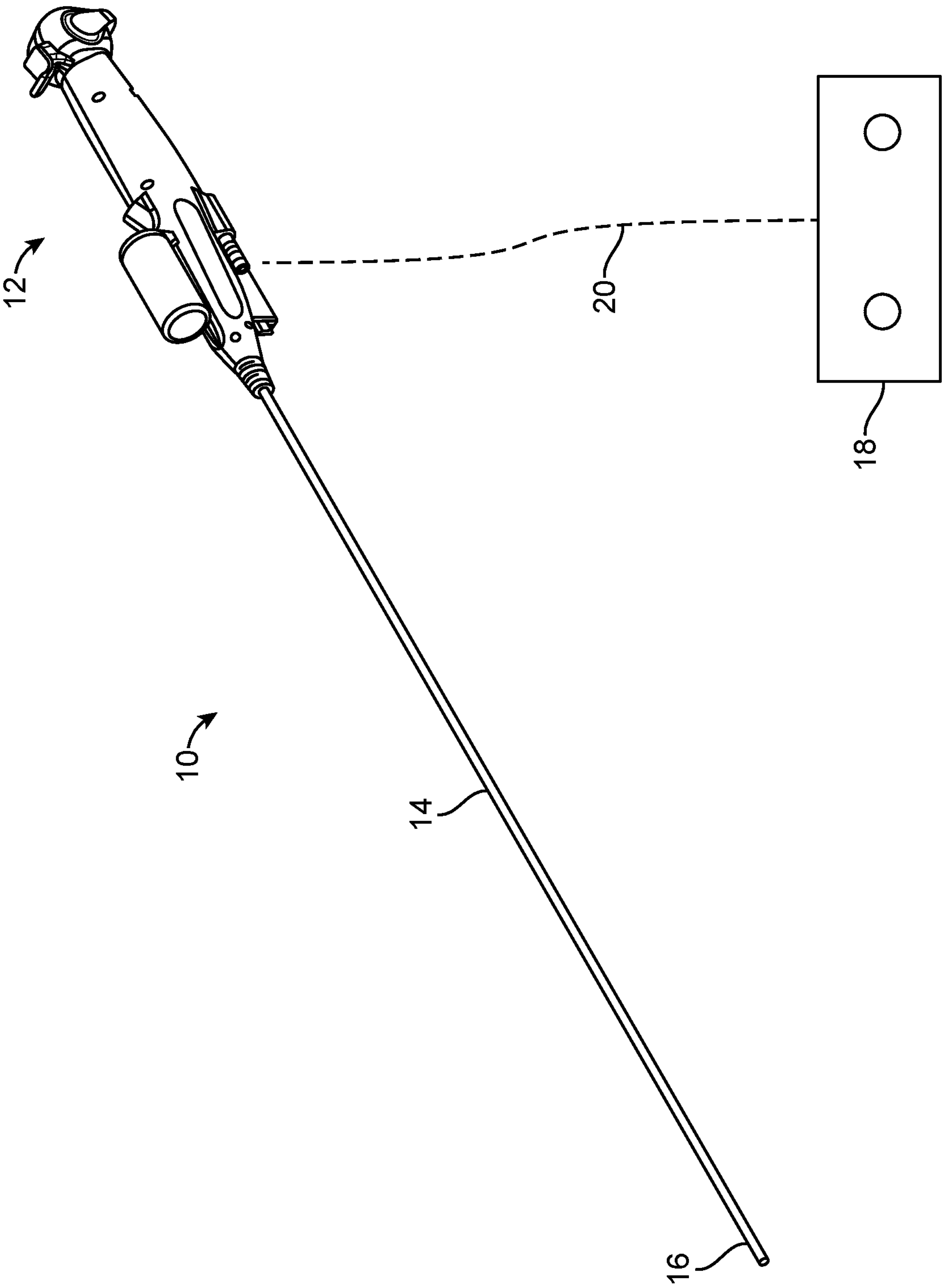
FIG. 1 is a perspective schematic of the kidney stone treatment system according to an embodiment.

FIG. 1 illustrates an embodiment of a treatment system 10 used to remove debris, such as kidney stones. The system 10 includes a handle mechanism 12 from which a catheter 14 extends. In the embodiments described below, the handle 12 can be configured to provide, for example, a single trigger design comprising, or consisting of, two modes: an active irrigation mode only (i.e., active irrigation on/vacuum off) and an active irrigation mode in combination with a vacuum mode (i.e., active irrigation on/vacuum on). In the embodiments described below, the handle 12 can be configured to provide, for example, a single trigger design comprising, or consisting of, three modes: passive irrigation on/active irrigation off/vacuum off; passive irrigation on/active irrigation on/vacuum off; passive irrigation on/active irrigation on/vacuum on. In an embodiment, there may be a minimum, passive amount of negative pressure even in the modes where the vacuum is off. Some aspects of the flow design allow for an uninterrupted conduit between the end of the device and the vacuum source such that there is high flow when vacuum is activated and minimal or no flow when vacuum is not activated. The catheter 14 can include various ports and lumens, including a vacuum lumen and an irrigation lumen running along the length of the catheter 14. The system 10 can also include a camera (digital visualization and lighting, e.g., video chip and LED) positioned at an end, distal face or a distal portion of the catheter 14 for providing real time imaging to the physician. A distal assembly 16 is at the distal end of the catheter 14 for irrigation and removal of the debris, with the assistance of the negative pressure applied through the vacuum lumen. The handle mechanism 12 allows the physician to hold and operate the system 10. The handle mechanism 12 can include features that allow a physical to operate various functions of the system, including the camera, vacuum pressure, the amount of irrigation and irrigation pressure, and the maneuverability of the catheter 14. For example, the handle mechanism 12 can include mechanical and electronic controls that allow the physician to adjust the amount of negative pressure, regulate the discharge of the irrigation fluid, and steer the catheter through tortuous anatomical passageways via the use of wheels and/or levers attached to cables, as is well known in the art. The system 10 can be coupled to a control unit 18 via a connector 20. The control unit 18 can control or assist in controlling aspects of the operation of the system 10. For example, the control unit 18 can control or assist in controlling visualization aspects of the system 10. The connector 20 can be a wired connection and/or a wireless connection.

Figure 2:
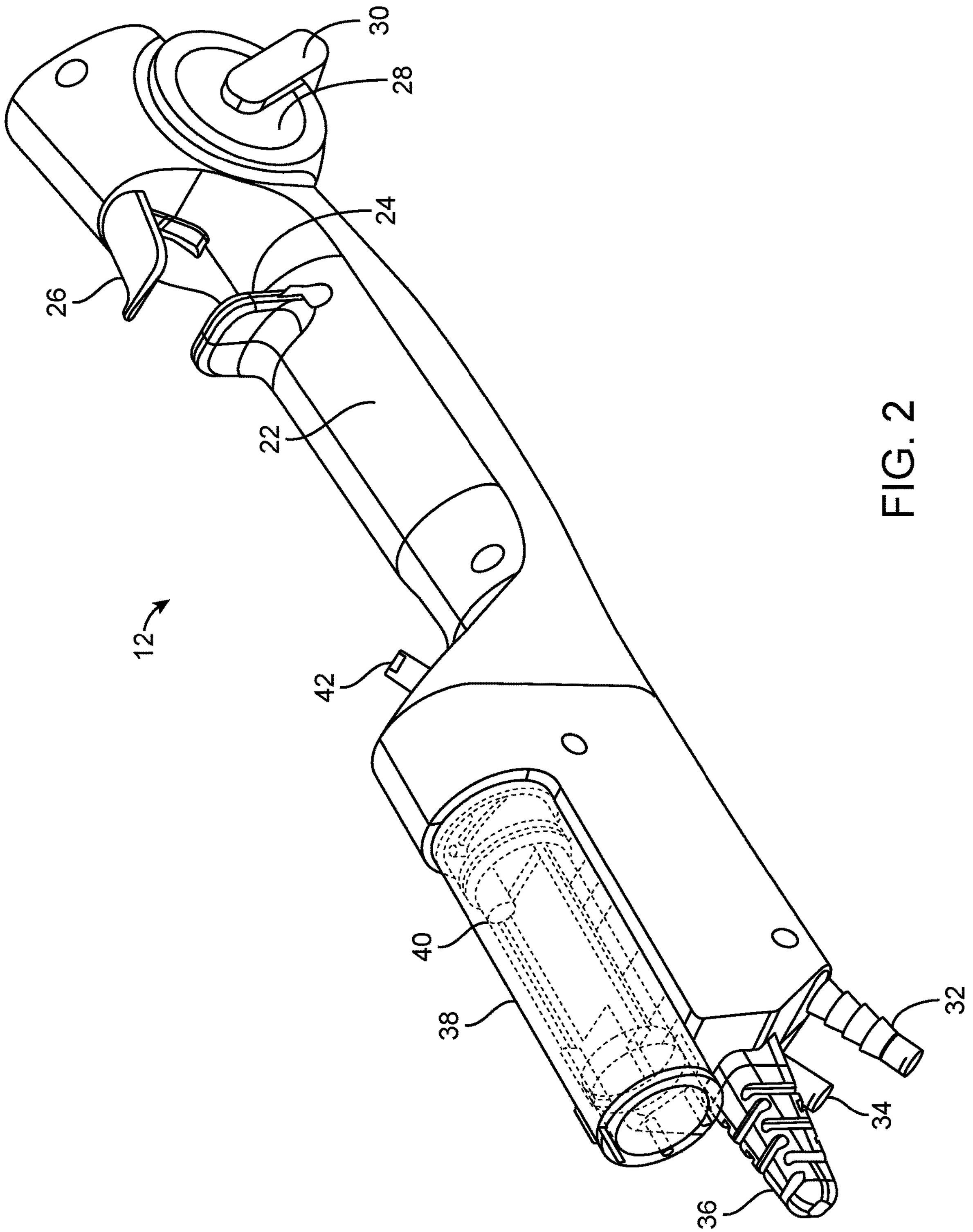
FIG. 2 is a perspective view of a kidney stone removal mechanism according to an embodiment.

FIG. 2 shows the handle mechanism 12 for effecting kidney stone removal according to an embodiment. A finger grip portion 22 runs a portion of a length of the mechanism 12. An optional ledge portion 24 sits over where a user's hand would be while gripping the mechanism 12. Above the optional ledge portion 24 is a trigger 26, which is a part of a trigger mechanism to be described later. The trigger mechanism controls vacuum (or suction) and air flow, as well as irrigation operation of the mechanism 12. A user may operate the trigger 26 with one of their fingers. A distal tip steering control 28 sits at a proximal end portion of the mechanism 12. A user's thumb may control the positioning and/or steering of the distal tip of a catheter by manipulating a lever 30. Various types of catheters may be employed with the mechanism 12, including but not limited to those shown and described in U.S. Pat. No. 11,116,530. U.S. Pat. No. 11,116,530 shows and describes one or more pull wires, which can steer the distal tip of a catheter through manipulation of the lever 30 to which the one or more pull wires may be attached. FIG. 2 also shows a vacuum/suction port 32 and an irrigation port 34, as well as a catheter strain relief 36. A stone catcher receptacle 38 receives extracted kidney stones and/or fragments through a port 40. An access or working channel port 42 permits access to the catheter (not shown) to allow introduction of therapeutic tools such as lasers to the distal end of the catheter.

Figure 5:
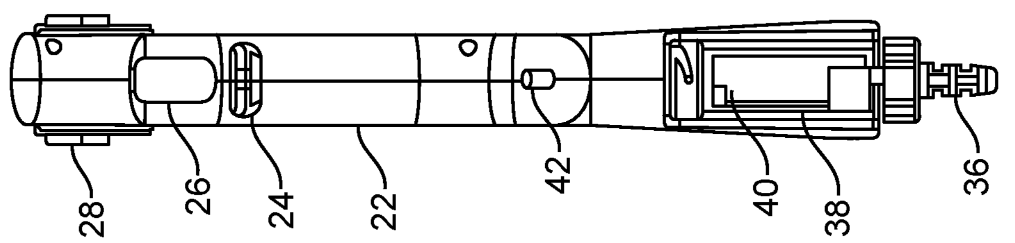
FIG. 5 is a front view of the mechanism shown in FIG. 2.
Figure 4:
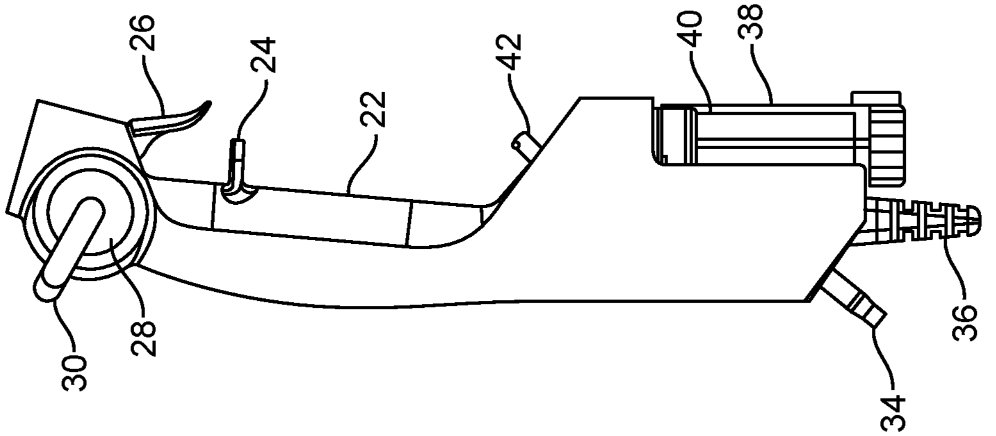
FIG. 4 is a side view of the mechanism shown in FIG. 2.
Figure 3:
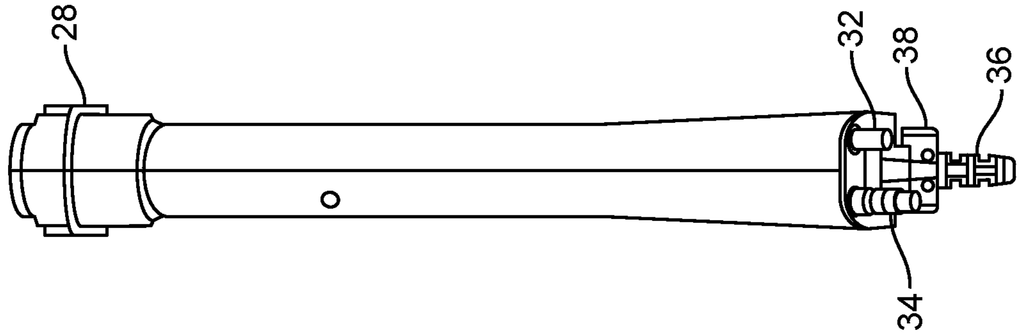
FIG. 3 is a rear view of the mechanism shown in FIG. 2.

FIG. 3 shows a rear view of the handle mechanism 12. In FIG. 3, the vacuum port 32, irrigation port 34, and catheter strain relief 36 are visible, as are the stone catcher receptacle 38 and distal tip steering control 28. FIG. 4 shows a side view of the mechanism 12. In FIG. 4, many of the same elements are visible as in FIG. 2. The finger grip portion 22, with the ledge portion 24 sitting above, fits a user's hand above the access or working channel port 42. The vacuum port 32, irrigation port 34, and catheter strain relief 36 sit at the bottom of the mechanism 12, behind the stone catcher receptacle 38. The port 40, which deposits kidney stones, or fragments or portions of kidney stones, into the stone catcher receptacle 38, also is visible. In FIG. 5, which is a front view of the mechanism 12, many of the same elements are visible as in FIG. 2. The finger grip portion 22, with the ledge portion 24 sitting above, fits a user's hand above the access or working channel port 42. The catheter strain relief 36 sits at the bottom of the mechanism 12, behind the stone catcher receptacle 38. The port 40, which deposits kidney stones or portions of kidney stones into the stone catcher receptacle 38, also is visible.

Figure 6:
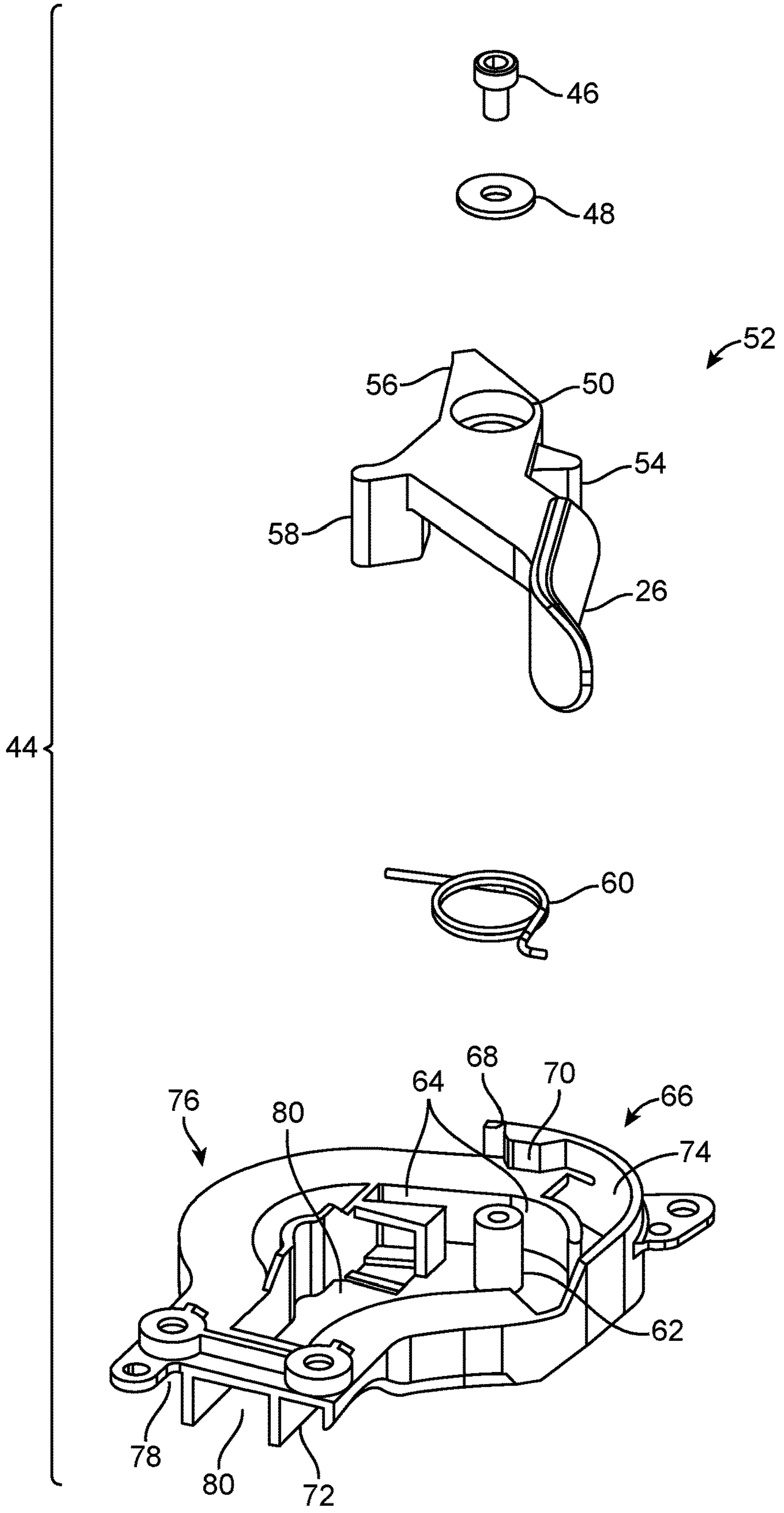
FIG. 6 is an exploded view of a trigger activation mechanism according to an embodiment.

FIG. 6 is an exploded view of a portion at the top of the mechanism 12. Collectively, the parts in FIG. 6 constitute a trigger mechanism assembly 44. Going from top to bottom in FIG. 6, a screw or bolt 46 passes through a washer 48 and opening 50 of a trigger mechanism 52. The trigger mechanism 52 includes protrusions 54, 56, and 58. The function of these protrusions during actuation of the trigger mechanism 52 will be described in more detail below with respect to FIGS. 7-9. The screw or bolt 46 also passes through a spring 60 or other resilient device and is received by a screw/bolt receptacle 62. In some examples, the bolt 46 holds the trigger securely to a base plate boss that captures the spring 60. The spring 60 provides resilience for the trigger mechanism 52, so that the trigger mechanism 52 returns to its original, home position when a user releases or removes pressure from the trigger 26. The spring 60 or other resilient device sits in opening 64 of a mechanism casing or body 66. The mechanism body 66 also includes first and second detents 68 and 70, whose function will be described in more detail below with respect to FIGS. 7-9. In some examples, the mechanism body 66 may contain more or fewer detents. When the handle mechanism 12 is assembled, mechanism casing 66 is not visible. In FIG. 6 and in subsequent figures, the mechanism casing 66 is exposed for ease of description of the function of the trigger mechanism 52. An irrigation tube (not shown) enters through opening 72, proceeds through opening 74, under a covering portion 76, and exits through an opening 78. A vacuum activation tube (not shown) sits inside the mechanism casing 66, and exits through opening 80.

Figure 35:
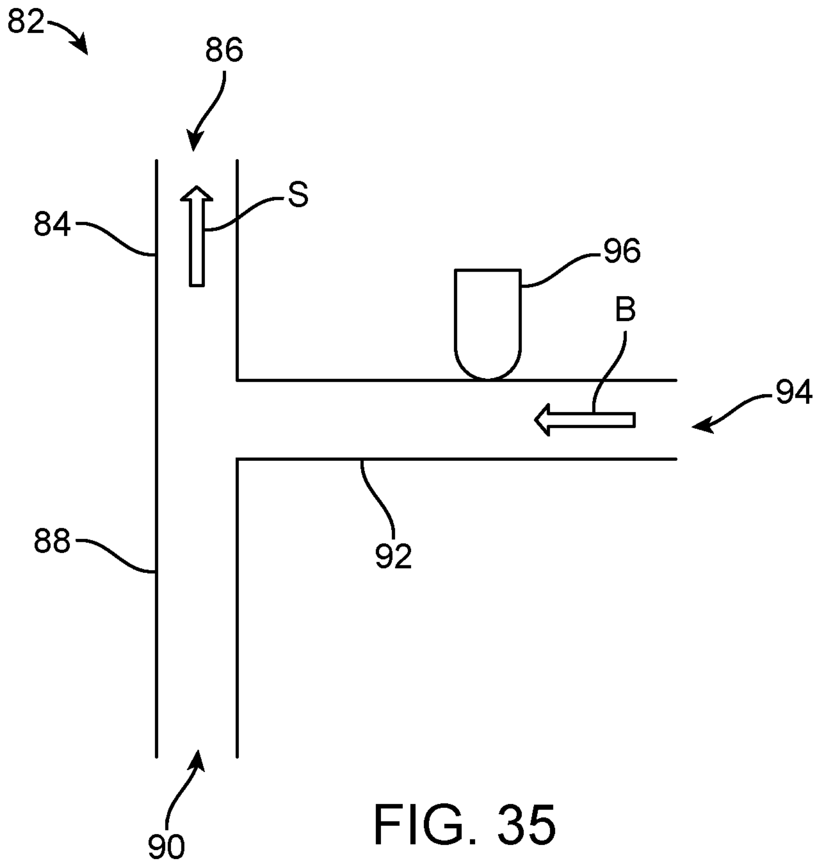
FIGS. 35 and 36 show schematic diagrams of a vacuum/suction control system and method according to an embodiment.
Figure 36:
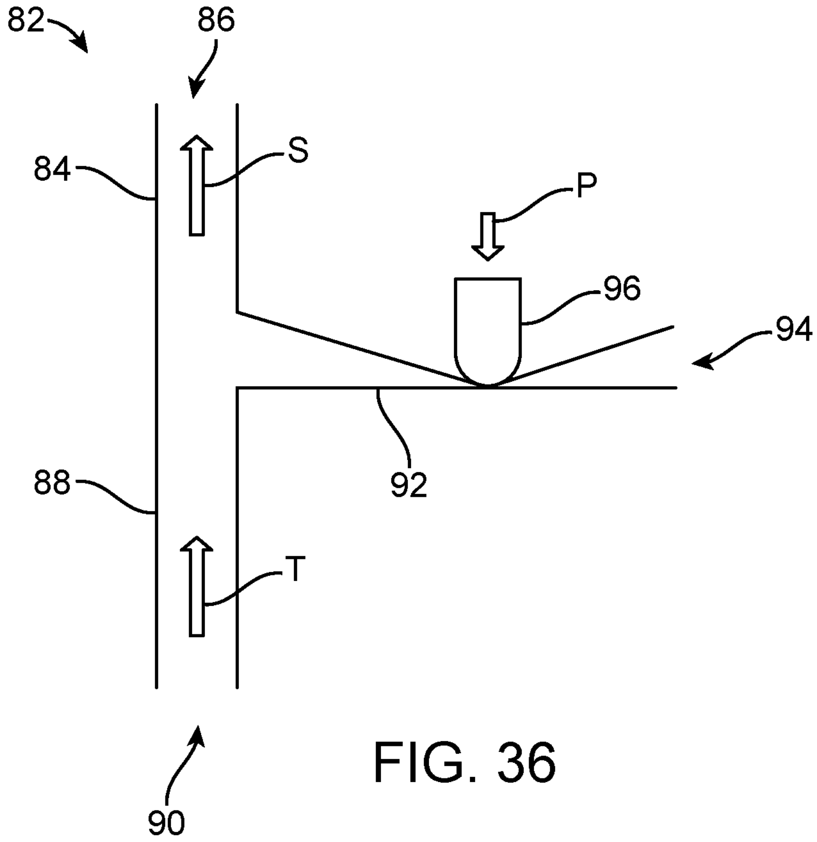

Advancing to FIGS. 35 and 36, they show schematic diagrams of a vacuum/suction control system and method 82. A suction outlet tube 84 includes a suction opening 86, which is connected to a vacuum/suction source (not pictured). Flow through the suction outlet tube 84 is in the direction of arrow S. A suction target tube 88 includes a target opening 90, which is connected to a portion of the device that is in proximity of an area targeted for suction/vacuum. FIG. 36 shows a configuration in which flow through suction target tube 88 is in the direction of arrow T. An activation tube 92 includes an activation opening 94, which is open to ambient air. An activation pinch mechanism 96 is positioned adjacent to the activation tube 92 and is movable in the direction of arrow P from first position that allows flow in the direction of arrow B through the activation tube 92 (shown in FIG. 35) and a second position that prevents flow from activation opening 94 through activation tube 92 (shown in FIG. 36). The system and method 82 shows that the activation pinch mechanism 96 allows for control over the vacuum/suction flow. The vacuum source (not pictured) can be set to a provide a constant amount of suction (e.g., 200 mmHg) and the activation pinch mechanism 96 provides for on/off control over the vacuum/suction by opening or closing the activation tube 92. In the configuration shown in FIG. 35, the activation pinch mechanism 96 is positioned such that air flows through the activation tube 92 in the direction of arrow B, through the suction outlet tube 84 in the direction of arrow S, and out to the vacuum/suction source. In the configuration shown in FIG. 35, little or no flow is through the suction target tube 88 from the targeted area to the suction outlet tube 84. In the configuration shown in FIG. 35, there is no (or comparatively little) suction applied to the target area and vacuum is off at the target area. In the configuration shown in FIG. 36, the activation pinch mechanism 96 is positioned such that no air flows through the activation tube 92. In the configuration shown in FIG. 36, all the flow is through the suction target tube 88 from the targeted area in the direction of arrow T to the suction outlet tube 84 and out the suction opening 86 in the direction of arrow S. In the configuration shown in FIG. 36 vacuum is on at the target area.

Figure 7:
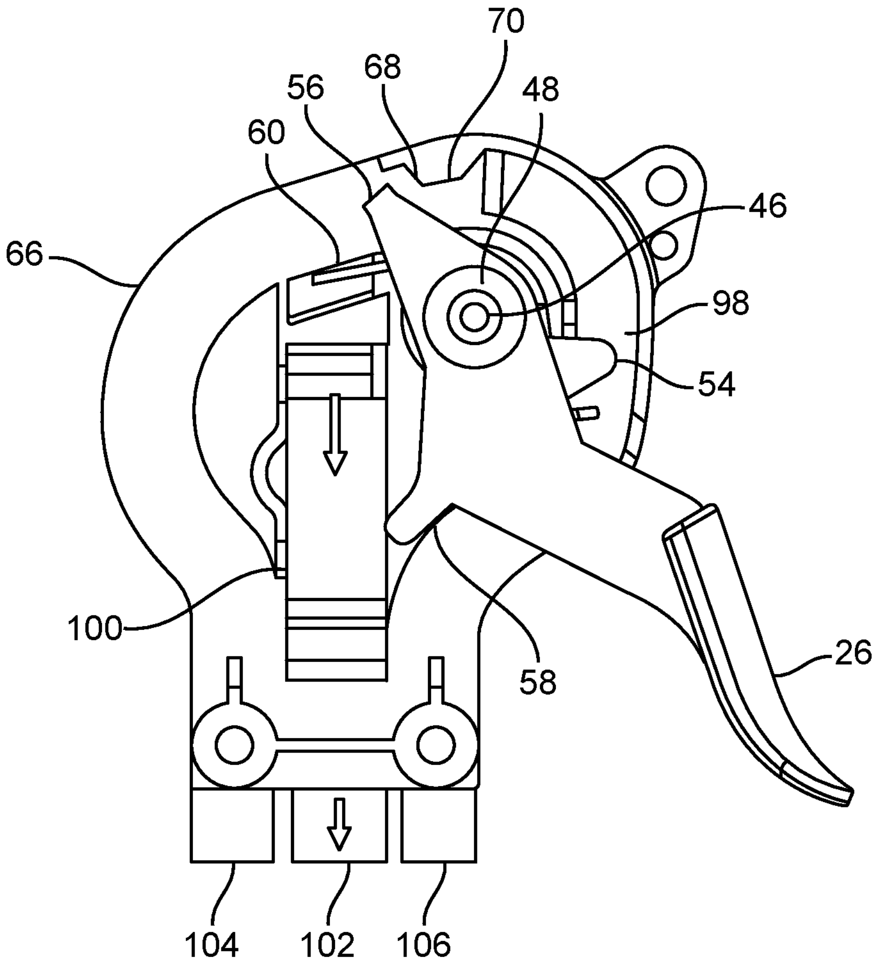
FIGS. 7 to 9 show successive positions of a trigger according to an embodiment.
Figure 8:
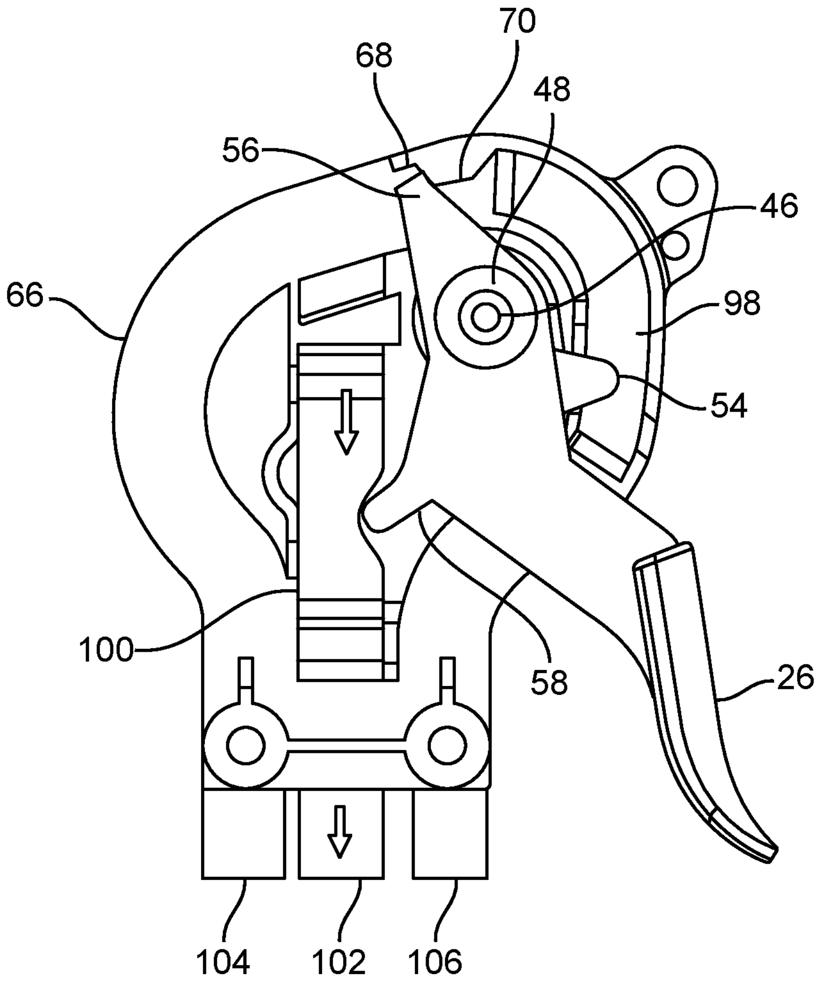
Figure 9:
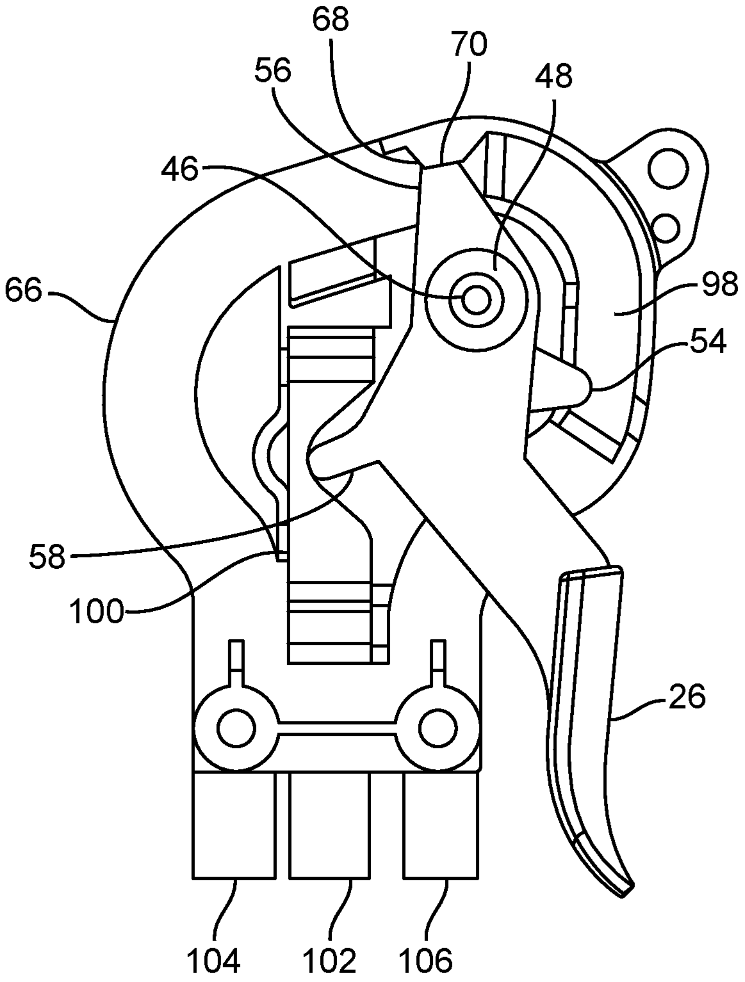
Figure 10:
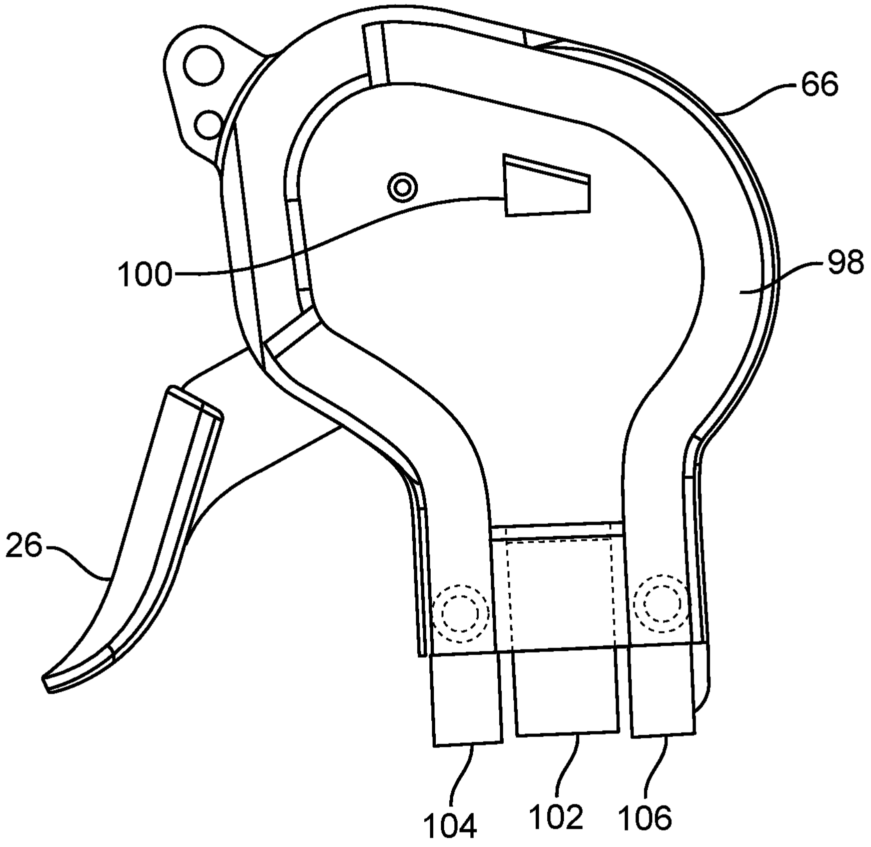
FIG. 10 is a reverse view of a trigger activation mechanism according to an embodiment.

FIGS. 7-9 show successive positions of the trigger 26. In FIG. 7, the trigger 26 is in the undepressed position. With the trigger 26 in that position, the vacuum and irrigation in the handle mechanism 12 are turned off. In some examples, an irrigation bypass structure may allow for a minimum amount of irrigation to flow even when trigger 26 is in the undepressed position. The protrusion 54 pinches off an irrigation tube 98. The protrusion 56 is not in contact with the detent 68. The protrusion 58 may contact, but does not compress, a vacuum activation tube 100 (see also, for example, the activation tube 92 of FIGS. 35 and 35). The vacuum activation tube 100 is open to ambient air at one end and connected at an end 102 with vacuum tubing running from a vacuum source to a vacuum lumen running to the vacuum target area. The spring 60 or other resilient device engages the trigger mechanism 52 resiliently so that, when the user releases the trigger 26, the trigger 26 returns to its initial position, so that irrigation and vacuum are turned off. In some embodiments, irrigation is partially on at a minimum level and vacuum is off when the trigger 26 returns to its initial position. In FIG. 8, the trigger 26 is partly depressed, up to the point that the protrusion 56 contacts detent 68 in the mechanism body 66, indicating to the user that a first stopping point in operation has been reached. With the trigger 26 in this position, the protrusion 54 partly disengages with the irrigation tube 98, opening the irrigation tube 98 slightly, and allowing for some irrigation (or, in some embodiments, full irrigation flow). The protrusion 58 partly closes off the vacuum activation tube 100, but air still can flow through the vacuum activation tube 100, so vacuum at the target area still is off. In FIG. 9, the trigger 26 is fully depressed. The protrusion 56 proceeds past the detent 68 and seats up against the detent 70. In this position, the protrusion 58 pinches off the vacuum activation tube 100, thereby turning the vacuum on at the target area. The protrusion 54 opens the irrigation tube 98 further, so that irrigation continues, and kidney stones and/or pieces of kidney stones can be removed and deposited in the stone catcher receptacle 38 (FIGS. 2-5). FIG. 10 shows a view of the mechanism body 66 from an opposite side to those shown in FIGS. 7-9. The irrigation tube 98 has an inlet 104 and an outlet 106. The activation tube 100 runs through the mechanism body 66. The trigger 26 has protrusions (not shown) which interact with the irrigation tube 98 and the activation tube 100 according to a degree of depression of the trigger 26. In the foregoing descriptions of kidney stone removal mechanism, the function of the inlet 104 and the outlet 106 can be reversed, so that element 104 operates as an irrigation outlet, and element 106 operates as an irrigation inlet.

Figure 11:
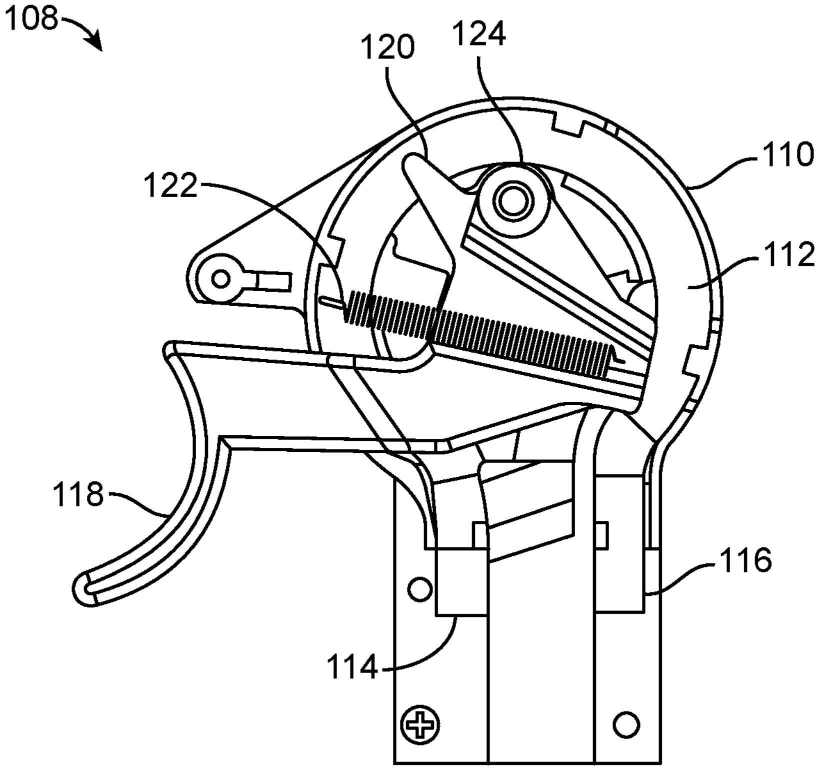
FIGS. 11 and 12 show successive positions of a trigger in a trigger activation mechanism according to an embodiment.
Figure 12:
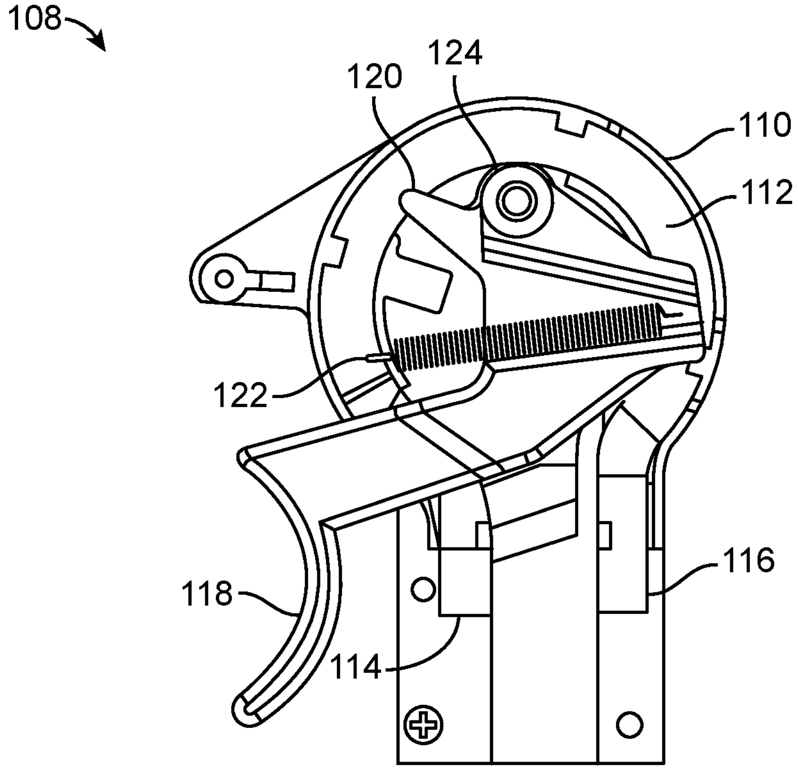
Figure 13:
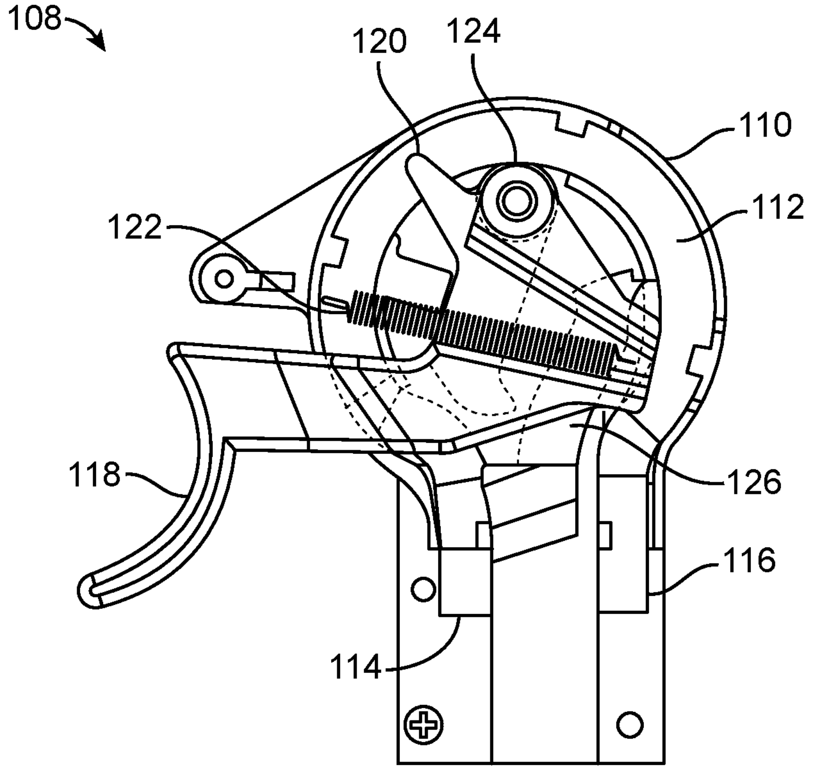
FIGS. 13 and 14 show successive positions of a trigger in a trigger activation mechanism according to an embodiment.
Figure 14:
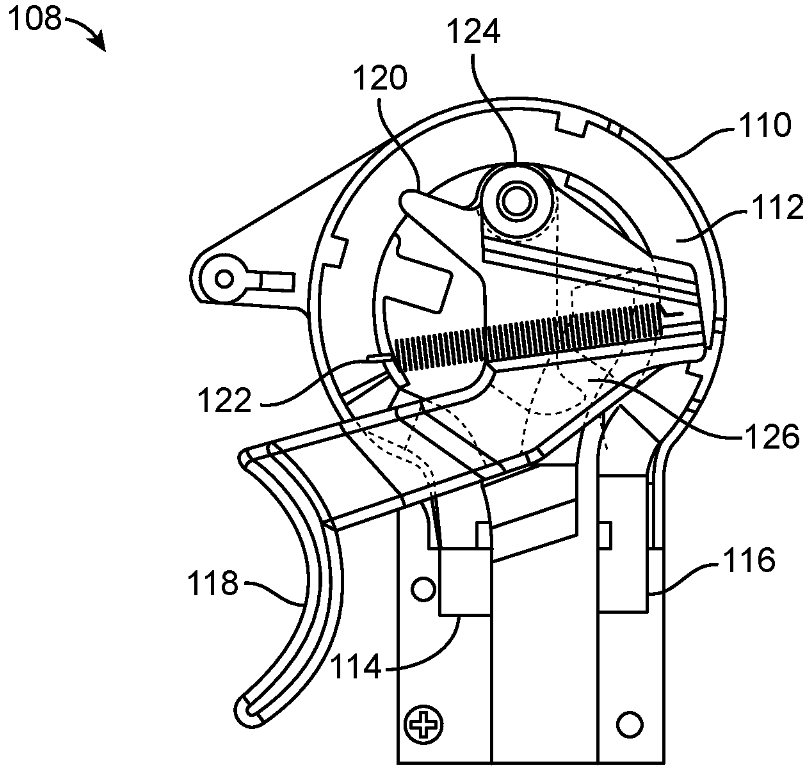

FIG. 11 shows a portion of a kidney stone removal mechanism 108 according to an embodiment. A mechanism casing or body 110 contains an irrigation tube 112 with an irrigation inlet 114 and an irrigation outlet 116. A trigger 118 has a protrusion 120 which interacts with the irrigation tube 112. When the trigger 118 is undepressed, as shown in FIG. 11, the protrusion 120 closes off, or at least constricts, the irrigation tube 112. A spring 122 or other resilient device moves against the force of a user depression of trigger 118 to return the trigger 118 to its undepressed state when the user releases the trigger 118. When depressed, the trigger 118 rotates around a pivot point 124, causing the protrusion 120 to move away from the irrigation tube 112 to open the tube and enable irrigation. FIG. 12 shows structure similar to that in FIG. 11, except that in FIG. 12, the trigger 118 is depressed, so that the protrusion 120 moves away from the irrigation tube 112 to open it up. FIG. 13 shows structure similar to that in FIG. 11, but from an opposite side of the mechanism body 110. The trigger 118 is in the same position in FIG. 13 as in FIG. 11. When the trigger 118 is in this position, a vacuum tube (not shown) in position 126 will not be pinched, so that vacuum or suction will be off. Comparing FIG. 13 with FIG. 11, when vacuum or suction is off, so is irrigation. FIG. 14 shows structure similar to that in FIG. 13, except that in FIG. 14, the trigger 118 is depressed, so that the vacuum tube (not shown) in position 126 will be pinched, so that vacuum or suction will be on. Comparing FIG. 14 with FIG. 12, when vacuum or suction is on, so is irrigation, similarly to other described embodiments.

Unlike the embodiment of FIGS. 7 to 9, FIGS. 11 to 14 do not show an intermediate depression position for the trigger 118. However, ordinarily skilled artisans will appreciate that kidney stone removal mechanism 108 enables a range of depression positions for trigger 118. Accordingly, similarly to the embodiment of FIGS. 7 to 9, there is an intermediate depression for the trigger 118, whereby the irrigation tube 112 will be slightly un-pinched, allowing irrigation to flow, while the vacuum tube (not shown) will be slightly pinched, so that vacuum or suction still will be off.

Figure 15:
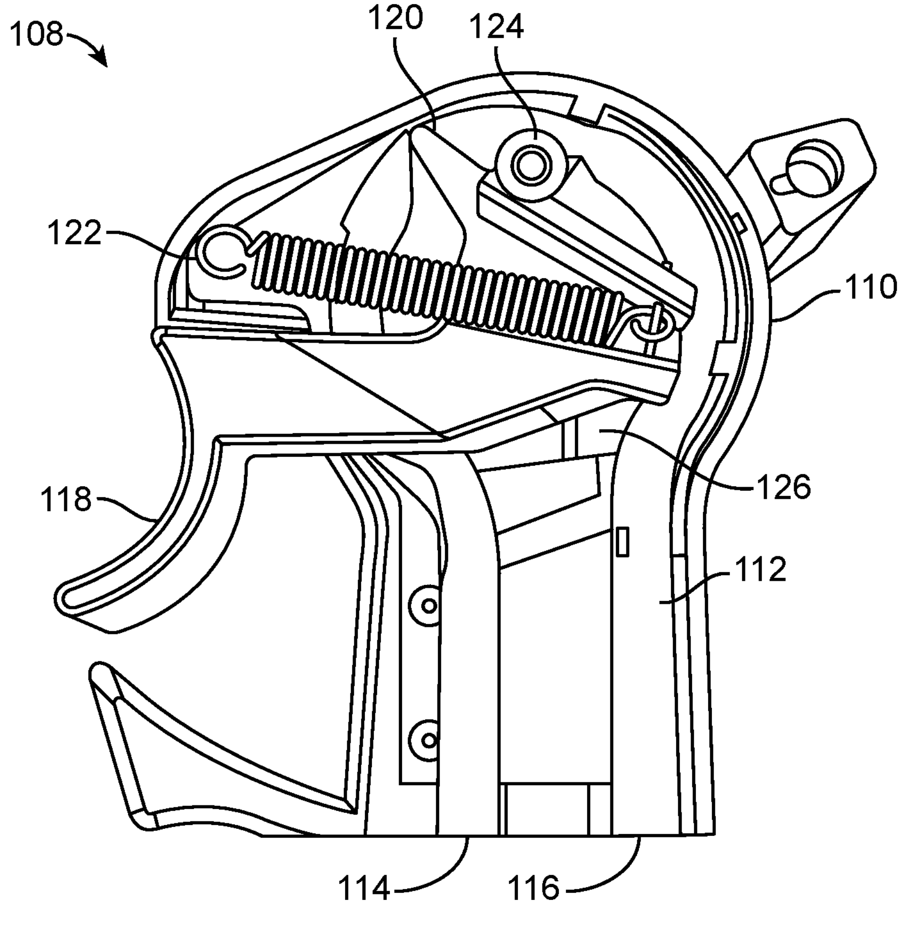
FIG. 15 is a trigger activation mechanism according to an embodiment.

FIG. 15 is a photograph of a portion of the kidney stone removal mechanism 108, similar to the structure in FIG. 11, according to an embodiment. The mechanism body 110 contains the irrigation tube 112 with the irrigation inlet 114 and the irrigation outlet 116. The trigger 118 has the protrusion 120 which interacts with the irrigation tube 112. When the trigger 118 is undepressed, as shown in FIG. 15, the protrusion 120 closes off, or at least constricts, the irrigation tube 112. The spring 122 or other resilient device moves against the force of a user depression of the trigger 118 to return the trigger 118 to its undepressed state when the user releases the trigger 118. When depressed, the trigger 118 rotates around the pivot point 124, causing the protrusion 120 to move away from the irrigation tube 112 to open up the tube and enable irrigation. The trigger 118 is in the same position in FIG. 15 as in FIG. 13. When trigger 118 is in this position, a vacuum tube (not shown) in position 126 will not be pinched, so that vacuum or suction will be off. When vacuum or suction is off, so is irrigation. In the foregoing descriptions, the function of the inlet 114 and the outlet 116 can be reversed, so that element 114 operates as an irrigation outlet, and element 116 operates as an irrigation inlet.

Figure 16:
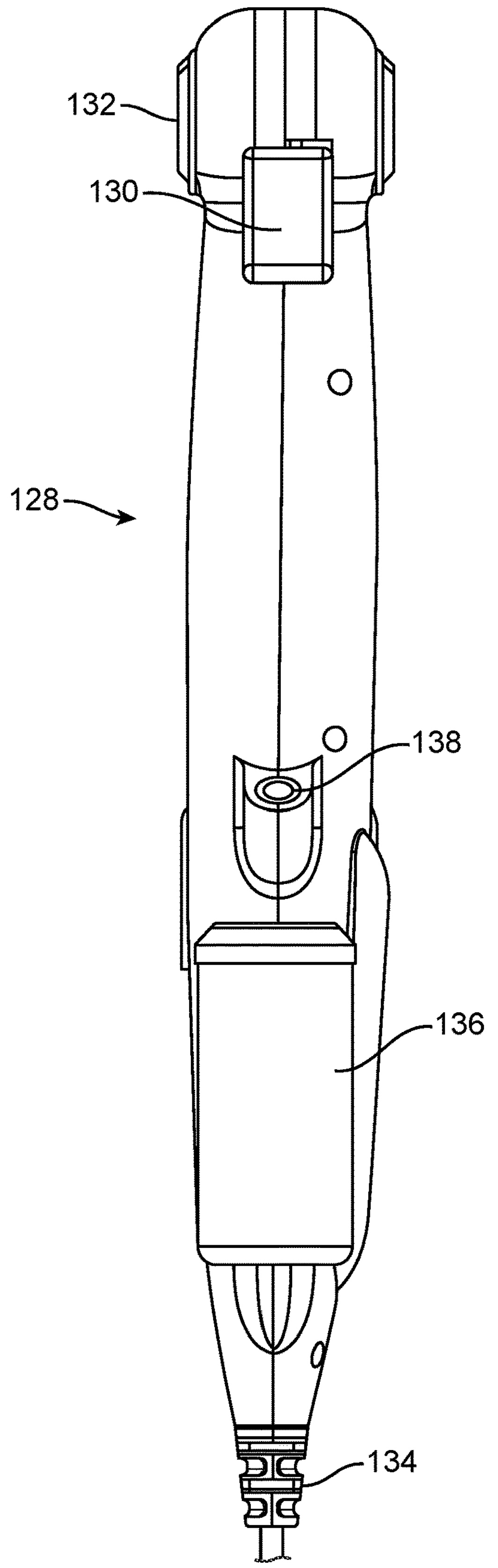
FIG. 16 is a front view of the kidney stone removal mechanism of an embodiment.
Figure 17:
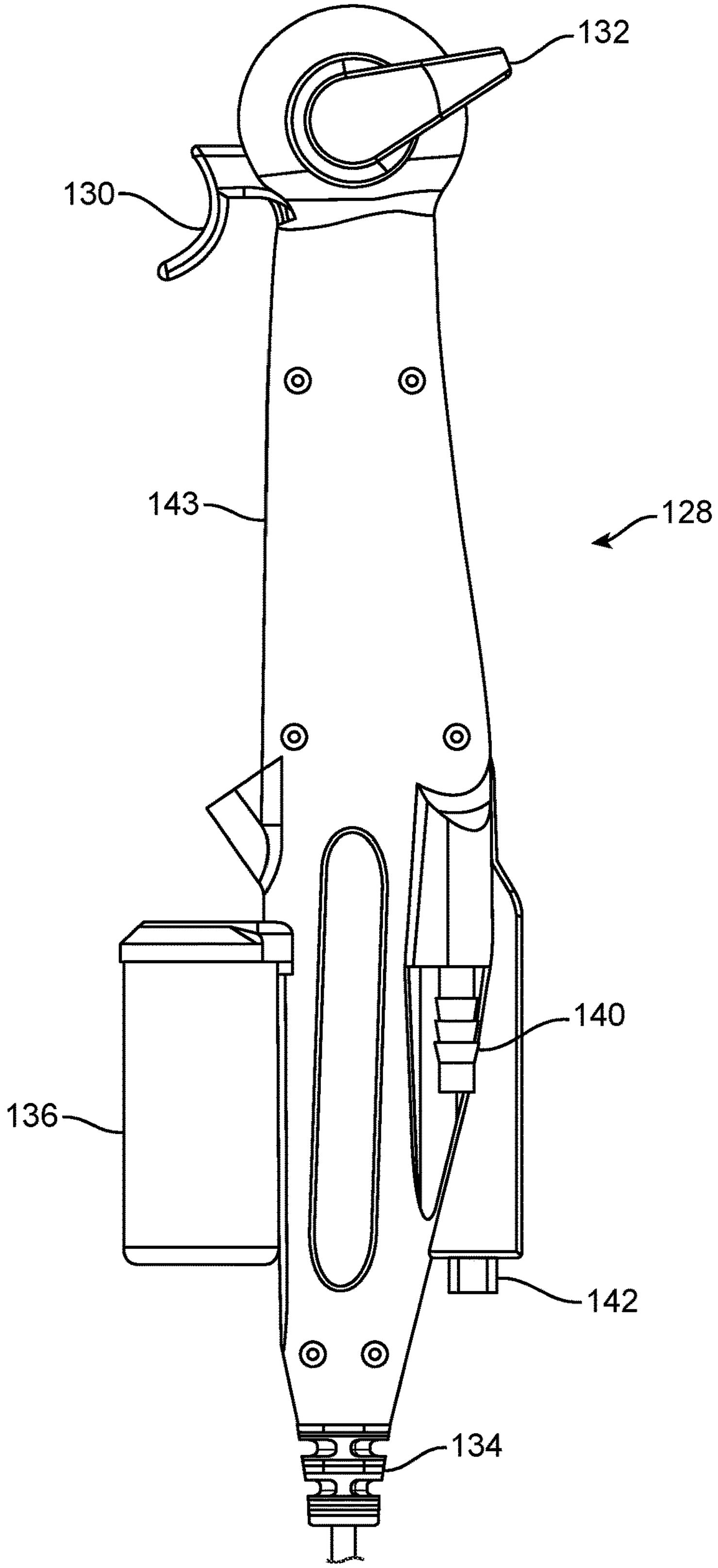
FIG. 17 is a side view of the kidney stone removal mechanism of an embodiment.
Figure 18:
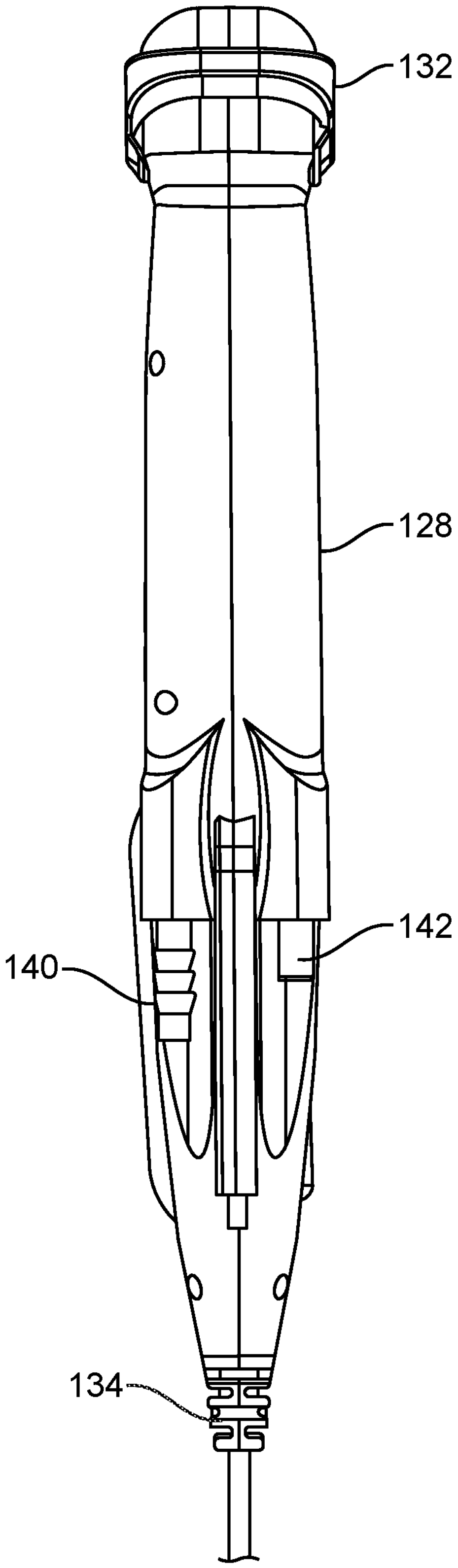
FIG. 18 is a rear view of the kidney stone removal mechanism of an embodiment.
Figure 19:
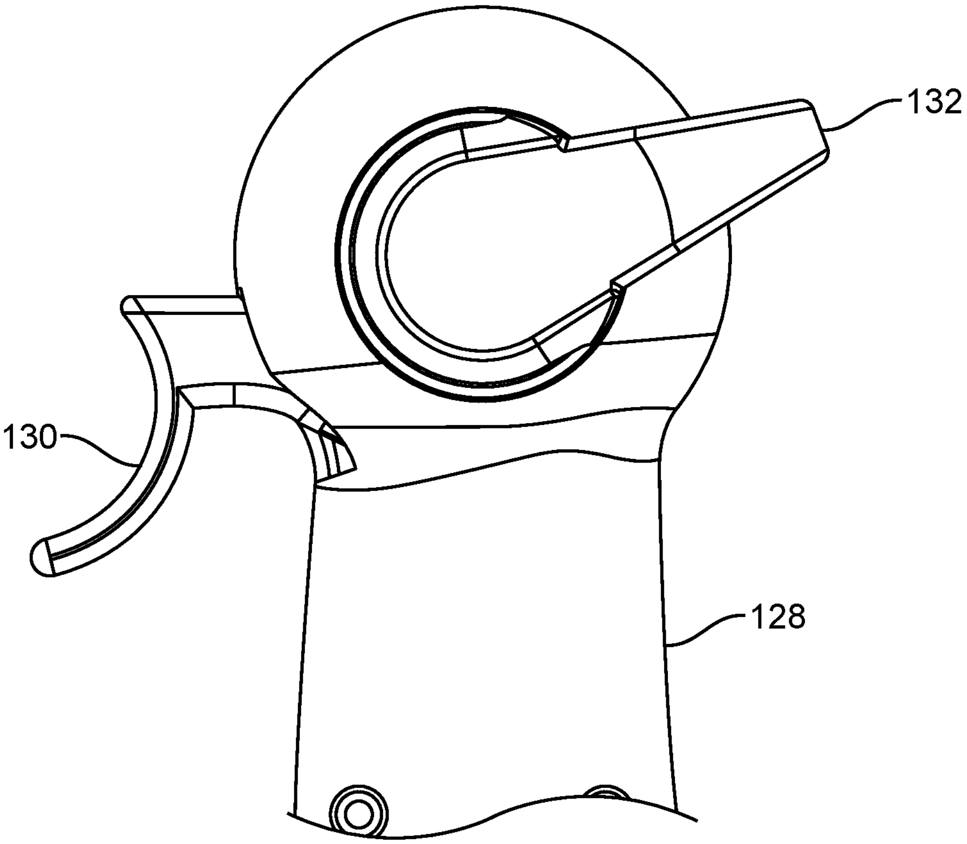
FIGS. 19 to 21 show successive positions of a trigger according to an embodiment.
Figure 20:
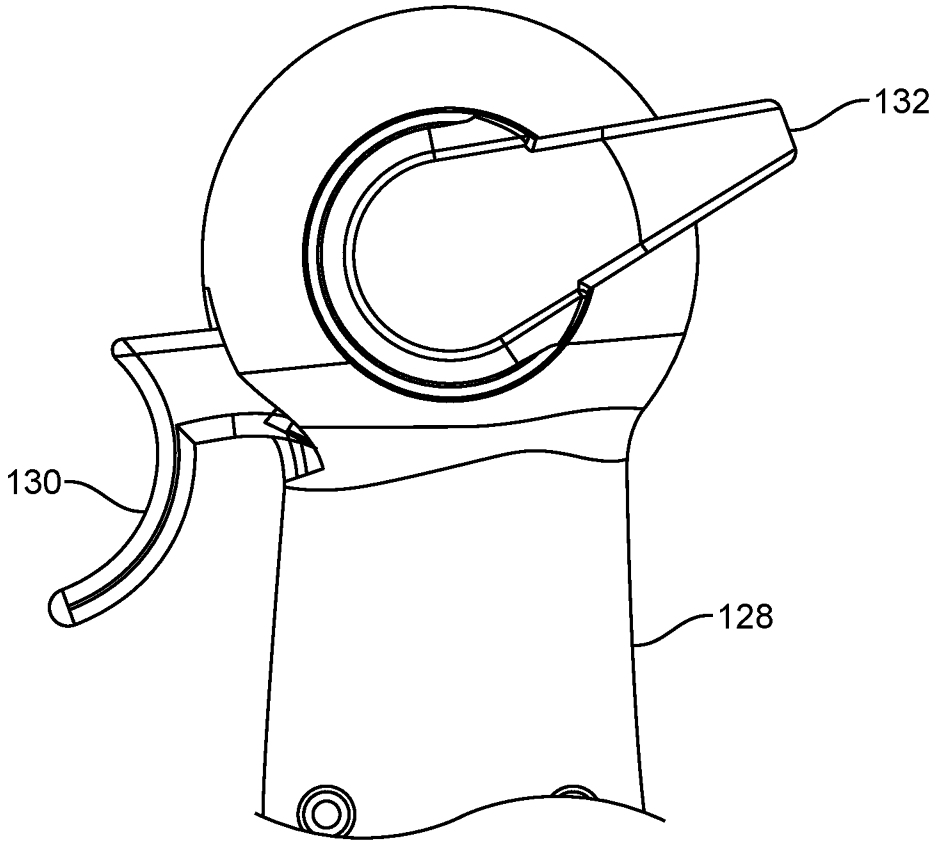
Figure 21:
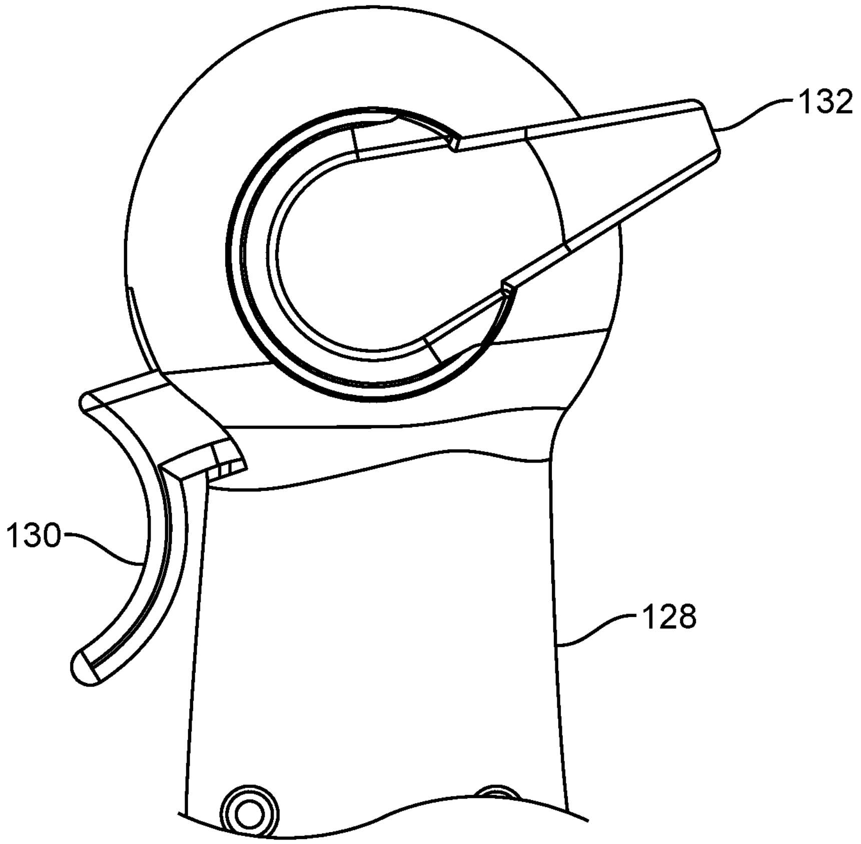
Figure 22:
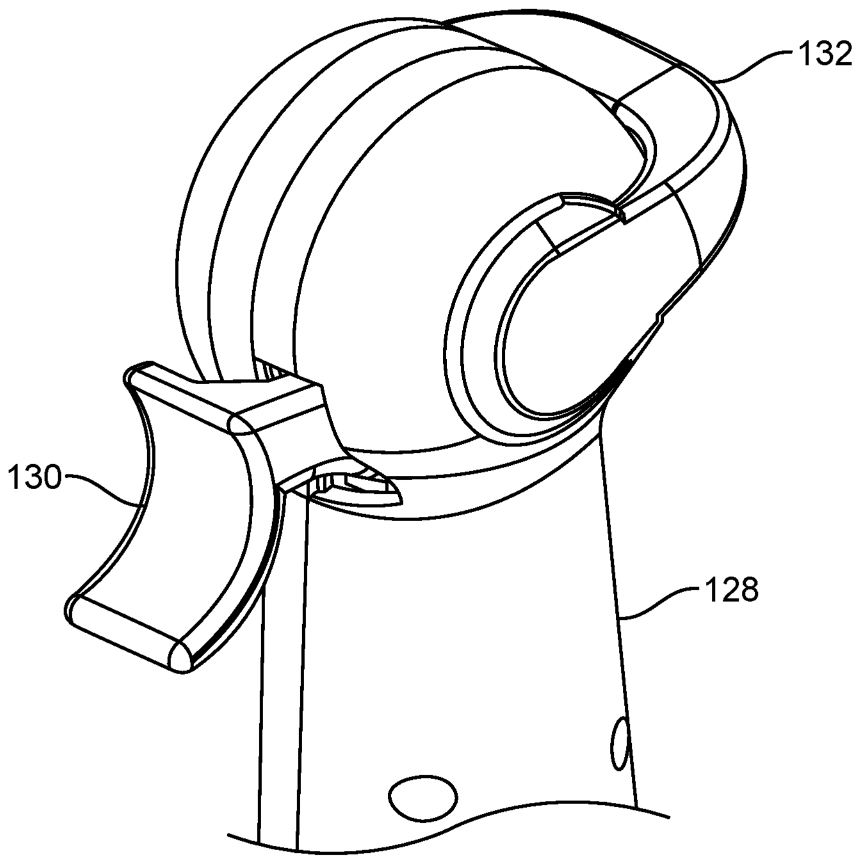
FIG. 22 is a close-up perspective view of the trigger and a distal tip control mechanism in FIGS. 16 to 21.

FIGS. 16-22 show a kidney stone removal mechanism 128 according to an embodiment. A finger grip portion runs a portion of the length of mechanism. A trigger mechanism 130 is located at a proximal end of the kidney stone removal mechanism 128. A distal tip steering mechanism 132, also located at a proximal end of the kidney stone removal mechanism 128, enables manipulation of a catheter, particularly a distal end of a catheter, to position the distal end as desired for kidney stone fracture and/or removal. The catheter is connected to catheter strain relief 134. A stone catcher receptacle 136 receives removed kidney stones and/or pieces thereof. A working channel port 138 permits access to the catheter for insertion of devices and tools. In FIG. 16, showing a front view of the kidney stone removal mechanism 128, there is a more detailed view of the catheter strain relief 134. There also is a front view of the stone catcher receptacle 136. The access or working channel port 138 permits access to a catheter to allow introduction of therapeutic tools such as lasers to the distal end of the catheter. FIG. 16 also shows a front view of the trigger 130, and a side view of the distal tip steering mechanism 132. FIG. 17 shows a side view of the kidney stone removal mechanism 128. A vacuum outlet 140 and irrigation inlet 142 are visible, as well as the catheter strain relief 134, the stone catcher receptacle 136, and a finger grip 143. In FIG. 18, showing a rear view of the kidney stone removal mechanism 128, the vacuum outlet 140 and the irrigation inlet 142 are visible, as is the catheter strain relief 134. The distal tip steering mechanism 132 also is visible. FIGS. 19-21 show close ups of successive positions of the trigger 130 of the kidney stone removal mechanism 132, from undepressed in FIG. 19 to fully depressed in FIG. 21. FIG. 22 shows a perspective side view of FIGS. 19-21.

Figure 23:
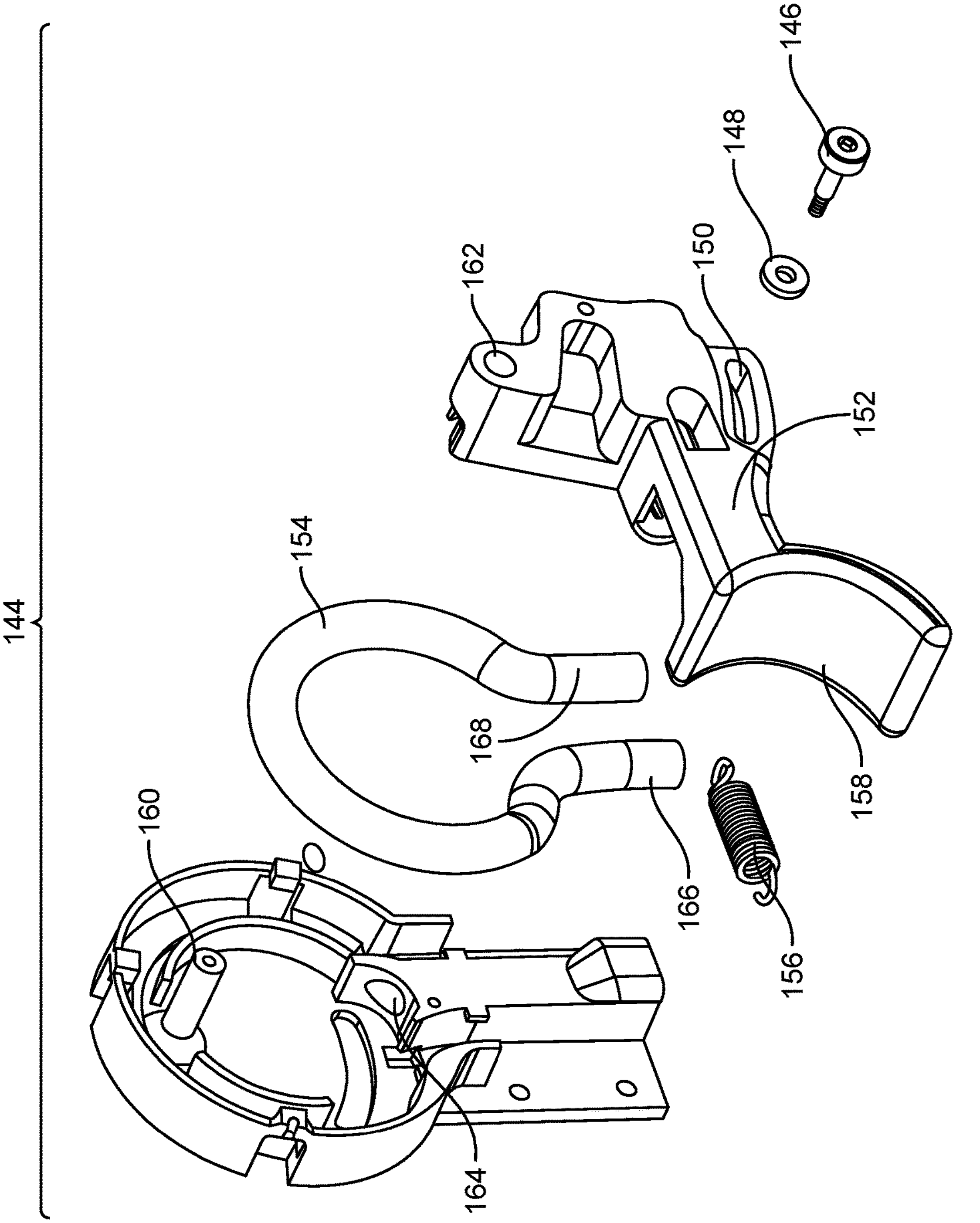
FIG. 23 is an exploded view of a trigger mechanism according to an embodiment.
Figure 24:
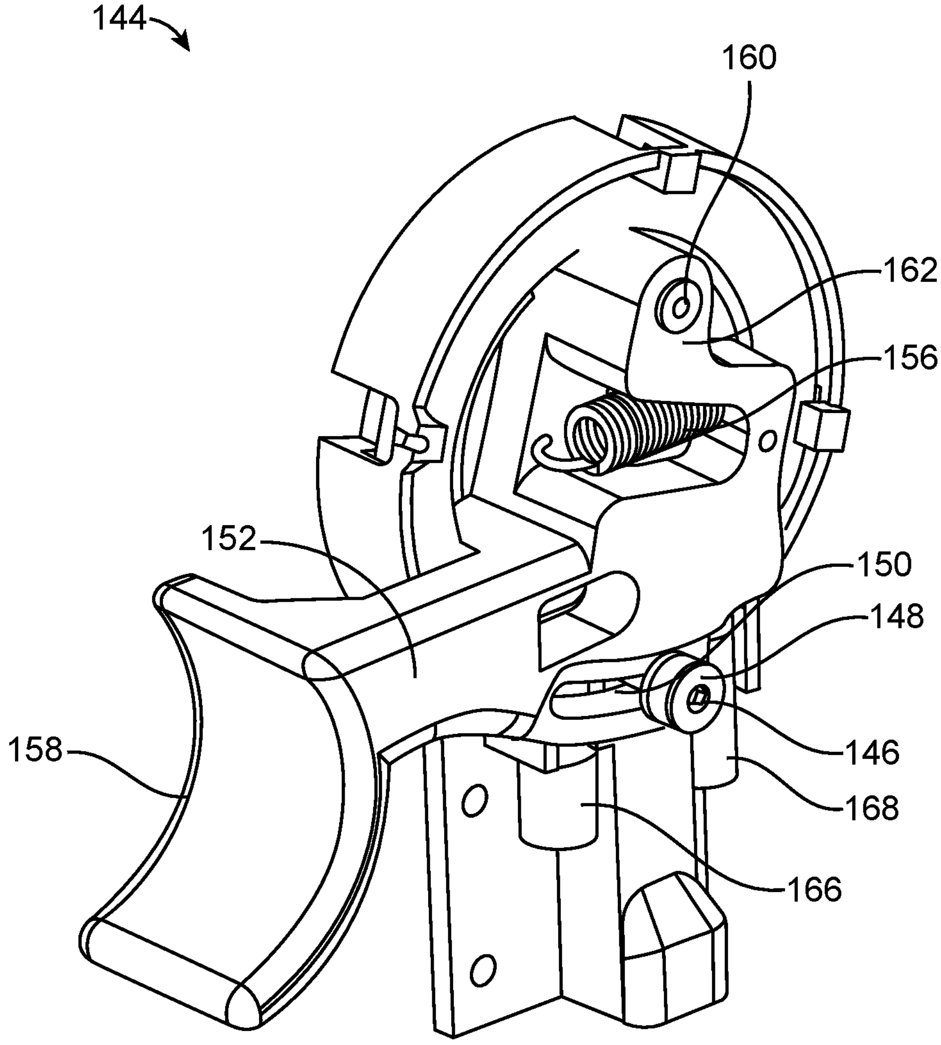
FIG. 24 is an assembled view of the trigger mechanism of FIG. 23.

FIG. 23 shows an exploded view of a trigger mechanism assembly 144 according to an embodiment. A bolt 146 and a washer 148 pass through a slot 150 in a trigger mechanism 152. An irrigation tube 154 has an irrigation inlet and irrigation outlet 166 and 168. A spring 156 biases a trigger 158 toward an undepressed position. A pivot 160 receives the trigger mechanism 152 by fitting through a hole 162 in the trigger mechanism 152. When a user actuates the trigger 158, the trigger mechanism 152 rotates around the pivot 160. An opening 164 leads to a vacuum outlet (not shown). FIG. 24 shows an assembled version of the trigger mechanism of FIG. 23. Elements discussed above with respect to FIG. 23 are depicted with the same reference numerals in FIG. 24.

Figure 25:
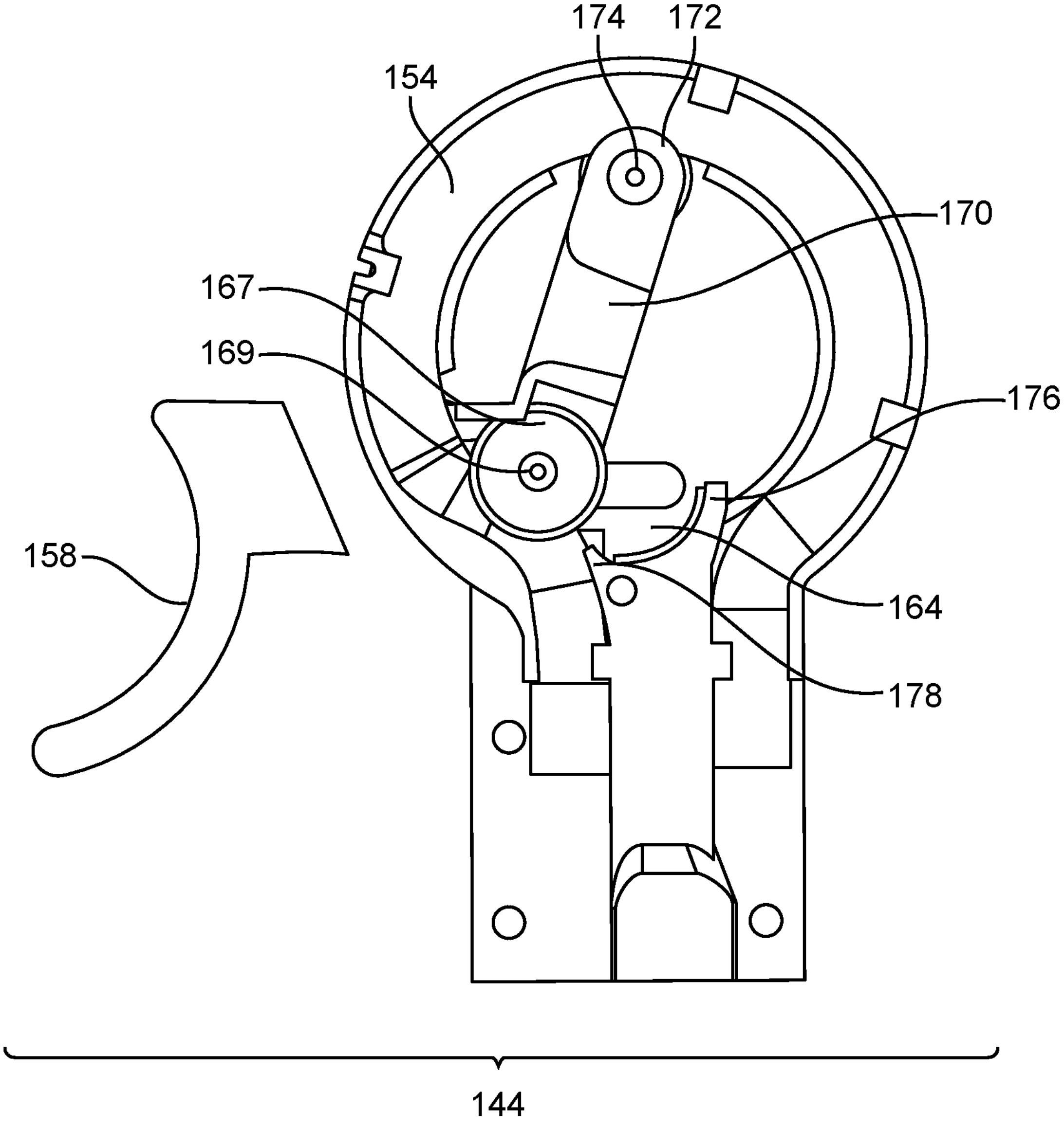
FIGS. 25 to 27 show successive positions of a trigger mechanism according to an embodiment.
Figure 26:
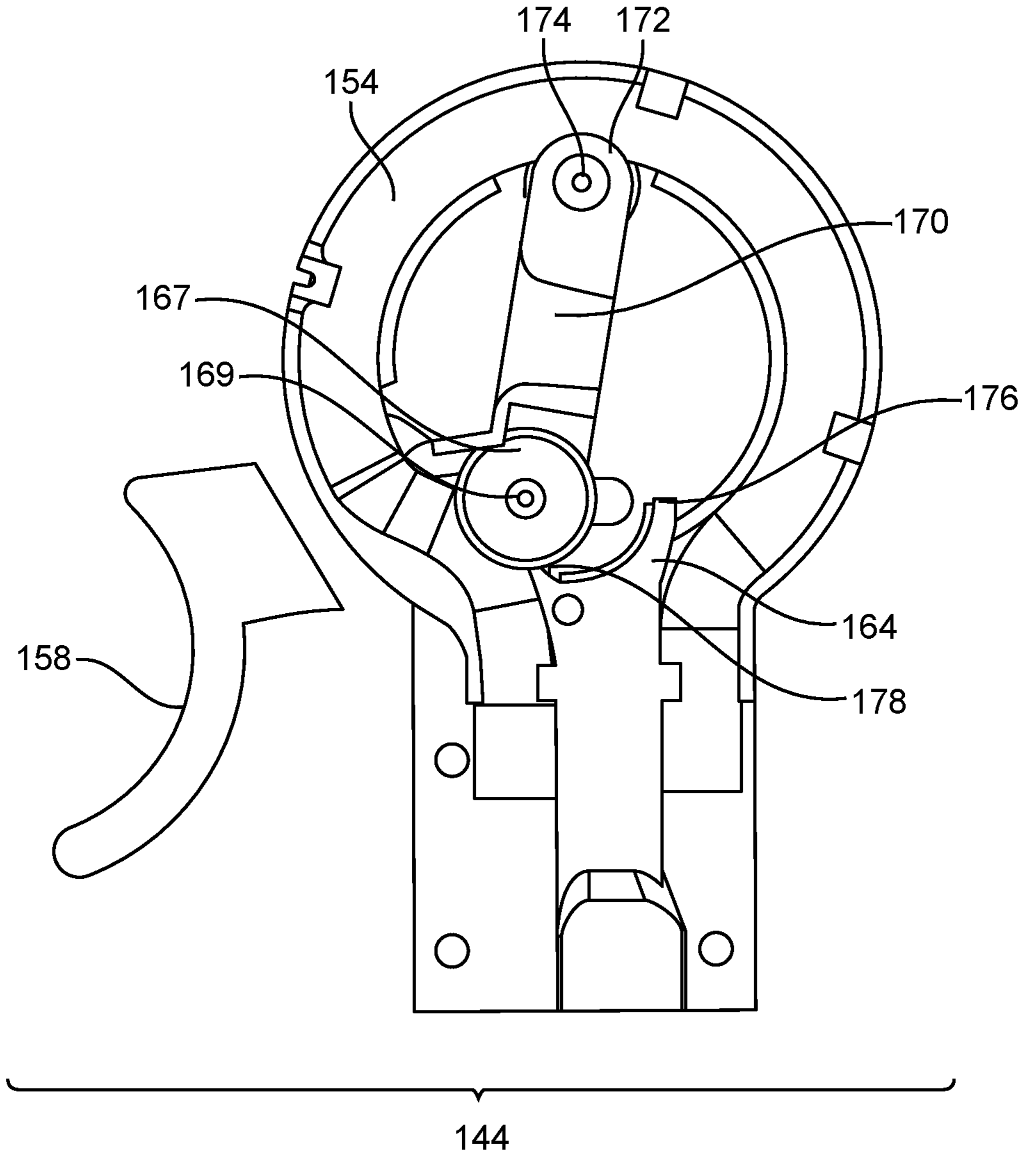
Figure 27:
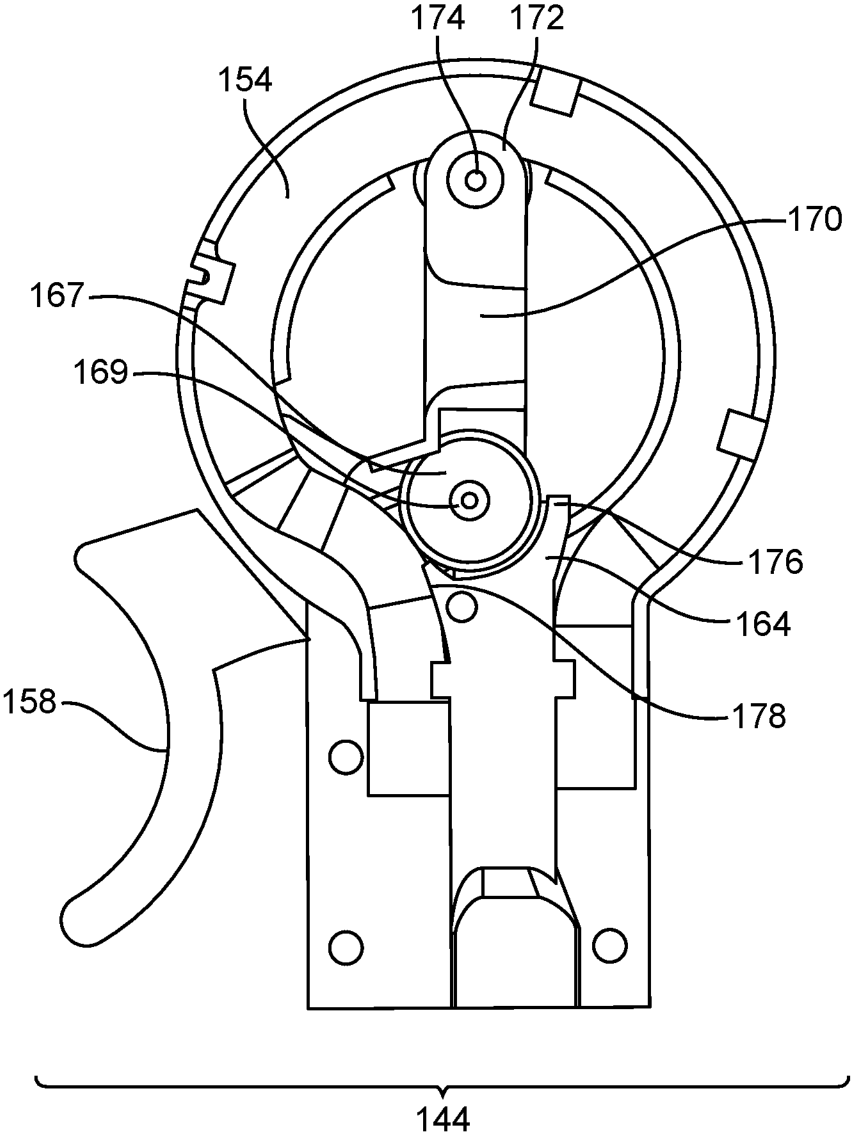

FIGS. 25-27 show successive positions of the trigger 158 for the trigger mechanism 144, from undepressed in FIG. 25 to fully depressed in FIG. 27, with corresponding movement of relevant parts. In FIG. 25, the trigger 158 is in its normal position, resulting from bias that the spring 156 or other resilient device (shown in previous Figures) applies. A roller 167 is mounted on a pin 169, at one end of a bar or lever 170. At the other end 172 of the bar or lever 170 is a mount 174 to which the bar or lever 170 is attached. With this structure, the bar or lever 170 pivots around the mount 174 when trigger 158 is depressed. Also in FIG. 25, the roller 167 is positioned away from the opening 164, which leads to a vacuum outlet (not shown). The roller 167 depresses the irrigation tube 154, closing off irrigation. Accordingly, in the trigger position shown in FIG. 25, both irrigation and vacuum are turned off. FIG. 25 further illustrates protrusions 176 and 178, the function of which is described with reference to FIGS. 26 and 27. FIG. 26 shows an intermediate position of the trigger 158, with a correspondingly intermediate position of the roller 167, closer to the opening 164. Depression of the trigger 158 causes the bar or lever 170 to rotate around the mount 174. Depression of the trigger 158 to the extent shown in FIG. 26 causes the roller 167 to come into contact with the protrusion 178, providing more resistance and signaling to the user that the trigger 158 is in an intermediate position. In this position, the roller 167 exerts less pressure on irrigation tube 154. Accordingly, in the trigger position shown in FIG. 26, vacuum still is turned off, but irrigation begins to be turned on. FIG. 27 shows a fully depressed position of the trigger 158. In this position, the user depressing the trigger 158 has caused the roller 167 to proceed over protrusion 178, to cover the opening 164, and to move farther away from the irrigation tube 154. The roller 167 moves up against the protrusion 176, signifying to the user that the trigger 158 is fully depressed. In this position, both vacuum and irrigation are turned on, so that kidney stones and/or pieces of kidney stones can be removed.

Figure 28:
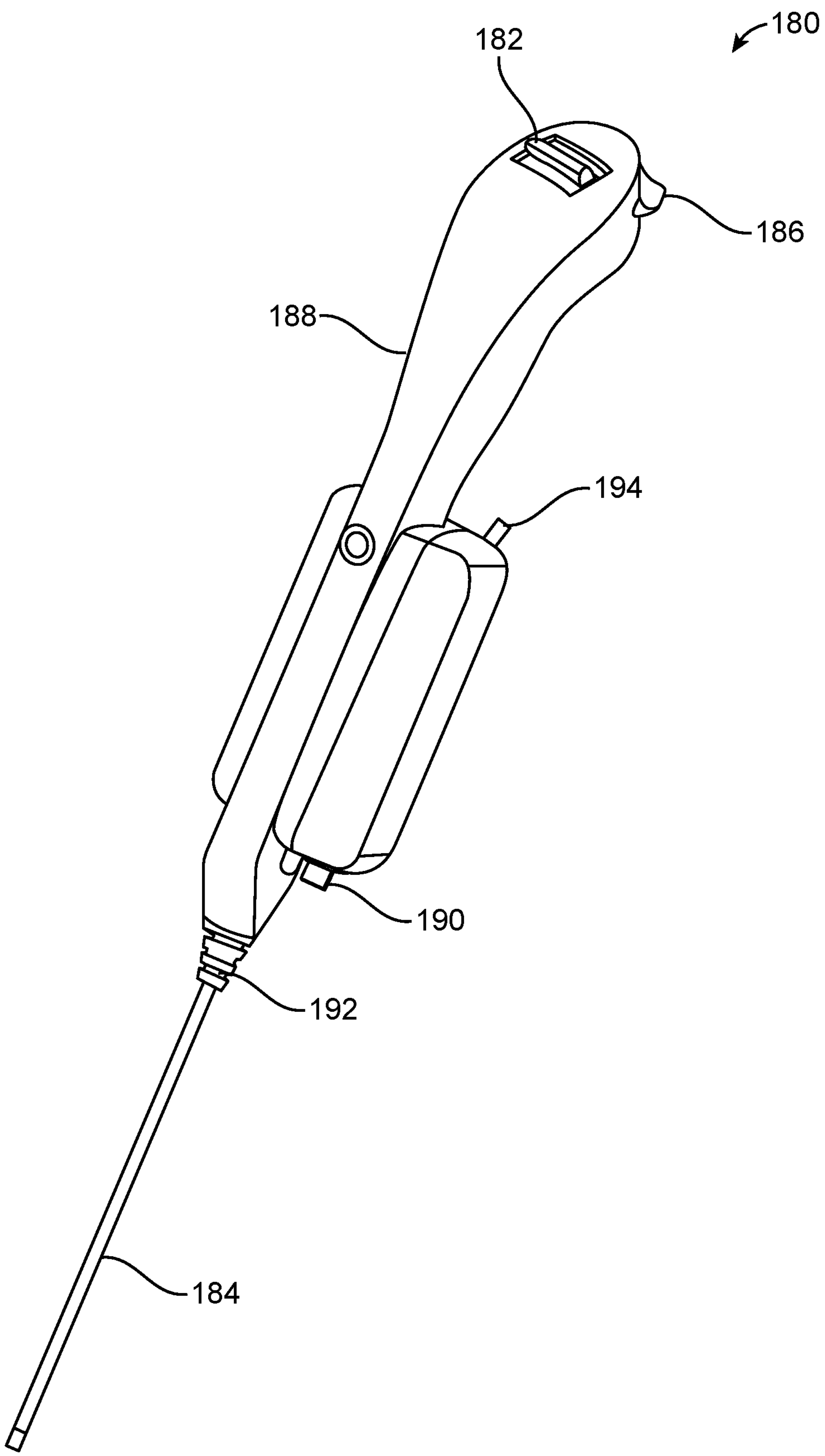
FIG. 28 shows a kidney stone treatment system according to an embodiment.
Figure 29:
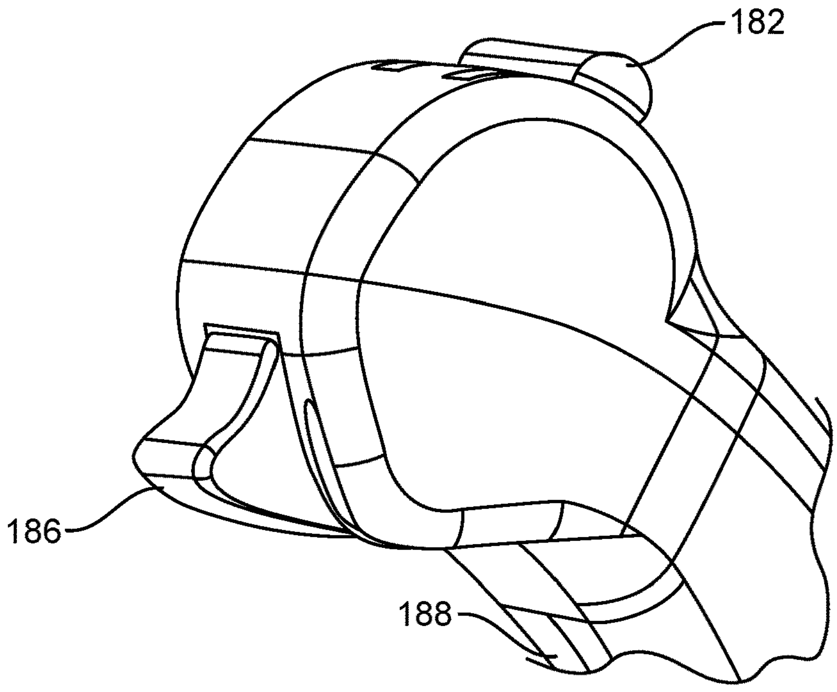
FIG. 29 shows a portion of a kidney stone removal mechanism of FIG. 28.

FIG. 28 shows a mechanism 180 for kidney stone removal according to an embodiment. In FIG. 28, a user may employ a distal tip steering control 182 to position and/or steer a catheter 184 to perform appropriate operations to break up and/or remove kidney stones. One or more pull wires (not shown) can facilitate positioning and/or steering of the catheter 184. User control of the trigger 186 controls operation of the trigger mechanism, described further herein, to control vacuum and irrigation through the catheter 184. A handle portion 188 is sized for a user to hold the mechanism 180, with the user's thumb operating the distal tip steering control 182 and one of the user's fingers operating the trigger 186. Alternatively, a user's thumb may operate the trigger 186, and a user's finger may operate the distal tip steering control 182. Also in FIG. 28, a port 190 connects to a vacuum source (not shown). The catheter 184 is attached to a catheter strain relief 192. In an embodiment, a port 194 provides access to a working channel within the catheter 184 to facilitate introduction of therapeutic tools, such as a laser, to the distal end of the catheter 184. FIG. 29 shows an enlarged view of the distal tip steering control 182 and the trigger 186, and an upper portion of the handle portion 188.

Figure 30:
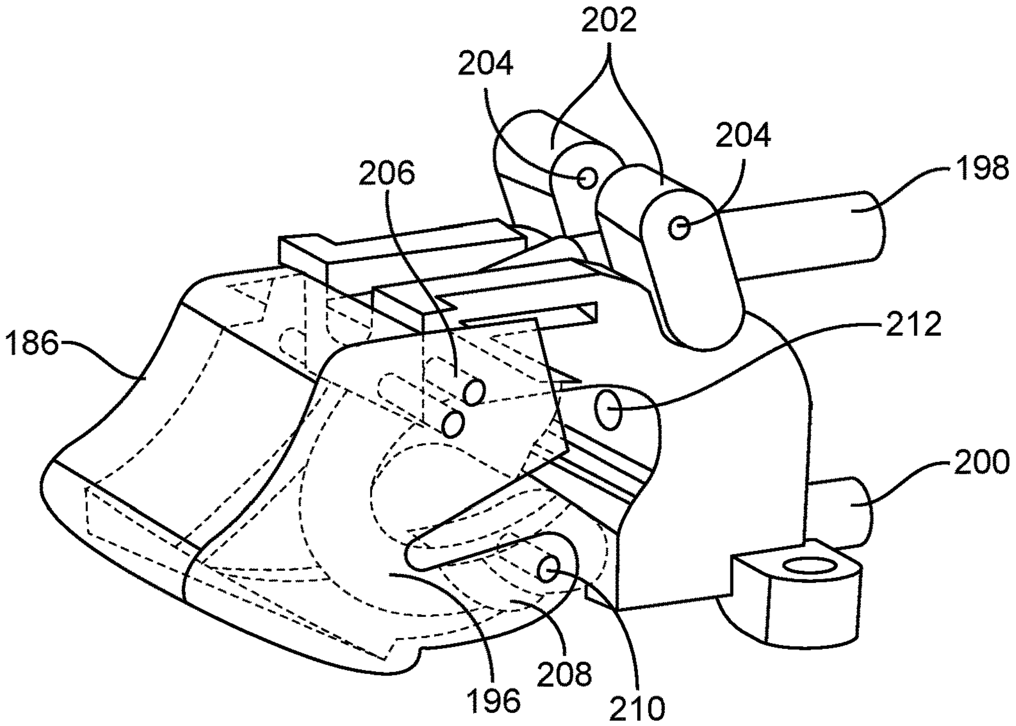
FIG. 30 shows a view of a portion of a kidney stone removal mechanism according to an embodiment.

FIG. 30 shows an example of a trigger mechanism that may be used in the embodiment of FIGS. 28 and 29. An irrigation tube 196 has inlet 198, connected to an irrigation source, and an outlet 200, connected to a distal tip (not shown) to irrigate a desired region. Posts 202 are located and sized to hold the distal tip steering control 182, which may be attached to the posts 202 via one or more pins (also not shown) passing through holes 204 in the posts 202. As part of the distal tip steering control 182, pull wires (not shown) may be provided to guide movement and position of the catheter's distal tip to perform suitable actions to maneuver the tip into proper position for a kidney stone removal procedure. Depression of the trigger 186 causes rotation of the trigger 186 around pivot pin 206, and causes a roller 208, attached via a pin 210, to move from the position shown to a location so as to cover a port 212, which is connected to ambient air via to an activation tube (not shown). That is, covering the port 212 functions in the same way as the activation pinch mechanism 96 of FIGS. 35 and 36 in that when the port 212 is covered there is no longer flow from ambient air to the vacuum source. When the port 212 is uncovered, the vacuum is off at the target area. When the port 212 is covered, the vacuum is on at the target area.

Figure 31:
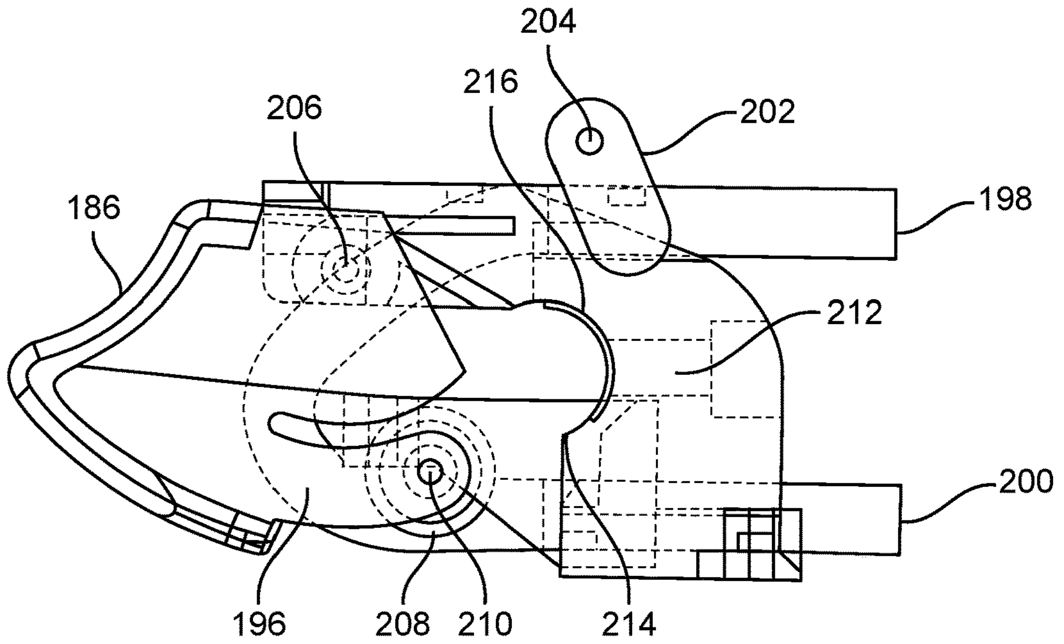
FIGS. 31 to 34 show successive positions of a trigger in the structure of FIG. 30 according to an embodiment.
Figure 32:
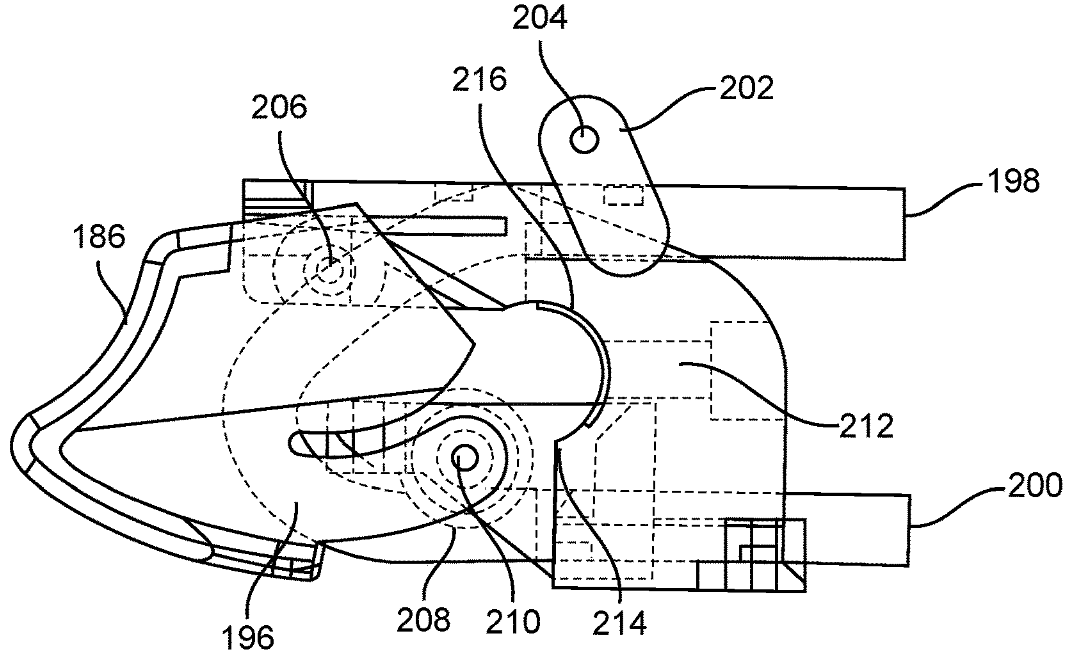
Figure 33:
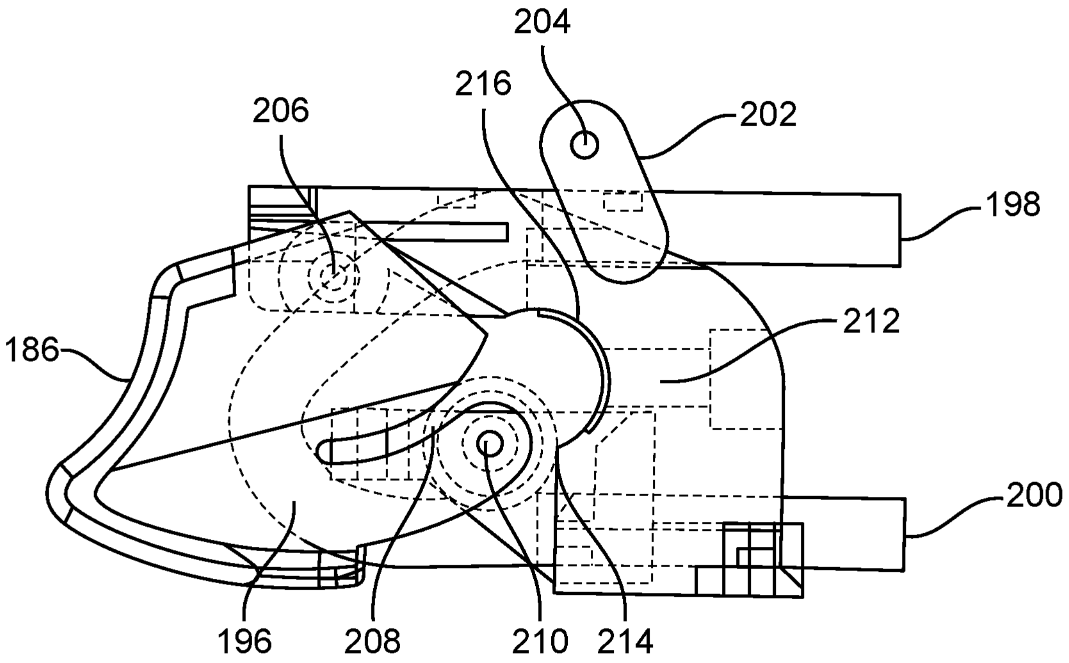
Figure 34:
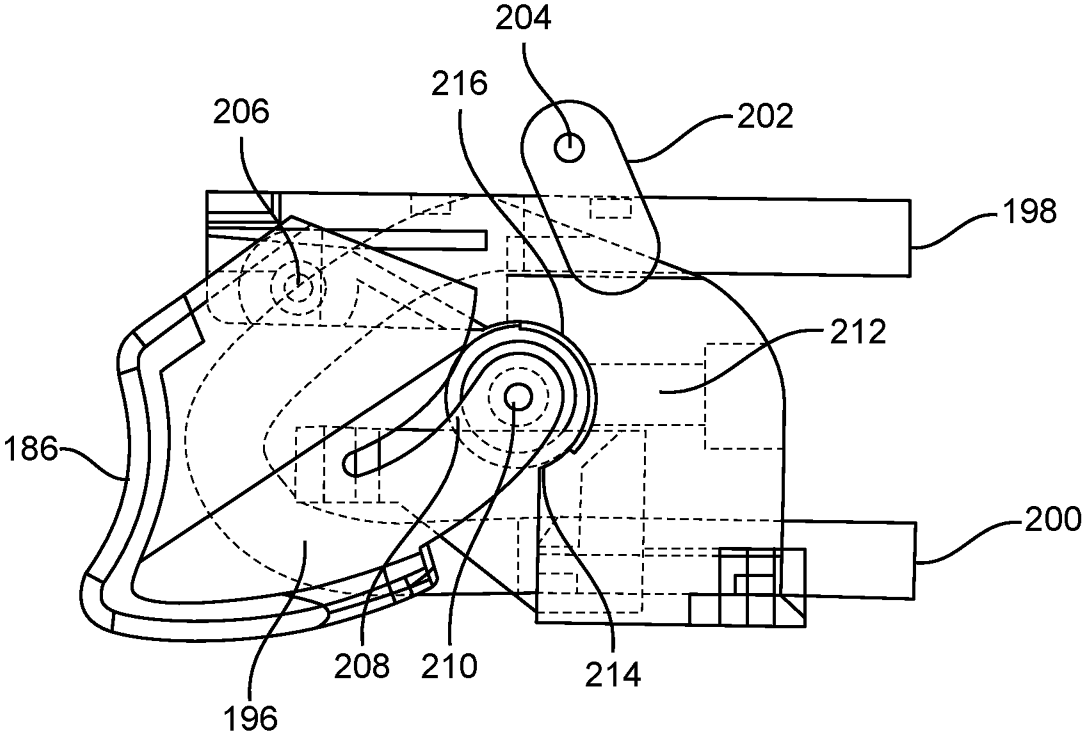

FIGS. 31-34 show progressive depressions of the trigger 186. In these figures, for ease of description, posts 202 remain in the same position, that is, the distal tip steering control 182 is not being operated. FIG. 31 shows the trigger 186 in an undepressed position. In this position, the roller 208 closes off, or at least constricts, irrigation the tube 196, while the port 212 is open. The roller 208 is set apart from a contact edge 214. This position corresponds to the vacuum and the irrigation both being turned off. In FIG. 32, initial depression of the trigger 186 causes the trigger 186 to rotate slightly to the right around the pivot pin 206, causing the roller 208 to move slightly upward and to the right. In this position, the irrigation tube 196 is opened further, allowing irrigation of the area to be treated. This positioning of the trigger 186 corresponds to an irrigation only state, with vacuum still turned off by virtue of the port 212 remaining open. In FIG. 33, further depression of the trigger 186 causes the trigger 186 to rotate slightly more to the right around the pivot pin 206, causing the roller 208 to move slightly more upward and to the right. With the roller 208 in this position, the port 212 remains open, so vacuum still is turned off. The irrigation tube 196 is squeezed less, allowing for more irrigation of the affected area. In this position, the roller 208 contacts an edge 214, which acts as a detent, according to an embodiment. When the roller 208 contacts the edge 214, the user is alerted, by virtue of encountering resistance to depression of the trigger 186. In FIG. 34, when the user overcomes the resistance at the edge 214 and depresses the trigger 186 farther, the trigger 186 rotates farther upward and to the right until the roller 208 covers the port 212. At this point, the roller 208 is seated in indentation 216, and cannot move farther. In this fashion, the user is aware that the trigger depression is at maximum. When the trigger 186 is in this position, irrigation remains on, and vacuum turns on, by virtue of the port 212 being closed (for example, performing as described in FIGS. 35 and 36).

Figure 37:
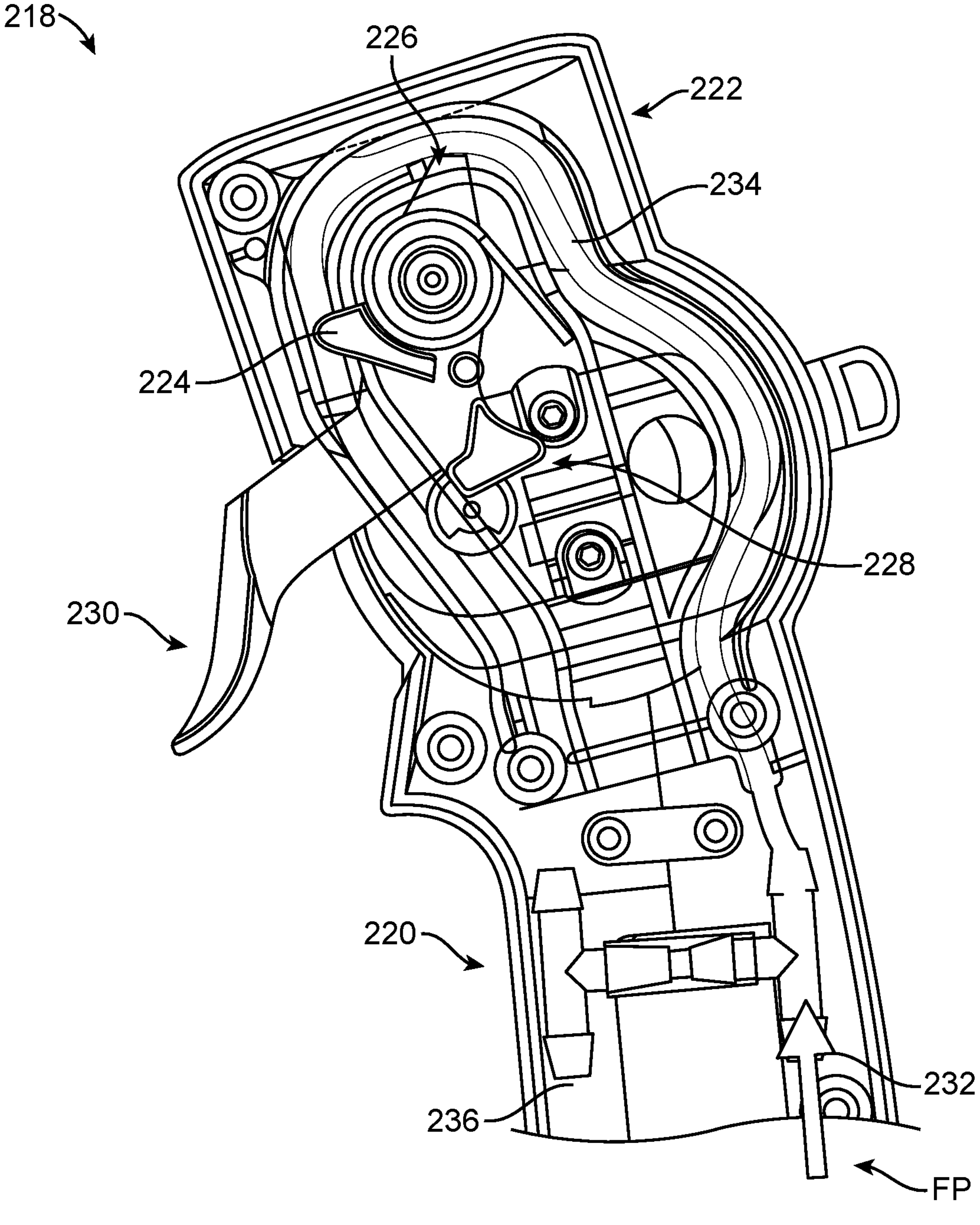
FIGS. 37 and 38 show successive positions of a trigger in a trigger activation mechanism according to an embodiment.
Figure 38:
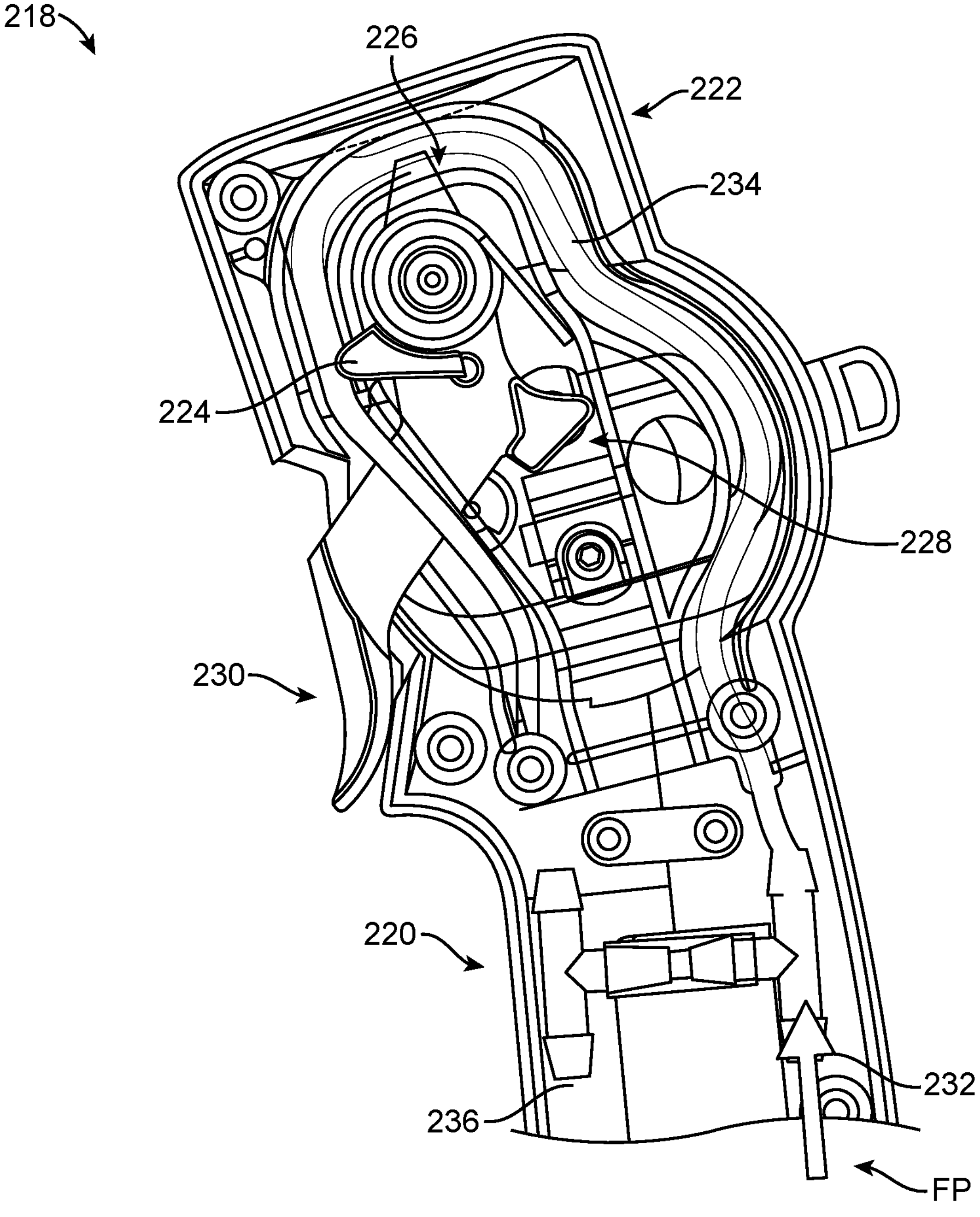

FIGS. 37 and 38 show an embodiment of a mechanism 218 that includes an irrigation bypass structure 220, which functions to always provide a minimum irrigation flow through the mechanism. The irrigation bypass structure 220 can be implemented with any of the embodiment disclosed above and is not limited to mechanism 218. FIGS. 37 and 38 show a mechanism head 222 having protrusions 224, 226, and 228, which function as disclosed in other embodiments herein to control irrigation and vacuum/suction using a single trigger 230. In some cases, the user may wish to maintain a minimum irrigation flow through the mechanism 218 without having to activate the trigger 230. In some embodiments of the mechanism disclosed herein, the protrusion 224 may be implemented such that the protrusion 224 does not completely close off the irrigation tube against which the protrusion 224 is positioned. Such an implementation may be suitable for some cases, but in other cases may not provide a sufficiently well-defined minimum flow rate. That is, the extent of the incomplete closure of the irrigation tube may vary more than is desired. FIGS. 37 and 38 provide an embodiment in which a more well-defined minimum irrigation flow can be provided through irrigation bypass structure 220 than via incomplete closure of the irrigation tube.

FIG. 37 shows a flow path FP in which most of the flow of irrigation fluid flows from an inlet 232 through an irrigation tube 234 until the flow is stopped by the protrusion 224 having closed off the irrigation tube 234 by pinching it closed. A lower amount of the flow of the irrigation fluid passes from the inlet 232 through the irrigation bypass structure 220 and to an outlet 236, which is connected to a distal end of the stone removal device. Thus, in this embodiment at least some irrigation is always flowing to the distal end of the stone removal device. FIG. 38 shows a configuration in which the trigger 230 is depressed, thereby moving the protrusion 224 away from the irrigation tube 234 and opening the irrigation tube 234. With the irrigation tube 234 open, irrigation fluid can flow along flow path FP from the inlet 232 through the mechanism head 222 and to the outlet 236. Some minor amount of irrigation fluid may still flow through the bypass structure 220, but most of the irrigation fluid flows through the mechanism head 22.

Figure 39:
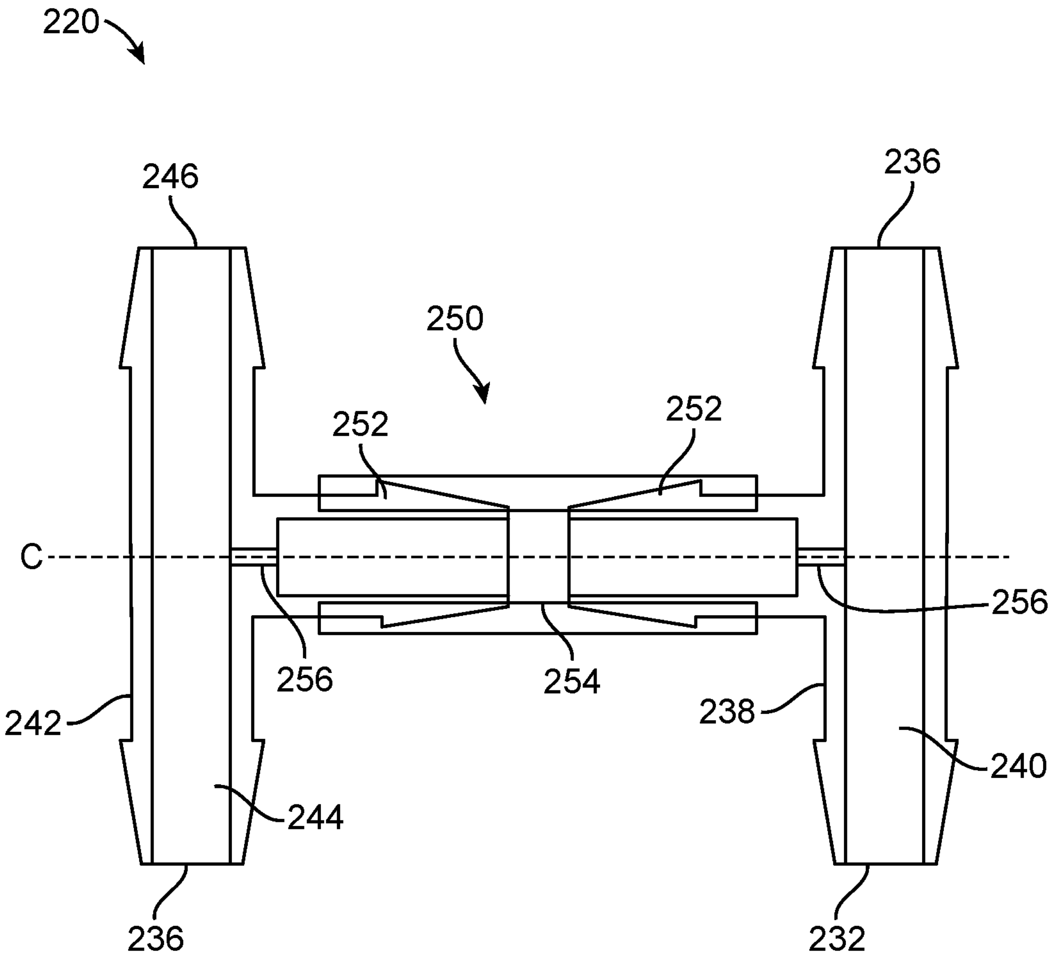
FIG. 39 shows a flow bypass structure of a mechanism according to an embodiment.

FIG. 39 shows the irrigation bypass structure 220 having an inlet tube 238 that defines an inlet lumen 240, which connects the inlet 232 with the supply outlet 236 and having an outlet tube 242 that defines an outlet lumen 244, which connects a return inlet 246 with the outlet 236. An irrigation tube (not pictured) connects the supply outlet 236 with return the inlet 246 and carries irrigation fluid through the mechanism head and trigger activation mechanism of various embodiments disclosed herein. The inlet tube 238 is connected with the outlet tube 242 by a bypass 250, which includes a pair of bypass tubes 252 connected by a bypass connector 254. FIG. 39 shows the bypass tubes 252 as hose barbs and the bypass connector 254 as tubing, but other equivalent configurations of similar structure can be used. The bypass 250 includes flow restrictions 256, which are narrow lumens (narrower than the diameter of the inlet lumen 240) that restrict the amount of irrigation fluid that can flow through the bypass 250. FIG. 39 shows two flow restrictions 256 because it may be desirable for manufacturing efficiency to produce two of the same parts and connect them via the connector 254 to form irrigation bypass structure 220, but a single flow restriction 256 can be sufficient to provide the function of the irrigation bypass structure 220 as disclosed herein. In some embodiments, the inner diameter of the flow restriction 256 can be in the range of about 5% to about 30% of the inner diameter of the inlet lumen 240 and in some embodiments about 20% of the inner diameter of inlet 240. For example, the flow restriction 256 can have an inner diameter of about 0.5 mm when the inlet lumen 240 has an inner diameter of about 2.5 mm. Other specific inner diameters within the percentage ranges disclosed are within the scope of the bypass structure. As flow rate varies to the fourth power of diameter, the ratio of the inner diameters of the flow restriction 256 and the inlet lumen 240 directly influence the ration of the flow rate through the trigger mechanism and through the bypass structure. Other factors, such as surface tension and pressure drop, may influence the extent to which the flow rate is dominated by this power law relationship.

Figure 40:
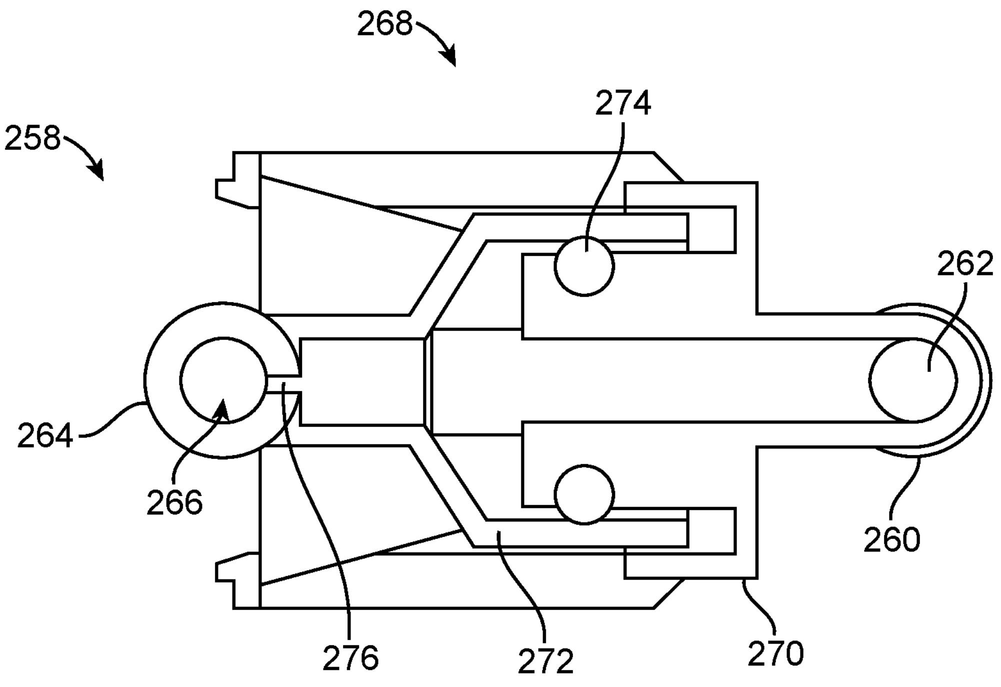
FIG. 40 shows a cross section of a flow bypass structure of a mechanism according to an embodiment.

FIG. 40 shows an irrigation bypass structure 258 of an alternate embodiment viewed in cross section defined by a plane along line C in the embodiment of similar irrigation bypass structure 220. This bypass structure can be implemented with any of the embodiments disclosed above. The irrigation bypass structure 258 includes an inlet tube 260, which defines an inlet lumen 262, and an outlet tube 264, which defines an outlet lumen 266. These lumens are connected by an irrigation tube (not pictured) that carries irrigation fluid through mechanism heads and trigger activation systems disclosed herein. FIG. 40 shows that the inlet lumen 262 and the outlet lumen 266 are also connected by a bypass 268, which is formed by a first bypass fitting 270 and a second bypass fitting 272. The first bypass fitting 270 and the second bypass fitting 272 connect via complementary features and form a fluid tight seal via O-ring 274. When connected, the first bypass fitting 270 and the second bypass fitting 272 form a conduit for fluid bypass, and this conduit include a flow restriction 276 that has a lumen narrower than the inlet lumen 262. Thus, the irrigation bypass structure 258 functions to provide a well-defined minimum irrigation flow rate when the irrigation tube in the mechanism head is closed by the trigger mechanism.

Figure 41:
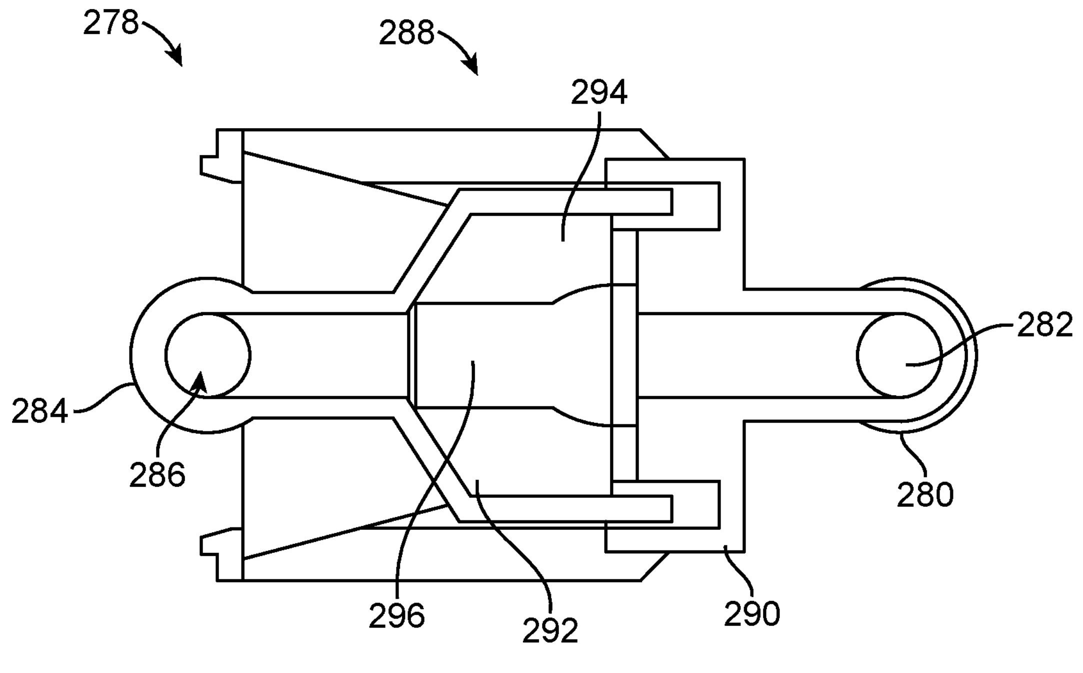
FIG. 41 shows a cross section of a flow bypass structure of a mechanism according to an embodiment.

FIG. 41 shows an irrigation bypass structure 278 of another alternate embodiment viewed in cross section defined by a plane along line C in the embodiment of similar irrigation bypass structures 220 and 258. This bypass structure can be implemented with any of the embodiments disclosed above. The irrigation bypass structure 278 includes an inlet tube 280, which defines an inlet lumen 282, and an outlet tube 284, which defines the outlet lumen 286.

These lumens are connected by an irrigation tube (not pictured) that carries irrigation fluid through mechanism heads and trigger activation systems disclosed herein. FIG. 41 shows that the inlet lumen 282 and the outlet lumen 286 are also connected by a bypass 288, which is formed by a first bypass fitting 290 and a second bypass fitting 292. The first bypass fitting 290 and the second bypass fitting 292 connect via complementary features and form a fluid tight seal via compressible member 294, which is formed of a resiliently flexible material and includes an interior flow restriction 296. The compressible member 294 is similar to an O-ring or grommet in shape or function in that it provides a fluid tight seal, but it also provides a lumen in the form of the flow restriction 296, which takes a predefined diameter when the first bypass fitting 290 and the second bypass fitting 292 are connected. This predefined diameter of flow restriction 6664 is narrower than the diameter of the inlet lumen 282. Thus, the irrigation bypass structure 278 functions to provide a well-defined minimum irrigation flow rate when the irrigation tube in the mechanism head is closed by the trigger mechanism.

Figure 42:
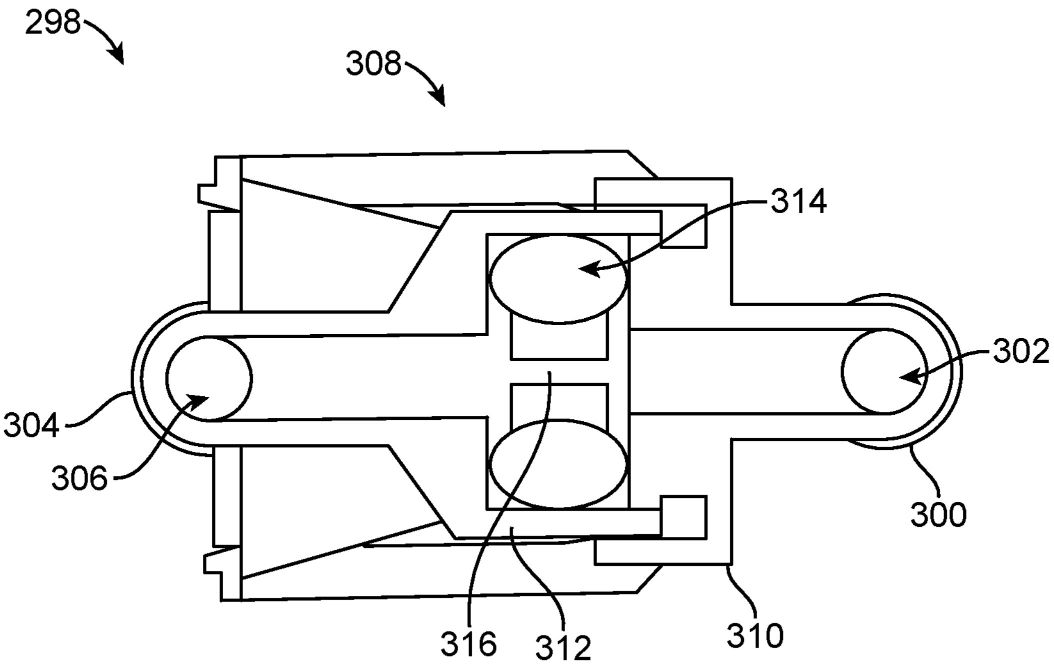
FIG. 42 shows a cross section of a flow bypass structure of a mechanism according to an embodiment.

FIG. 42 shows an irrigation bypass structure 298 of another alternate embodiment viewed in cross section defined by a plane along line C in the embodiment of similar irrigation bypass structures 220, 258, and 278. This bypass structure can be implemented with any of the embodiments disclosed above. The irrigation bypass structure 298 includes an inlet tube 300, which defines inlet lumen 302, and an outlet tube 304, which defines outlet lumen 306. These lumens are connected by an irrigation tube (not pictured) that carries irrigation fluid through mechanism heads and trigger activation systems disclosed herein. FIG. 42 shows that the inlet lumen 302 and the outlet lumen 306 are also connected by a bypass 308, which is formed by a first bypass fitting 310 and a second bypass fitting 312. The first bypass fitting 310 and the second bypass fitting 312 connect via complementary features and form a fluid tight seal via O-ring 314, which is formed of a resiliently flexible material. The second bypass fitting 312 also includes an interior flow restriction 316, which has a diameter narrower than the diameter of the inlet lumen 300. Thus, irrigation bypass structure 298 functions to provide a well-defined minimum irrigation flow rate when the irrigation tube in the mechanism head is closed by the trigger mechanism.

The various flow control mechanisms and bypass structures described herein can alternatively reside in a separate unit from the handle of the device. In this scenario, a flexible irrigation tube and a flexible vacuum line connect the separate unit with the handle. The separate unit can be controlled by the user via foot pedals, a touchscreen, or other similar activation mechanisms. The mechanisms in the separate unit can be controlled mechanically, electro-mechanically, electromagnetically, or by other similar control methods. In one example, the separate unit is a reusable unit, similar to or included with the control unit 18. In this example, control unit 18 provides irrigation fluid and negative pressure to the system in addition to imaging control.

Figure 43:
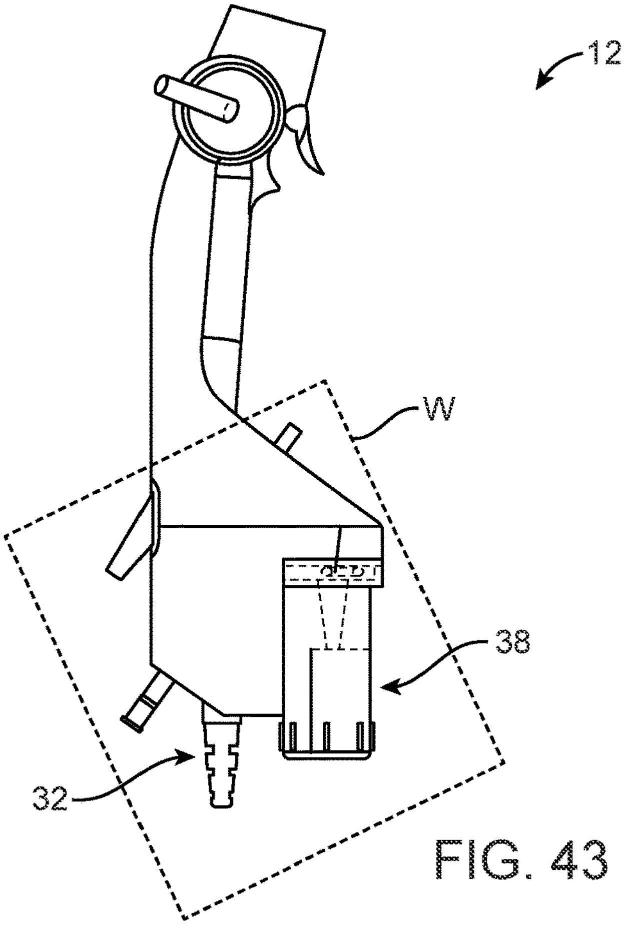
FIG. 43 is a view of a kidney stone removal mechanism according to an embodiment.
Figure 44:
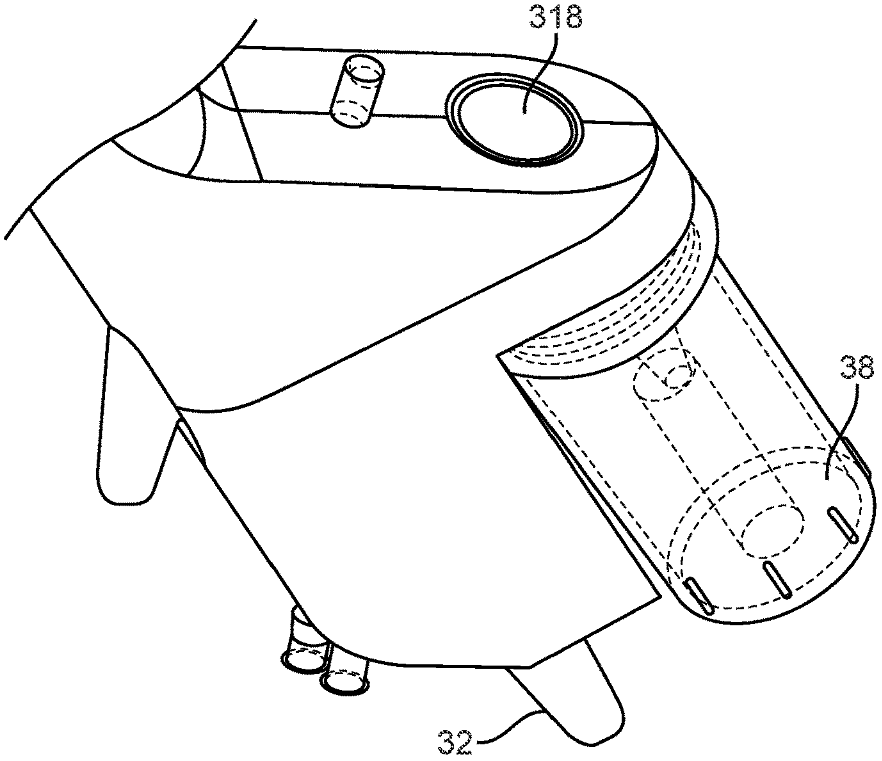
FIG. 44 is a rotated and enlarged view of a portion a kidney stone removal mechanism according to an embodiment.

FIG. 43 shows the mechanism 12 for effecting kidney stone removal according to an embodiment. The lower portion of the mechanism includes the stone catcher receptacle 38 in fluid communication with the vacuum inlet 32. FIG. 44 is a rotated and enlarged view of the mechanism 12 inside box W of FIG. 43 and shows the location on mechanism 12 of a flow indicator 318. The flow indicator 318 provides a visual (and optionally audible) indication of whether air and/or fluid is flowing through mechanism 12 and out to the vacuum inlet 32. The absence of fluid flow through mechanism 12 can indicate that there is a clog somewhere in the fluid path within the stone removal device. The clog could be in the catheter section or in the mechanism 12, and it can be important to address such a clog to prevent overpressure in the kidney caused by continuing to irrigate the kidney in the presence of a clog.

Figure 45:
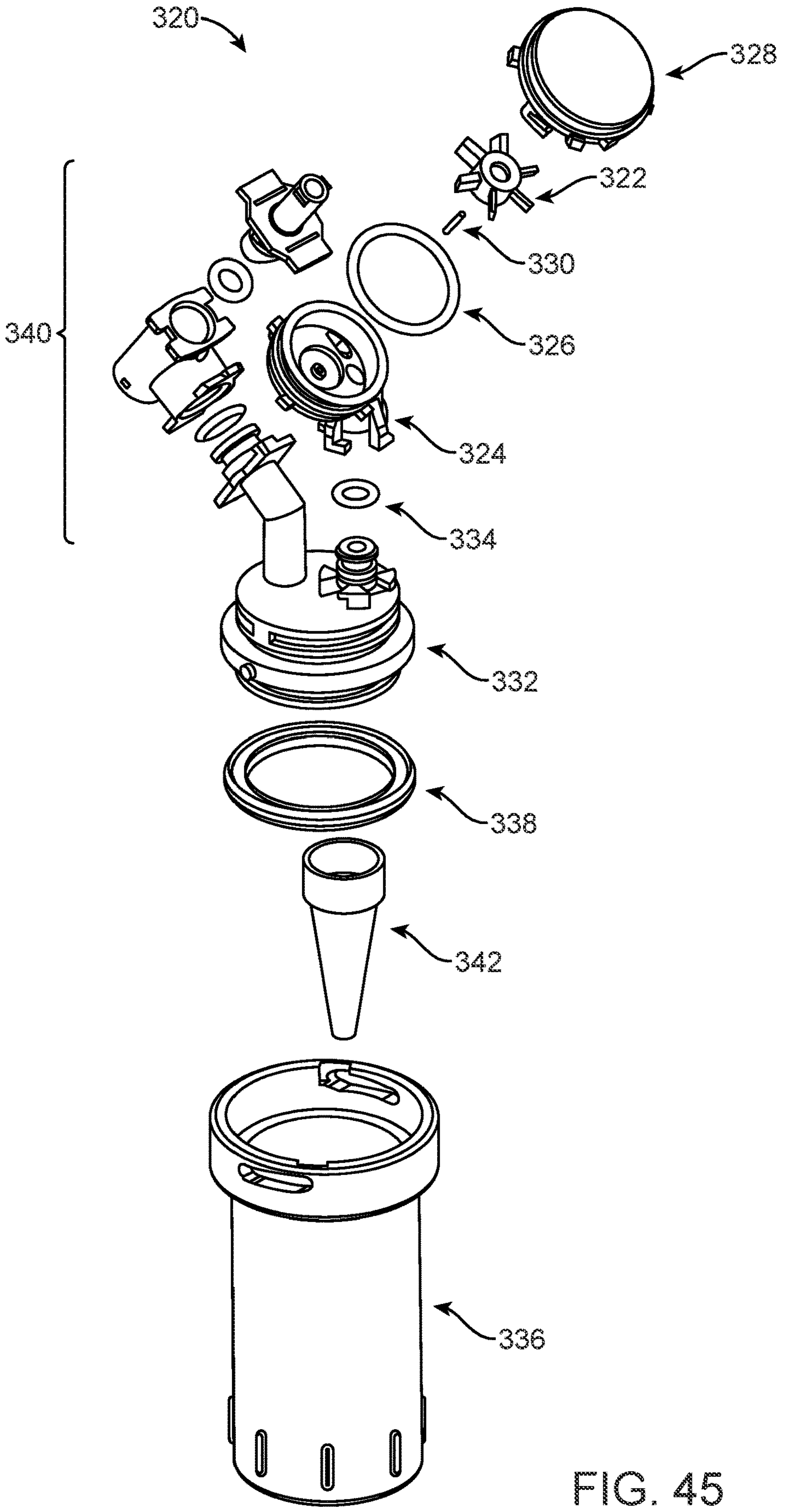
FIG. 45 is an exploded view of a stone catcher assembly according to an embodiment.

FIG. 45 is an exploded view of a stone catcher assembly 320 that is configured to be part of mechanism 12 and can be implemented with any of the above-described embodiments. A flow indicator 322 is contained within a flow indicator housing 324 with an O-ring 326 that seals the flow indicator housing 324 with a flow indicator cover 328, which is transparent or translucent such that a user can observe the movement of the flow indicator 322. An axle 330 allows the flow indicator 322 to rotate in the presence of flow. Alternate configurations of flow indicators are within the scope of this disclosure, such as any configuration that moves visibly in response to flow within a housing. The flow indicator housing 324 is connected to a stone catcher receptacle cap assembly 332 by a fluid tight seal, such as with an O-ring 334. The stone catcher receptacle cap assembly 332 is connected with a stone catcher receptacle 336 via a stone catcher receptacle seal 338. The stone catcher receptacle cap assembly 332 is also connected with an inflow assembly 340. In use, the direction of flow of fluid (including kidney stone debris) in the stone catcher assembly 320 is through inflow assembly 340, which is connected to the catheter section of the stone removal device, and to the stone catcher receptacle 336. Fluid and air are drawn up through stone catcher receptacle filter 342, which keeps debris within the stone catcher receptacle 336, but allows fluid and air to pass through and eventually into the flow indicator housing 324 to interact with the flow indicator 322. Thus, the flow indicator 322 is unlikely to become jammed or stuck with kidney stone debris. In any embodiment of a flow indicator, the flow indicator should be protected from having its movement stopped by debris interacting with the flow indicator itself.

Figure 46:
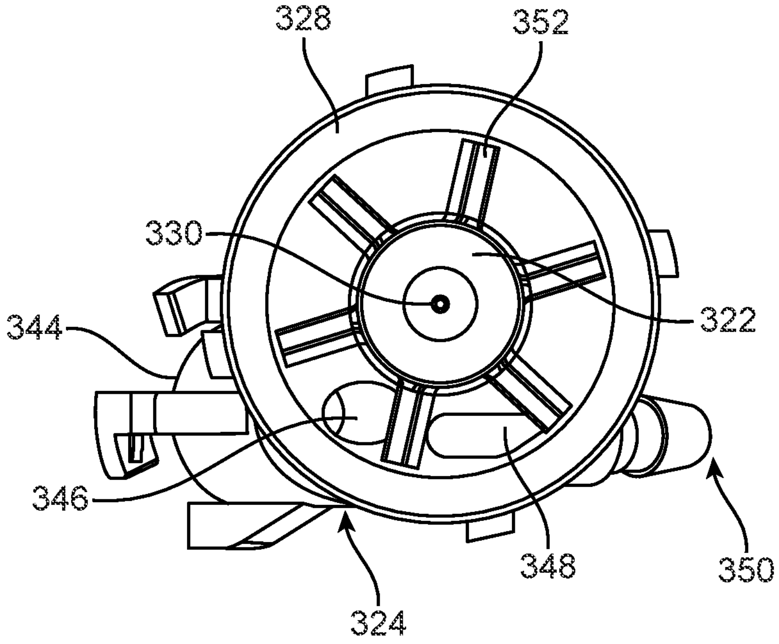
FIGS. 46 and 47 are two views of a flow indicator mechanism according to an embodiment.
Figure 47:
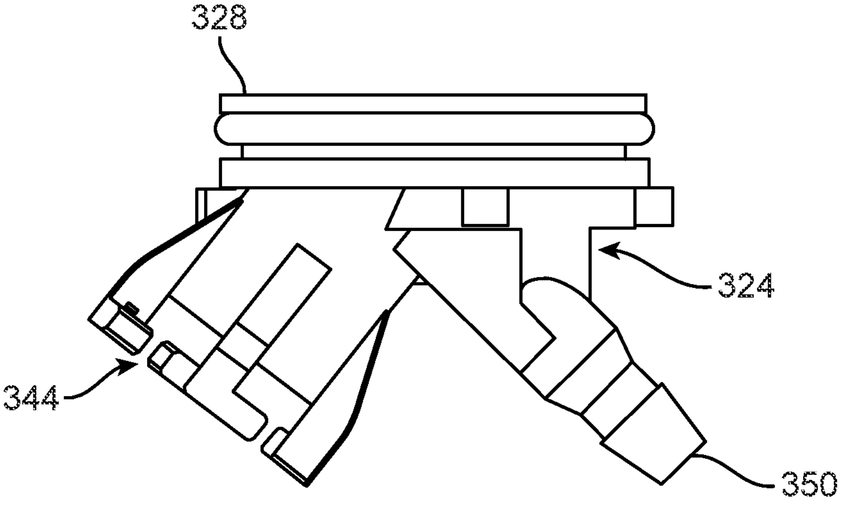

FIGS. 46 and 47 are two views of the flow indicator mechanism that includes the flow indicator 322 positioned in the flow indicator housing 324. Fluid from the stone catcher receptacle 336 enters the flow indicator housing 324 via a flow inlet 344, which is connected with an indicator inlet 346 to introduce fluid into the flow indicator housing 324 to interact with the flow indicator 322. Fluid exits the flow indicator housing 324 via an indicator outlet 348 connected with a flow outlet 350. The flow indicator 322 includes at least two flow indicator vanes 352 that interact with fluid as it moves from the indicator inlet 346 to the indicator outlet 348. The movement of fluid between the indicator inlet 346 to the indicator outlet 348 pushes on the flow indicator vanes 352 and creates movement of the flow indicator 322 by causing it to rotate around the axle 330. The indicator inlet 346 and the indicator outlet 348 can be positioned and various places in the flow indicator housing 324 such that the fluid flow interacts with more than one flow indicator vane 352 on the path between the indicator inlet 346 to the indicator outlet 350.

The flow indicator embodiments disclosed herein are one approach to preventing overpressure in the device and/or in the anatomy during a kidney stone removal procedure. In addition to or in place of a flow indicator, mechanisms and devices disclosed herein may include a pressure relief valve capable of relieving fluid pressure when the fluid pressure exceeds a certain predetermined safety threshold. A pressure relief valve may be included on the mechanism handle, on the catheter, at the junction between the handle and the catheter, on the fluid supply line, and/or at the junction of the fluid supply line and handle.

The handle mechanism 12 can be fitted with a variable flow mechanism operable for controlling the rate or volume of irrigate and suction applied during the treatment process. The variable flow mechanism can control one or a combination of active irrigation flow, passive irrigation flow, active vacuum flow, and passive vacuum flow. The control of each can be independent. In one embodiment, active application of irrigation fluid and vacuum is caused by operation of the trigger mechanism with the intent to applying irrigation fluid and suction at a greater rate or amount than the rate or amount applied during passive application. In some embodiments, passive application of irrigation fluid and vacuum can be produced without the operation of the trigger mechanism and active application is produced only by operation of the trigger mechanism. The variable control mechanism can act on or manipulate the irrigation lumen or any other secondary lumen (e.g., by-pass lumen) in communication with the irrigation lumen. The variable control mechanism can also act on or manipulate the vacuum lumen or any other secondary lumen in communication with the vacuum lumen. The variable flow mechanism can allow for adjusting or controlling the flow rate or amount of discharged irrigation fluid with respect to the suction rate or amount of applied vacuum. For irrigation, the variable flow mechanism can have one or more low irrigation flow settings and one or more high irrigation flow settings or a series of settings from low, to intermediate, to high. During navigation of the endoscope a user can implement one of the lower irrigation flow settings, and during removal of kidney stones a suitably higher irrigation flow setting can be activated. Similarly, the variable flow mechanism can have one or more low vacuum suction settings and one or more high vacuum suction settings or a series of settings from low, to intermediate, to high. One of the lower vacuum suction settings can be used during laser fragmentation of kidney stones. After laser fragmentation, and for example when then the laser is removed, a suitably higher vacuum suction settings can be activated for maximizing removal of the fragmented kidney stones. The variable flow mechanism can also include an off-function for the irrigation and vacuum. This will allow the vacuum to be off during some applications of irrigation fluid to prevent discharged irrigation fluid from being removed. The variable flow mechanism can be used in conjunction with all the embodiments described above (e.g., flow indicator, etc.).

Figure 48A:
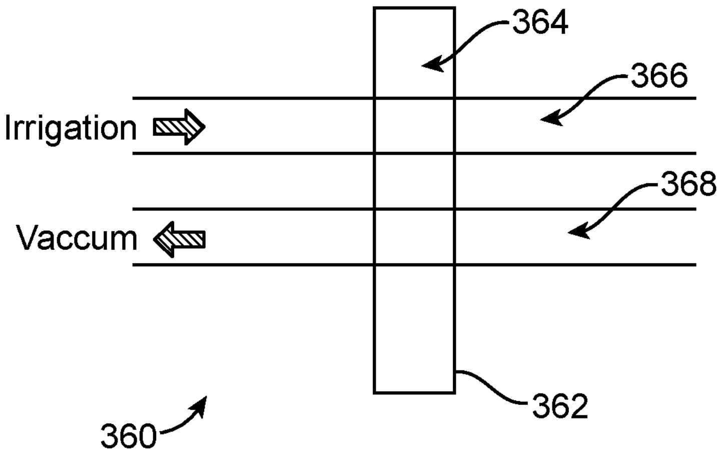
FIGS. 48A, 48B (front view of valve), and 48C (cross-sectional view of valve) illustrate an embodiment of a variable flow mechanism for controlling the rate or volume of irrigation and suction applied during the treatment process.
Figure 48B:
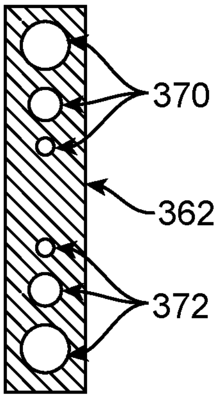
Figure 48C:
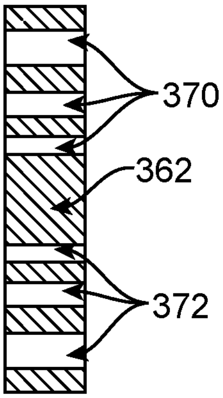

Referring to FIGS. 48A, 48B (front view), and 48C (cross-sectional view), a variable flow mechanism 360 is illustrated that can be operated by a user via the handle mechanism 12. The variable flow mechanism 360 can be a trumpet- or piston-type valve 362 operable within a valve cylinder 364 to provide a number of different apertures having similar or different sizes that can intersect with irrigation and vacuum lumens 366 and 368. The aperture sizes dictate the amount or flow rate of irrigation fluid and suction. The piston valve 362 is illustrated as having three valve irrigation ports 370 that can align with the irrigation lumen 366 and three valve vacuum ports 372 that can align with the vacuum lumen 368, where the larger sized holes provide a higher irrigation and suction rate or amount than the smaller sized holes. In FIGS. 48B and 48C, the irrigation ports 370 are shown from larger to smaller in descending order, and the vacuum ports are shown from larger to smaller in ascending order. This means that when the largest irrigation port 370 is aligned with the irrigation lumen 366, the smallest vacuum port 372 is aligned with the vacuum lumen 368, and when the smallest irrigation port 370 is aligned with the irrigation lumen 366, the largest vacuum port 372 is aligned with the vacuum lumen 368. Thus, the highest irrigation setting correlates to the lowest vacuum setting, and conversely the lowest irrigation setting correlates with the highest vacuum setting. In other embodiments of the invention, the ports 370 and 372 can be sized and arranged in a different pattern and configuration than that shown in FIGS. 48A and 48C. In other embodiment, an array of cylinders 364 can be provided, each housing a piston valve 362 having any number of port sizes and configurations. The valve array can provide more settings for controlling the rate or amount of irrigation and suction. Each valve of the valve array can be operable in synchronicity or independently to provide variable irrigation flow and suction control.

Figure 49A:
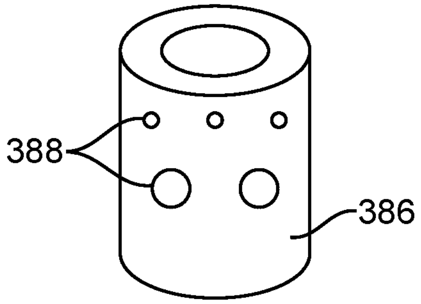
FIGS. 49A and 49B illustrate an embodiment of a variable flow mechanism for controlling the rate or volume of irrigation and suction applied during the treatment process.
Figure 49B:
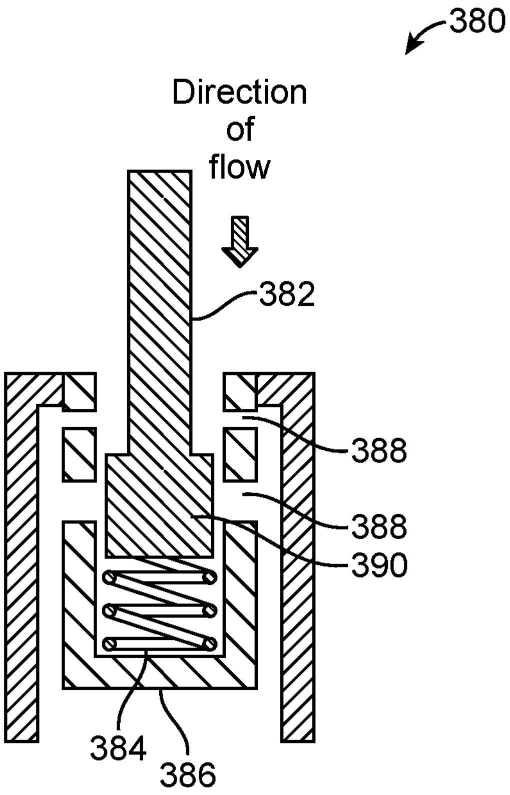

FIGS. 49A and 49B illustrate another variable flow mechanism 380 in the configuration of a spring-loaded button valve design. A plunger shaft 382 is configured to bias back-and-forth, by application and removal of pressure via biasing element 384, in a cylindrical housing 386. The cylindrical house 386 has apertures 388 of different sizes in communication with the irrigation and vacuum lumens. A head 390 of the plunger shaft 382 blocks and unblocks the apertures 388 for controlling the level of irrigation and suction to the irrigation and vacuum lumens. In the neutral or home position (no pressure applied the plunger shaft 382), the head 390 can block the larger holes and allow for passive flow of irrigation fluid and/or vacuum via the smaller apertures 388. The actuation of the plunger shaft 382 causes the larger holes 388 to gradually open, thereby increasing the rate or amount of irrigation flow and/or suction. Maximum flow and/or suction can be achieved when the head 390 is completely disengaged from the larger apertures 388. A single unit can be used, or multiple units can be place serially with multiple plungers operable in synchronicity or independently to provide variable irrigation and suction control.

Figure 50A:
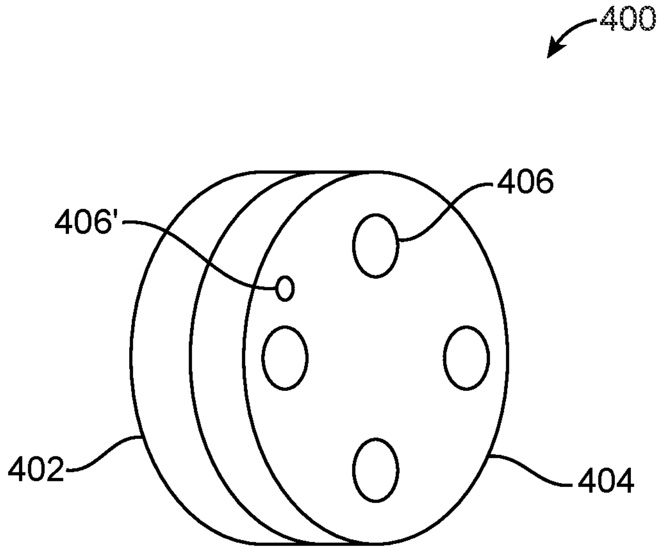
FIGS. 50A, 50B, 50C, and 50*d* illustrate an embodiment of a variable flow mechanism for controlling the rate or volume of irrigation and suction applied during the treatment process.
Figure 50B:
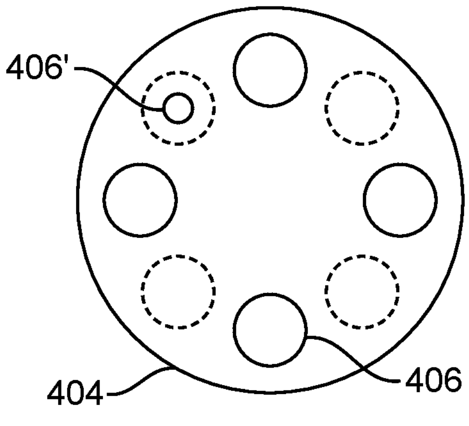
Figure 50C:
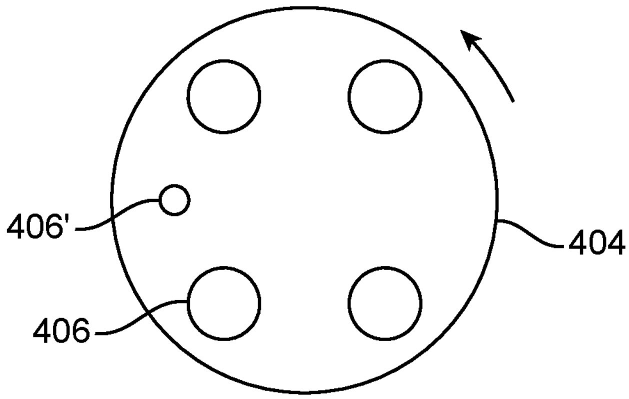
Figure 50D:
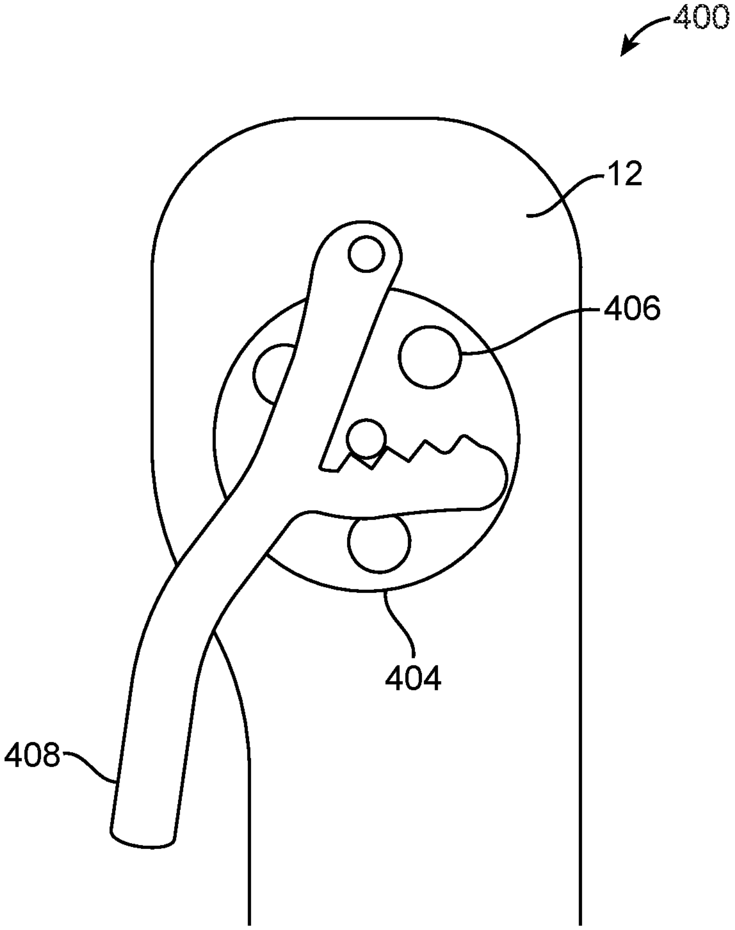

FIGS. 50A, 50B, and 50C illustrate another variable flow mechanism 400 in the configuration of rotating plates 402 and 404. The rotating plates 402 and 404 include apertures 406 of different sizes. The rotating plates are in communication with irrigation and vacuum lumens, and the alignment of the apertures 406 with these lumens allows control over the level of irrigation and/or suction. In the passive state (e.g., low irrigation flow), at least one small hole 406' allows for fluid to pass through the plates 402 and 404. In this state, the hole 406 that allows for suction to be applied can be blocked, for example. In the active irrigation state, one plate is turned for the alignment of the larger holes, thus increasing the irrigation and/or vacuum levels. Additionally, holes of plate 402 can be of different sizes than holes of plate 404, the alignment of which can create different contemporaneous levels of irrigation relative to vacuum. For example, the alignment can create an irrigation hole that is greater than the vacuum hole, or vise-versa. The concentric plates 402 and 404 can be "thumbwheel" type that allows a user to rotate one of the plates with the use of a finger while the other plate is stationary. Rotating a single plate 402 or 404 can provide variable levels of irrigation and suction in the lumens with which the plates 402 and 404 communicate. Alternatively, as illustrated in FIG. 50D a lever type mechanism 408 can be incorporated into the handle mechanism 12 for rotation of one of the plates while the other plate is stationarily affixed to the handle mechanism 12 and this lever-driven rotation provides variable levels of irrigation and suction in the lumens with which the plates 402 and 404 communicate.

Figure 51A:
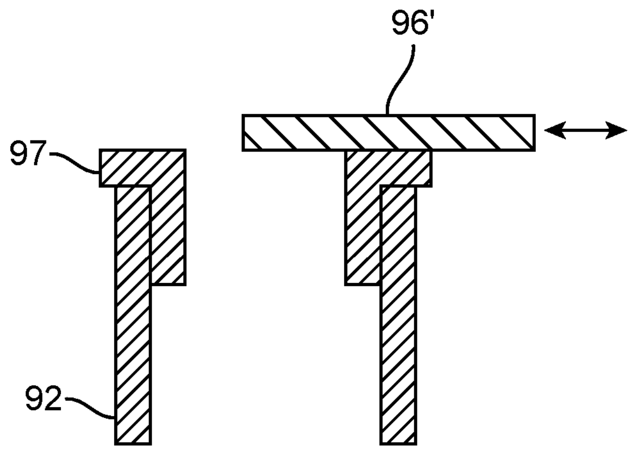
FIGS. 51A and 51B show schematic diagrams of a vacuum/suction control system and method according to an embodiment.
Figure 51B:
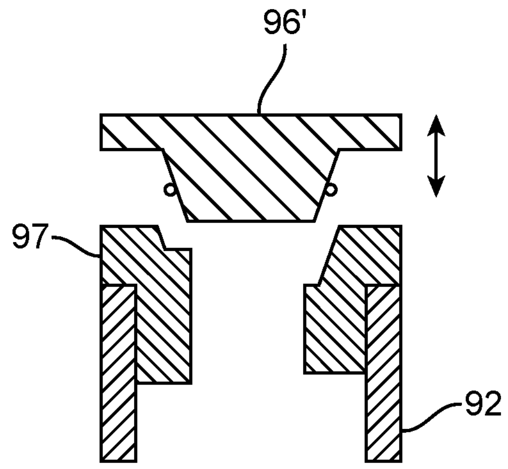
Figure 52A:
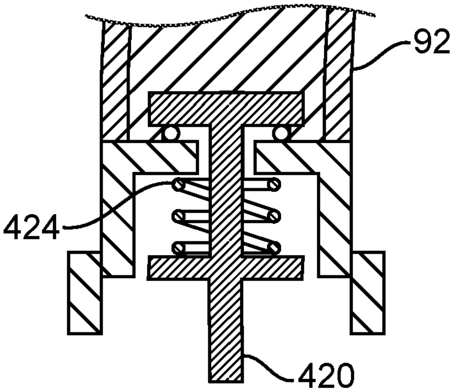
FIGS. 52A and 52B show schematic diagrams of a vacuum/suction control system and method according to an embodiment.
Figure 52B:
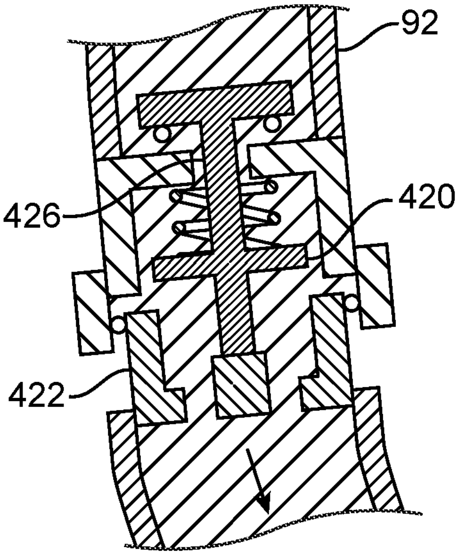

Referring back to FIGS. 35 and 36, schematic diagrams of a vacuum/suction control system and method was described in which the activation pinch mechanism 96 controlled vacuum/suction flow. The activation pinch mechanism 96 is positioned adjacent to the activation tube 92 and is movable in the direction of arrow P from first position that allows flow in the direction of arrow B through the activation tube 92 (shown in FIG. 35) and a second position that prevents flow from activation opening 94 through activation tube 92 (shown in FIG. 36). In an alternative embodiment, as illustrated by FIG. 51A, a slidable cap member 96' can be used instead of the pinch mechanism 96. The trigger mechanism or other actuator slides the cap member 96' (illustrated horizontally) over cap receiving member 97 for activating/deactivating the vacuum. In FIG. 51B, the cap member 96' in insertable into and out of the cap receiving member 97 (e.g., slidable vertically) by operation of the trigger mechanism. In FIGS. 52A and 52B, the activation pinch mechanism 96 is replaced by a spring-loaded valve 420 positioned within the activation tube 92. The spring-loaded valve 420 is similar to a bicycle tire valve which would be engageable and disengageable by a user to activate and deactivate the vacuum flow. A trigger pull or other actuation mechanism (not illustrated) can engage the connection part 422 for enabling vacuum by biasing a spring 424 to push the valve's head away from opening 426.

Figure 53:
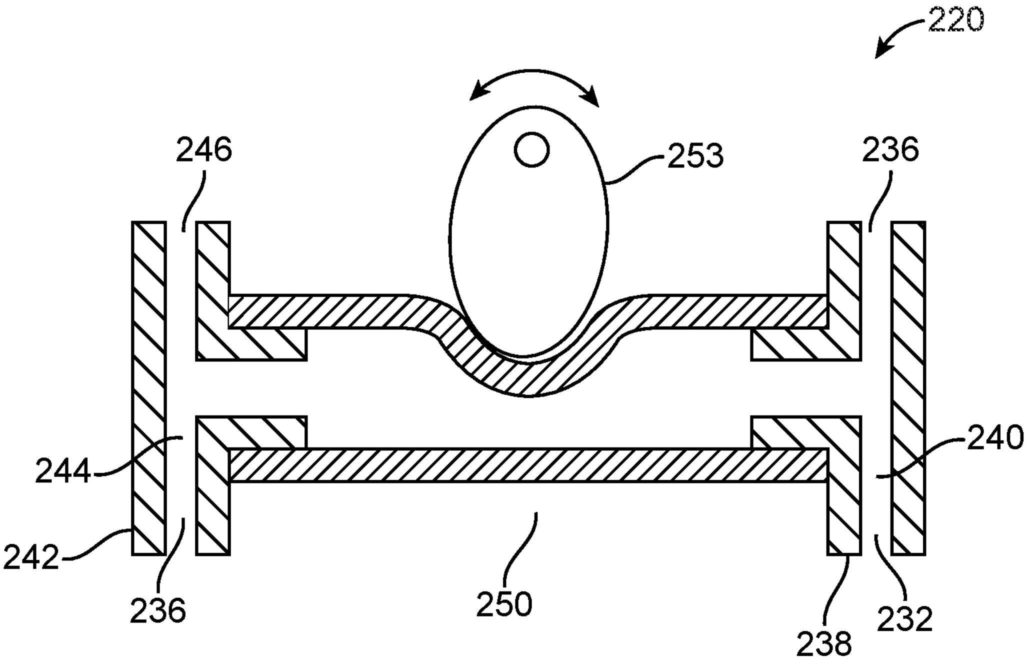
FIG. 53 shows a flow bypass structure of a mechanism according to an embodiment.

Referring back to FIG. 39, the irrigation bypass structure 220 was described having the inlet tube 238 that defines an inlet lumen 240, which connects the inlet 232 with the supply outlet 236 and having the outlet tube 242 that defines the outlet lumen 244, which connects the return inlet 246 with the outlet 236. The irrigation tube connects the supply outlet 236 with return the inlet 246 and carries irrigation fluid through the mechanism head and trigger activation mechanism of various embodiments disclosed herein. The inlet tube 238 is connected with the outlet tube 242 by the bypass 250, which includes a pair of bypass tubes 252 connected by the bypass connector 254. FIG. 53 provides a variation to the bypass structure 220. A dial-controlled cam mechanism 253 can be added to control the tubing bypass diameter and, in turn, the passive flow rate. The dial 253 could be set in manufacturing on per device basis or be tunable by the end user.

Instead of or in addition to the bypass structures previously described (FIGS. 37-42), the irrigation, vacuum, bypass tubes, or other secondary lumens can be fitted with various passive flow applicators for controlling the passive flow rate of the irrigation fluid and/or suction. The passive flow applicator can be used in combination with all the embodiments disclosed herein. One advantage of the passive flow applicator is to provide a minimum level of irrigation fluid to the kidney at all times, which can help reduce tissue trauma and maintain visibility. In this sense, the term "passive flow" means that the user is not necessarily actively pressing a trigger or other actuation mechanism and there is still a flow of irrigation fluid through the device and into the kidney.

Figure 54A:
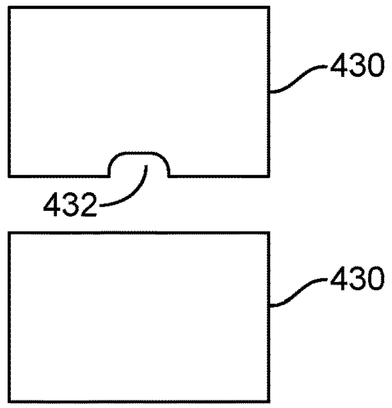
FIGS. 54A and 54B illustrate an embodiment of a passive flow applicator for controlling the passive flow rate of the irrigation fluid and/or suction.
Figure 54B:
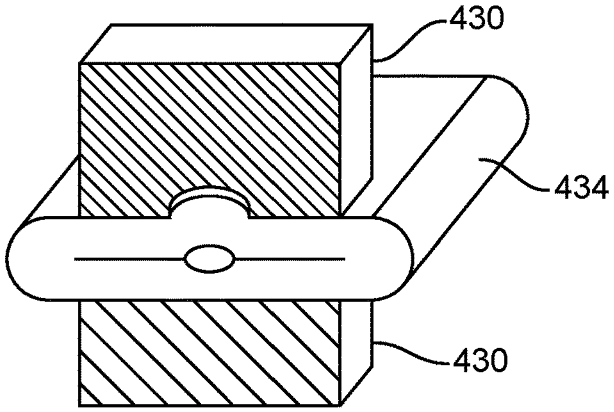

FIGS. 54A and 54B show a two-part component 430 that is configured to releasably pinch the irrigation, vacuum, bypass tubes, and/or secondary tubes in communication with these tube (generally referred to herein as tube 434). The two-part component 430 can be operated by an actuating or biasing mechanism (not illustrated) to apply and release pressure to the tube 434. The degree at which the tube 434 is pinched between the two-part components controls the level of irrigation and/or suction. The upper component 430 can include an extended opening 432 to prevent the component 430 from obstructing the passive flow of irrigation fluid or suction. The opening 432 allows the tube 434 to maintain a minimal clearance in the pinch interface through which irrigate and/or suction can pass and provides a minimum level of irrigation.

Figure 55:
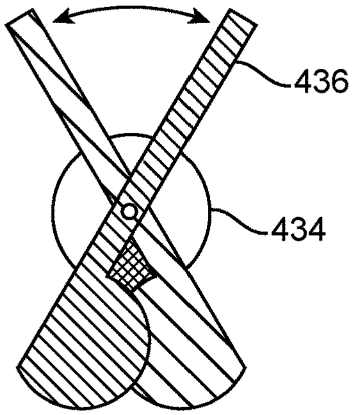
FIG. 55 illustrates an embodiment of a passive flow applicator for controlling the passive flow rate of the irrigation fluid and/or suction.

FIG. 55 illustrates another embodiment of the passive flow applicator. A scissor mechanism 436 is configured to pinch the tube 434. In the neutral state or home position, the scissor mechanism 436 closes down on the tube 434 while allowing passive flow of irrigate and/or suction for a minimum level of irrigation. A user actuated trigger opens the scissors to allow for full flow of irrigate and/or suction. The degree at which tube 434 is pinched between the scissors controls the level of irrigation and/or suction.

Figure 56A:
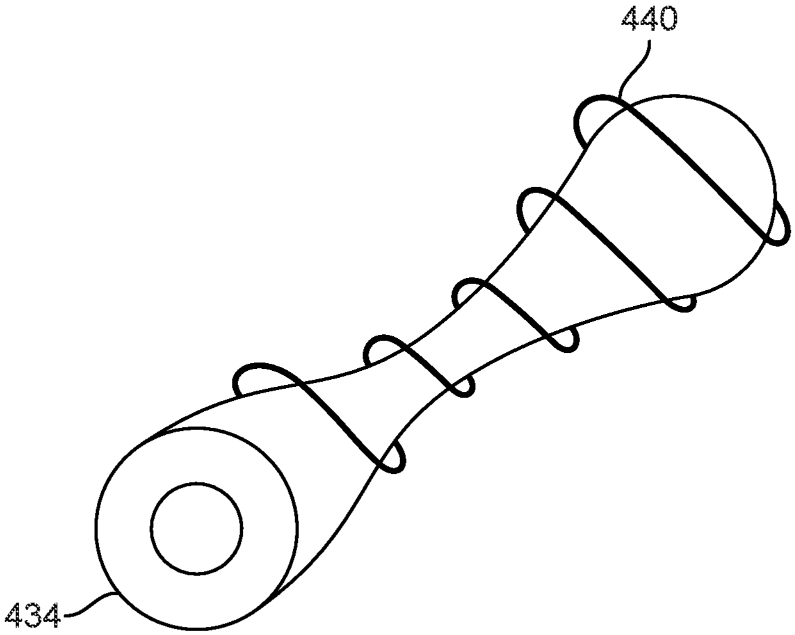
FIGS. 56A and 56B illustrate an embodiment of a passive flow applicator for controlling the passive flow rate of the irrigation fluid and/or suction.
Figure 56B:
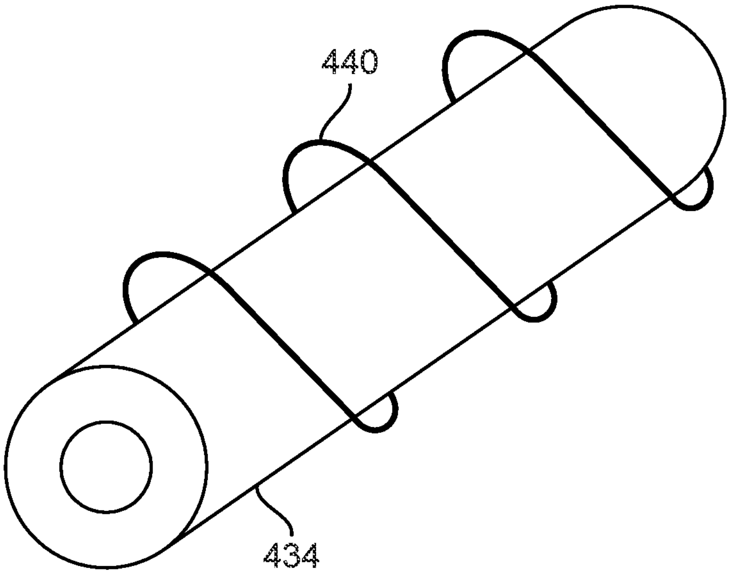

FIGS. 56A and 56B illustrate another embodiment of the passive flow applicator. A shape memory alloy (e.g. Nitinol) wire 440 is wrapped around the tube 434. In the neutral (room temperature) state the wire 440 constrict the tube 434 to allow for minimal passive flow. A heating element (not illustrated) can be used to heat the wire 440 to reduce the constriction allowing for more flow of irrigate and/or suction.

Figure 57A:
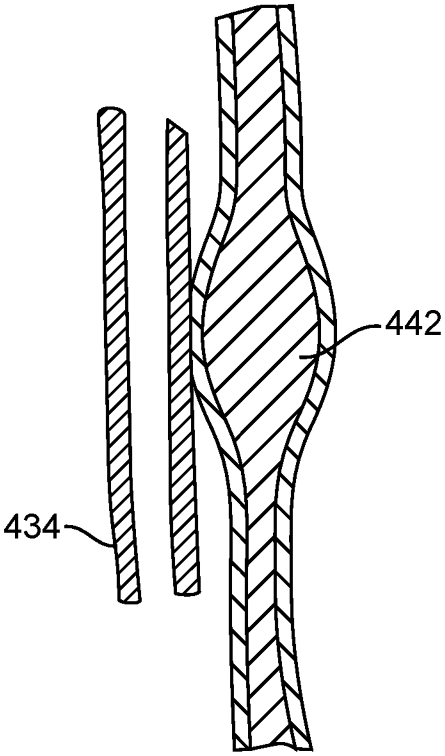
FIGS. 57A and 57B illustrate an embodiment of a passive flow applicator for controlling the passive flow rate of the irrigation fluid and/or suction.
Figure 57B:
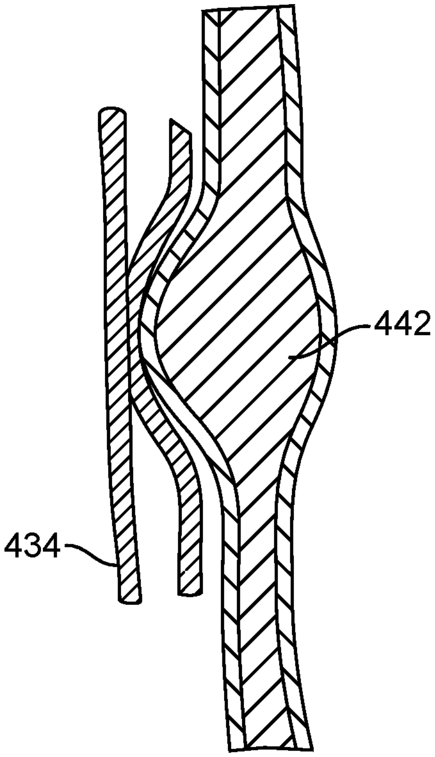

FIGS. 57A and 57B illustrate another embodiment of the passive flow applicator. A balloon 442 can be positioned in abutment to the tube 434. In the balloon's 442 deflated state, the tube 434 is not constricted to allow for full passive flow. The inflation of the balloon gradually constricts the tube 434 passage, thereby completely preventing or limiting the rate or volume of irrigate or suction that can pass through. The degree at which the balloon 442 constricts the tube 434 correlates with the level of irrigation and/or suction.

Figure 58:
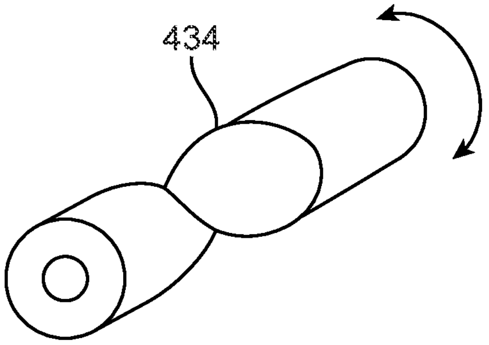
FIGS. 58 and 59 illustrate various means for controlling the passive flow rate of the irrigation fluid and/or suction.
Figure 59:
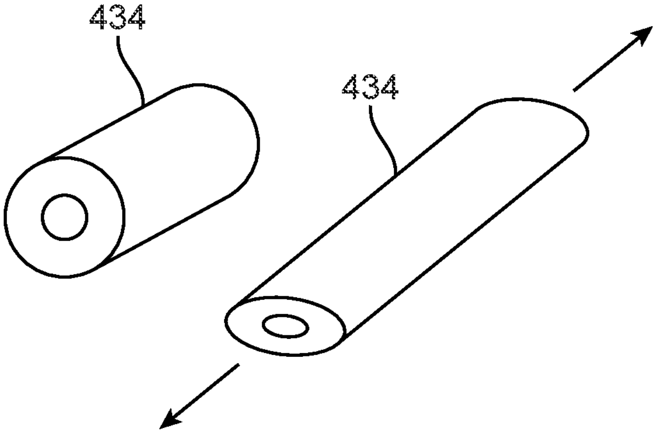

The level of passive flow can also be controlled by providing means for manipulation of the tube 434. Twisting, stretching, and kinking the tube 434 can also restrict the opening through which passive irrigate and/or suction flows. FIG. 58 illustrate a means for twisting the tube 434 to progressively open or close the irrigation and/or suction lumen, thereby manipulating the level of passive flow. FIG. 59 illustrates a means for stretching the tube 434. In the natural position of the tube 434, the irrigation lumen and/or suction lumen would be at its maximum passive flow capability. When the tube 434 is stretched by the user, the diameter of the irrigation lumen and/or suction lumen constricts, thereby causing a reduction in the level at which irrigate and/or suction can pass through the tube 434. The rate or amount of passing irrigate and/or suction can be controlled by the degree at which tube 434 is twisted, stretched, or kinked.

Figure 60A:
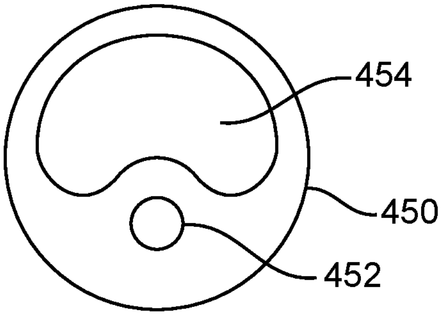
FIGS. 60A and 60B illustrate a multi-lumen tubing having a smaller lumen that allows for passive flow and a larger lumen that channels the active flow of irrigate and/or suction.
Figure 60B:
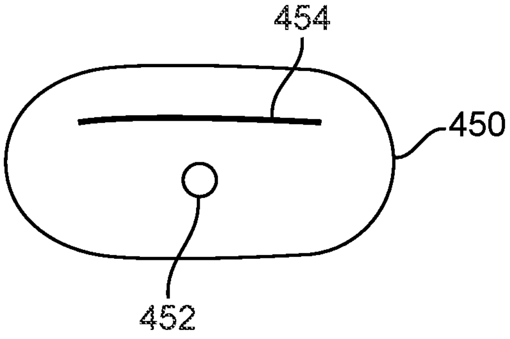

In all the embodiments described herein, the irrigation and/or vacuum tubes can be a multi-lumen tubing. As illustrated in FIGS. 60A and 60B, the multi-lumen tubing 450 comprises a smaller lumen 452 that allows for passive flow and a larger lumen 454 that channels the active flow of irrigate and/or suction. The tubing design is such that when the tubing is pinched, the larger lumen 454 preferentially closes at much lower pinch forces. This preferential closure may be achieved through wall thickness differences or by reinforcing the smaller lumen 452 (via material differences, braiding, etc.).

The various embodiment and variations as described above be combined to manufacture a handle or trigger mechanism having modes of action comprising, or consisting of, one or a combination of the following: passive irrigation off/active irrigation off/active vacuum off, passive irrigation on/active irrigation on/active vacuum on, passive irrigation on/active irrigation on/active vacuum off, passive irrigation off/active irrigation off/active vacuum on, passive irrigation on/active irrigation off/active vacuum off, passive irrigation on/active irrigation off/active vacuum on, passive irrigation off/active irrigation on/active vacuum off, and passive irrigation off/active irrigation on/active vacuum on.

The level of active irrigation and active vacuum can be adjustable. The level of passive irrigation can be adjustable. In some embodiments, the levels of active irrigation and active vacuum can each be independently adjustable, and optionally the level of passive irrigation can be independently adjustable.

In one embodiment, the modes of action comprise, or consist of, a combination of the following modes of action: passive irrigation off/active irrigation off/passive vacuum off/active vacuum off, passive irrigation on/active irrigation off/passive vacuum off/active vacuum off, passive irrigation on/active irrigation off/passive vacuum on/active vacuum off, passive irrigation on/active irrigation on/passive vacuum off/active vacuum off, passive irrigation on/active irrigation on/passive vacuum on/active vacuum off, passive irrigation on/active irrigation on/passive vacuum on/active vacuum on, passive irrigation off/active irrigation off/passive vacuum on/active vacuum on, passive irrigation on/active irrigation on/passive vacuum off/active vacuum on, passive irrigation on/active irrigation off/passive vacuum off/active vacuum on, passive irrigation off/active irrigation off/passive vacuum on/active vacuum off, and passive irrigation off/active irrigation off/passive vacuum off/active vacuum on.

In an embodiment, the level of passive vacuum can be adjustable. In one embodiment the level of active irrigation, passive irrigation, active vacuum, and/or passive vacuum can each be independently adjustable.

The various examples, aspects, and embodiments of the kidney stone removal systems disclosed herein provide various advantages when used to treat kidney stones. One advantage is the ability to prevent or to mitigate the possibility of over pressurizing the kidney during kidney stone treatment. In conventional laser lithotripsy of kidney stones, irrigation fluid can be introduced during ureteroscopy and/or during laser lithotripsy. In most cases, the irrigation fluid can drain out of the kidney only via the narrow space between the ureteroscope and the access sheath. This narrow space can become narrowed further by debris such as kidney stone fragments, clots, or other substances. When the egress of fluid from the kidney is limited by such a narrow space, continued infusion of irrigation fluid creates the risk of high pressures in the kidney, which can cause sepsis and/or other complications. The kidney stone removal system disclosed herein provides a much larger egress channel via the large diameter vacuum lumen. Further, it is possible to apply vacuum through the large diameter vacuum lumen while introducing irrigation fluid. The large diameter of the vacuum lumen in combination with the ability to apply vacuum while delivering irrigation fluid significantly reduces the likelihood of overpressurizing the kidney, resulting in safer kidney stone removal procedures.

Another advantage of the kidney stone removal systems disclosed herein is the ability to prevent or mitigate thermal damage to the kidney during laser lithotripsy. Heat is generated within the kidney during laser lithotripsy of kidney stone, in particular with higher power lasers. This heat can be damaging to the kidney and is a concern for physicians when performing laser lithotripsy. Irrigation fluid can help dissipate the heat via conductive heat transfer, but as described herein irrigation fluid can also build up within the kidney if the pathway for draining is relatively narrow. The kidney stone removal system disclosed herein provides a much larger egress channel via the large diameter vacuum lumen in combination with the ability to apply vacuum while delivering irrigation fluid. The kidney stone removal system disclosed herein can maintain a safe temperature within the kidney by rapidly removing heated irrigation fluid from the kidney and introducing relatively cooler irrigation fluid in a continuous manner during laser lithotripsy. In the examples, aspects, and embodiments of the kidney stone removal system that include a laser guide, heated irrigation fluid can easily and rapidly flow through the vacuum lumen even while the laser fiber is being used to fragment kidney stones and comparatively cooler irrigation fluid can easily and rapidly enter the kidney via the irrigation ports on the nozzle. This rapid heat transfer via irrigation fluid rapidly introduced and removed from the kidney significantly reduces the likelihood of thermal damage to the kidney, resulting in safer kidney stone removal procedures.

Another advantage of the kidney stone removal systems disclosed herein is the ability to improve visibility in the kidney during laser lithotripsy. In conventional laser lithotripsy, debris from fragmenting kidney stones frequently obscures the view from the imaging portion of a ureteroscope and makes it difficult for a physician to see areas of interest within the kidney and/or the kidney stones being fragmented. Physicians often describe a "snow globe" effect during laser lithotripsy in which debris is ejected from the kidney stone in a random and chaotic manner that quickly fills their field of view. The kidney stone removal system disclosed herein can improve visibility by rapidly removing debris fluidized in the irrigation fluid from the kidney through the large diameter vacuum lumen and introducing clear irrigation fluid in a continuous manner during laser lithotripsy. In the examples, aspects, and embodiments of the kidney stone removal system that include a laser guide, debris suspended or fluidized in irrigation fluid can easily and rapidly flow through the vacuum lumen even while the laser fiber is being used to fragment kidney stones. Further, rather than a random and chaotic field of view, the kidney stone removal system disclosed herein provides a predictable pattern as debris moves in a regular motion across the field of view to the vacuum lumen. Such a regular pattern makes it easier for a physician to stay oriented with anatomical landmarks in the field of view. Still further, because of the comparatively large egress channel (as compared to the narrow channel between the ureteroscope and access sheath) more debris is removed and removed faster using the kidney stone removal system disclosed herein. In some cases, even with little or no applied vacuum the large diameter of the vacuum lumen creates sufficient passive outflow to substantially improve visibility. The large diameter of the vacuum lumen in combination with the ability to apply vacuum while delivering irrigation fluid and in combination with the regular debris flow pattern significantly improves visibility during laser lithotripsy, resulting in safer, more efficient, and more effective kidney stone removal procedures.

Another advantage of the kidney stone removal systems disclosed herein is the ability to rapidly apply and remove therapeutic or diagnostic agents in the kidney during laser lithotripsy. The irrigation fluid can have chemical or biological agents applied to it from the source bag or using a port adjacent to the system handle. These agents can be therapeutic, such as, but not limited to, hemostatic, antibiotic, and/or lytic agents. And these agents can be diagnostic, such as, but not limited to, contrast agents.

Another advantage of the kidney stone removal systems disclosed herein is that the irrigation ports can provide a flow rate independent of the tool being used within the vacuum lumen. Conventional ureteroscopes typically provide irrigation through the working channel and this same working channel is used to provide access for laser fibers or baskets. The presence of a tool within the working channel alters the fluid dynamics and changes the flow rate and other flow characteristics. In contrast, the kidney stone removal systems disclosed herein delivers irrigation fluid via dedicated irrigation ports such that the flow characteristics are independent of the tool being used, if any, in the vacuum lumen.

As used herein, connected, attached, coupled or in communication with are terms which can be used interchangeably and when a feature or element is referred to herein as being connected, attached, coupled or in communication with to another feature or element, it can be directly connected to the other feature or element or intervening features or elements may be present. In contrast, when a feature or element is referred to as being directly connected to another feature or element, there are no intervening features or elements present.

When a feature or element is referred to herein as being "on" another feature or element, it can be directly on the other feature or element or intervening features and/or elements may also be present. In contrast, when a feature or element is referred to as being directly on another feature or element, there are no intervening features or elements present.

Although the above descriptions refer to "embodiments," any one of the above-described features or embodiments can be use, implemented, or combined with any other of the features or embodiments described herewith.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature is said to be disposed "adjacent" another feature, it may be positioned next to the other feature without any overlapping or underling portions, or it may have portions that overlap or underlie the adjacent feature.

The spatially relative terms, "proximal," "distal," and the like, may be used herein for ease of description to describe one element's or feature's relationship to another. It will be understood that proximal describes a spatial location closer to the user or the intended position of the user while distal describe a location farther from the user or the intended position of the user. Further, when used with respect to a minimally invasive device like a catheter, proximal and distal locations refer to the portion of the device that is intended to be closer to or farther from the user, respectively, and do not change when the device is in use.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element could be termed a second feature/element, and similarly, a second feature/element could be termed a first feature/element without departing from the teachings of the present invention.

As used herein including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to the value," "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Disclosed herein are systems, devices, and methods for the guided removal of objects in vivo. In particular, the systems, devices, and methods may be adapted to traverse compact areas, such as the urinary tract, and to remove debris, such as kidney stones or fragments of kidney stones, via aspiration through a vacuum tube. As used herein, the term "kidney stones" may refer to fragments of kidney stones, including fragments that have been created by therapeutic fracturing of kidney stones, such as with the device described herein or by another device. The term "kidney stones" may refer to stone or fragments of stones located in the ureter as well as in the kidney and the systems, devices, and methods disclosed herein may be capable of removing kidney stones from the kidney or ureter.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

The invention claimed is:

1. A removably insertable medical device capable of application of an irrigation fluid and a vacuum, comprising:

an elongated tubular body comprising an irrigation lumen for application of the irrigation fluid, and a vacuum lumen for application of the vacuum; and a handle mechanism connected to the elongated tubular body, the handle mechanism configured to be operated by a user for application of the irrigation fluid and the vacuum, the handle mechanism comprising the following modes of action:

passive irrigation off/active irrigation off/active vacuum off, passive irrigation on/active irrigation on/active vacuum on, passive irrigation on/active irrigation on/active vacuum off passive irrigation off/active irrigation off/active vacuum on, passive irrigation on/active irrigation off/active vacuum off, passive irrigation on/active irrigation off/active vacuum on, passive irrigation off/active irrigation on/active vacuum off, and passive irrigation off/active irrigation on/active vacuum on, wherein levels of active irrigation and active vacuum are adjustable, and optionally a level of passive irrigation is adjustable.

2. The insertable medical device of claim 1, wherein the levels of active irrigation and active vacuum are each independently adjustable, and optionally the level of passive irrigation is independently adjustable.

3. The insertable medical device of claim 1, wherein the modes of action additionally comprise passive vacuum, and additionally comprising two or more of the following modes of action:

passive irrigation off/active irrigation off/passive vacuum off/active vacuum off, passive irrigation on/active irrigation off/passive vacuum off/active vacuum off, passive irrigation on/active irrigation off/passive vacuum on/active vacuum off, passive irrigation on/active irrigation on/passive vacuum off/active vacuum off, passive irrigation on/active irrigation on/passive vacuum on/active vacuum off, passive irrigation on/active irrigation on/passive vacuum on/active vacuum on, passive irrigation off/active irrigation off/passive vacuum on/active vacuum on, passive irrigation on/active irrigation on/passive vacuum off/active vacuum on, passive irrigation on/active irrigation off/passive vacuum off/active vacuum on, passive irrigation off/active irrigation off/passive vacuum on/active vacuum off, and passive irrigation off/active irrigation off/passive vacuum off/active vacuum on, wherein optionally a level of passive vacuum is adjustable.

4. The insertable medical device of claim 3, wherein the levels of passive irrigation and passive vacuum are adjustable.

5. The insertable medical device of claim 4, wherein the levels of active irrigation, passive irrigation, active vacuum, and passive vacuum are each independently adjustable.

6. The insertable medical device of claim 1, wherein the insertable medical device is a kidney stone removal mechanism with the vacuum lumen configured to remove a kidney stone or a fragmented kidney stone.

7. The insertable medical device of claim 1, wherein the levels of active and passive irrigation are adjustable by manipulating the irrigation lumen or a secondary lumen in communication with the irrigation lumen.

8. The insertable medical device of claim 7, wherein a device for manipulating comprises:
(a) a pressing element configured to removably apply a force against an outer side of the irrigation or secondary lumen to cause progressive narrowing of an inner channel of the lumen at a part where the pressing element is forced against the lumen;
(b) a piston-type valve operable within a valve cylinder, the valve having apertures configured to communicate with the irrigation or secondary lumen;
(c) a plunger shaft configured to bias back-and-forth in a cylindrical housing, the cylindrical housing having apertures configured to communicate with the irrigation or secondary lumen;
(d) a component configured to pinch the irrigation or secondary lumen to cause narrowing of an inner channel of the lumen at a part where the component pinches the lumen;
(e) a pair of plates such that one plate is rotatable with respect to the other plate, each of the plates having apertures configured to communicate with the irrigation or secondary lumen when at least one of the apertures of the one plate is aligned with respect to an aperture of the other plate; or
(f) a stop component configured to progressively close and open an opening of the irrigation or secondary lumen.

9. The insertable medical device of claim 3, wherein the levels of active and passive vacuum are adjustable by manipulating the vacuum lumen or a secondary lumen in communication with the vacuum lumen.

10. The insertable medical device of claim 9, wherein a device for manipulating comprises:
(a) a pressing element configured to removably apply a force against an outer side of the vacuum or secondary lumen to cause progressive narrowing of an inner channel of the lumen at a part where the pressing element is forced against the lumen;
(b) a piston-type valve operable within a valve cylinder, the valve having apertures configured to communicate with the vacuum or secondary lumen;
(c) a plunger shaft configured to bias back-and-forth in a cylindrical housing, the cylindrical housing having apertures configured to communicate with the vacuum or secondary lumen;
(d) a component configured to pinch the vacuum or secondary lumen to cause narrowing of an inner channel of the lumen at a part where the component pinches the lumen;
(e) a pair of plates such that one plate is rotatable with respect to the other plate, each of the plates having apertures configured to communicate with the vacuum or secondary lumen when at least one of the apertures of the one plate is aligned with respect to an aperture of the other plate; or
(f) a stop component configured to progressively close and open an opening of the vacuum or secondary lumen.

11. The insertable medical device of claim 1, wherein the insertable medical device is a kidney stone removal mechanism, and wherein the handle mechanism comprises a trigger operable by a user, the actuation of which causes selective constriction and un-constriction of a lumen configured for the active application of the irrigation fluid.

12. The insertable medical device of claim 11, wherein the actuation of the trigger causes selective constriction and un-constriction of a lumen configured for the active application of the vacuum such that the constriction and un-constriction of the lumen configured for the active application of the vacuum occurs simultaneously with the constriction and un-constriction of the lumen configured for the active application of the irrigation fluid.

13. The insertable medical device of claim 1, wherein the insertable medical device is a kidney stone removal mechanism, and wherein the handle mechanism comprises a trigger operable by a user, the actuation of which causes concurrent and progressive adjustment of the levels of the applied irrigation fluid and vacuum.

14. The insertable medical device of claim 13, wherein the handle mechanism further comprises a component that indicates to a user a degree at which the trigger is actuated.

15. The insertable medical device of claim 13, wherein the handle mechanism comprises a resilient device that interacts with the trigger to cause the trigger to return to a home position in response to user release of the trigger.

16. The insertable medical device of claim 1, wherein the elongated tubular body is a catheter connected to the handle mechanism, wherein the handle mechanism additionally comprises a steering mechanism for steering a distal tip of the catheter to facilitate insertion and navigation of the catheter through a body passageway and removal of a debris by vacuum.

17. The insertable medical device of claim 3, further comprising a flow indicator in communication with at least one of:
(a) a lumen configured for the active and/or passive application of the irrigation fluid; or
(b) a lumen configured for the active and/or passive application of the vacuum.

18. The insertable medical device of claim 1, wherein the insertable medical device is a kidney stone removal mechanism and wherein the kidney stone removal mechanism comprises a stone catcher in communication with the vacuum lumen.

19. A method of kidney stone removal comprising operating the insertable medical device of claim 1.

20. A removably insertable medical device capable of simultaneous application of an irrigation fluid and vacuum suction, comprising:
an elongated tubular body comprising an irrigation lumen for application of an irrigation fluid, and a vacuum lumen for application of vacuum suction; and
a handle mechanism connected to the elongated tubular body, the handle mechanism comprising a single control mechanism configured to be operated by a user for regulating a rate or an amount of applied irrigation fluid and vacuum suction, wherein the operation of the single control mechanism regulates levels of the applied irrigation fluid and vacuum suction with respect to each other.

21. The insertable medical device of claim 20, wherein the single control mechanism simultaneously constricts and un-constricts a first lumen configured for the application of the irrigation fluid and a second lumen configured for the application of the vacuum suction.

22. The insertable medical device of claim 20, wherein the single control mechanism is a trigger that can be pressed by a user and return back in response to the user releasing the trigger.

23. The insertable medical device of claim 20, wherein the device is a kidney stone removal device.

* * * * *